US012026591B2

(12) United States Patent
Monaghan et al.

(10) Patent No.: US 12,026,591 B2
(45) Date of Patent: *Jul. 2, 2024

(54) CLASSIFICATION IN HIERARCHICAL PREDICTION DOMAINS

(71) Applicant: Optum Services (Ireland) Limited, Dublin (IE)

(72) Inventors: David S. Monaghan, Dublin (IE); Kenneth Bryan, Dublin (IE); Chirag Chadha, Dublin (IE); Brian Carter, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 1233 days.

This patent is subject to a terminal disclaimer.

(21) Appl. No.: 16/523,372

(22) Filed: Jul. 26, 2019

(65) Prior Publication Data

US 2021/0027194 A1 Jan. 28, 2021

(51) Int. Cl.
*G06N 20/00* (2019.01)
*G06N 5/02* (2023.01)

(52) U.S. Cl.
CPC .............. *G06N 20/00* (2019.01); *G06N 5/02* (2013.01)

(58) Field of Classification Search
CPC .......... G06N 20/00; G06N 5/02; G06N 5/022; G06N 20/20
See application file for complete search history.

(56) References Cited

U.S. PATENT DOCUMENTS 8,296,330 B2 * 10/2012 Bennett ................... G06N 5/02
707/803
8,655,915 B2 2/2014 Kenedy et al.
(Continued)

FOREIGN PATENT DOCUMENTS

WO 2014/182725 A1 11/2014
WO 2018/039510 A1 3/2018

OTHER PUBLICATIONS

Mcmahan, "A Survey of Algorithms and Analysis for Adaptive Online Learning," arXiv:1403.3465v3 [cs.LG] Nov. 9, 2015 (Year: 2015).*

(Continued)

*Primary Examiner* — Miranda M Huang
*Assistant Examiner* — Yao David Huang
(74) *Attorney, Agent, or Firm* — ALSTON & BIRD LLP

(57) ABSTRACT

There is a need for solutions that classification solutions in hierarchical prediction domains. This need can be addressed by, for example, performing one or more online machine learning, co-occurrence analysis machine learning, structured fusion machine learning, and unstructured fusion machine learning. In one example, structured predictions inputs are processed in accordance with an online machine learning analysis to generate structurally hierarchical predictions and in accordance with a co-occurrence analysis machine learning analysis to generate structurally non-hierarchical predictions. Then, the structurally hierarchical predictions and the structurally non-hierarchical predictions in accordance with processed by a structured fusion model to generate structure-based predictions. Afterward, the structure-based predictions and non-structure-based predictions are processed in accordance with an unstructured fusion model to generate one or more unstructured-fused predictions.

11 Claims, 34 Drawing Sheets

(56) References Cited

U.S. PATENT DOCUMENTS

| | | | |
|---|---|---|---|
| 11,551,044 | B2 | 1/2023 | Monaghan et al. |
| 2008/0040150 | A1 | 2/2008 | Kao |
| 2009/0119095 | A1 | 5/2009 | Beggelman et al. |
| 2010/0324927 | A1 | 12/2010 | Tinsley |
| 2011/0066425 | A1 | 3/2011 | Hudgins et al. |
| 2012/0110016 | A1 | 5/2012 | Phillips |
| 2012/0158685 | A1 | 6/2012 | White et al. |
| 2012/0166212 | A1 | 6/2012 | Campbell |
| 2014/0046696 | A1 | 2/2014 | Higgins et al. |
| 2014/0181128 | A1 | 6/2014 | Riskin et al. |
| 2015/0356057 | A1 | 12/2015 | Subramanian et al. |
| 2016/0042146 | A1 | 2/2016 | Douglass et al. |
| 2016/0283481 | A1 | 9/2016 | Morley et al. |
| 2018/0060401 | A1 | 3/2018 | Farh et al. |
| 2018/0114334 | A1 | 4/2018 | Desai et al. |
| 2019/0065671 | A1 | 2/2019 | Yandell et al. |
| 2019/0279102 | A1 | 9/2019 | Cataltepe |
| 2020/0005195 | A1 | 1/2020 | Fang et al. |
| 2020/0065384 | A1 | 2/2020 | Costello |
| 2020/0184027 | A1 | 6/2020 | Dolan |
| 2020/0184376 | A1 | 6/2020 | Parameswaran et al. |
| 2020/0242465 | A1* | 7/2020 | Krishnan ........... G06Q 30/0282 |
| 2020/0356875 | A1 | 11/2020 | Wang |
| 2021/0027206 | A1 | 1/2021 | Monaghan et al. |
| 2021/0375407 | A1 | 12/2021 | Wang et al. |

OTHER PUBLICATIONS

Lin et al., "Online Compact Convexified Factorization Machine," WWW 2018, April 23027, 2018, Lyon, France (Year: 2018).*

Valentini et al., "True Path Rule Hierarchical Ensembles for Genome-Wide Gene Function Prediction," in IEEE/ACM Transactions on Computational Biology and Bioinformatics, vol. 8, No. 3, pp. 832-847, May-Jun. 2011, doi: 10.1109/TCBB.2010.38 (Year: 2011).*

Cesa-Bianchi et al., "Synergy of multi-label hierarchical ensembles, data fusion, and cost-sensitive methods for gene functional inference," Mach Learn (2012) 88:209-241. DOI 10.1007/s10994-011-5271-6 (Year: 2012).*

Robinson et al., "A Hierarchical Ensemble Method for DAG-Structured Taxonomies," F. Schwenker et al. (Eds.): MCS 2015, LNCS 9132, pp. 15-26, 2015. DOI: 10.1007/978-3-319-20248-8 2 (Year: 2015).*

NonFinal Office Action for U.S. Appl. No. 16/523,315, dated Mar. 17, 2023, (32 pages), United States Patent and Trademark Office, US.

NonFinal Office Action for U.S. Appl. No. 18/050,074, dated Mar. 16, 2023, (7 pages), United States Patent and Trademark Office, US.

Pisani, Paulo Henrique et al. "Adaptive Biometric Systems Using Ensembles," in IEEE Intelligent Systems, vol. 33, Mo. 2, pp. 19-28, Mar./Apr. 2018, DOI: 10.1109/MIS.2018.111144956 (Year: 2018).

Scheurwegs, Elyne et al. "Data Integration of Structured and Unstructured Sources for Assigning Clinical Codes to Patient Stays," Journal of the American Medical Informatics Association, (Year: 2016), (ePub: Aug. 27, 2015), vol. 23, pp. e11-e19, DOI:10.1093/jamia/ocv115.

Zhang, Fuzheng et al. "Collaborative Knowledge Base Embedding for Recommender Systems," In Proceedings of the 22nd ACM SIGKDD International Conference on Knowledge Discovery and Data Mining Aug. 13-17, 2016, pp. 353-362, San Francisco, CA, USA (Year: 2016), DOI: http://dx.doi.org/10.1145/2939672.2939673.

Corrected Notice of Allowability for U.S. Appl. No. 16/523,351, dated Sep. 8, 2022, (3 pages), United States Patent and Trademark Office, US.

Fu, Ruigang et al. "CNN With Coarse-To-Fine Layer for Hierarchical Classification,", IET Computer Vision, vol. 12, Issue 6, Apr. 12, 2018, pp. 892-899, (Year: 2018), DOI: 10.1049/iet-cvi.2017.0636.

NonFinal Office Action for U.S. Appl. No. 16/523,391, dated Sep. 19, 2022, (98 pages), United States Patent and Trademark Office, US.

Teng, Ervin. "Time-Ordered Online Training of Convolutional Neural Networks," Doctoral Thesis, Carnegie Mellon University, May 2019, pp. 1-132, (Year: 2019).

"How Can I Combine Recommender System Outputs (User Item Matrix) via an Ensemble?," Quora, (5 pages), (online), [Retrieved from the Internet Oct. 14, 2021] <URL: https://www.quora.com/How-can-I-combine-recommender-system-outputs-user-item-matrix-via-an-ensemble>.

"Imagine an Electronic Health Record Designed for Genetics," PhenoTips, (5 pages), (online), [Retrieved from the Internet Oct. 14, 2021] <URL: https://phenotips.com/?utm_source=phenotips.org &utm_medium=301>.

"Monarch Initiative," (2 pages), (online), [Retrieved from the Internet Oct. 14, 2021] <URL: https://monarchinitiative.org/>.

"The Portal for Rare Diseases and Orphan Drugs," Orphanet, (7 pages), (online), [Retrieved from the Internet Oct. 14, 2021] <URL: https://www.orpha.net/consor/cgi-bin/index.php?Ing=EN>.

"Unified Medical Language System (UMLS)," NIH National Library of Medicine, (2 pages), Mar. 10, 2021, (online), [Retrieved from the Internet Oct. 14, 2021] <URL: https://www.nlm.nih.gov/research/umls/index.html>.

Hazim, Amir et al. "Word Embedding Approach for Synonym Extraction of Multi-Word Terms," Proceedings of the Eleventh International Conference on Language Resources and Evaluation (LREC 2018), May 2018, pp. 297-303, available online: https://aclanthology.org/L18-1045.pdf.

Koren, Yehuda. "The Bellkor Solution to the Netflix Grand Prize," Netflix Prize Documentation, vol. 81, Aug. 2009, pp. 1-10.

Leydesdorff Loet et al. "The Semantic Mapping of Words and Co-Words in Contexts," Journal of Informetrics, vol. 5, No. 3, Jul. 1, 2011, (14 pages), available online: http://citeseerx.ist.psu.edu/viewdoc/download?doi=10.1.1.187.2189&rep=rep1&type=pdf.

Notaro, Marco et al. "Prediction of Human Phenotype Ontology Terms by Means of Hierarchical Ensemble Methods," BMC Bioinformatics, Dec. 2017, vol. 18:449, No. 1, pp. 1-18, available online: https://www.ncbi.nlm.nih.gov/pmc/articles/PMC5639780/.

Sill, Joseph et al. "Feature-Weighted Linear Stacking," arXiv preprint arXiv:0911.0460, Nov. 3, 2009, (7 pages), available online: https://arxiv.org/pdf/0911.0460.pdf?lipi=urn%253Ali%253Apage%253Ad_flagship3_pulse_read%253BPZ4T3JLHTu%252BOWNI0d5kFbg%253D%253D.

Toscher, Andreas et al. "The BigChaos Solution to the Netflix Grand Prize," Netflix Prize Documentation, Sep. 5, 2009, pp. 1-52.

Zhou, Qiuju et al. "The Normalization of Occurrence and Co-Occurrence Matrices in Bibliometrics Using Cosine Similarities and Ochiai Coefficients," Journal of the Association for Information Science and Technology, vol. 67, No. 11, Nov. 2016, (27 pages), available online: https://arxiv.org/ftp/arxiv/papers/1503/1503.08944.pdf.

Notice of Allowance for U.S. Appl. No. 16/523,351, dated Aug. 17, 2022, (19 pages), United States Patent and Trademark Office, US.

Cheng, Heng-Tze. "Wide & Deep Learning for Recommender Systems," In Proceedings of the 1st Workshop on Deep Learning for Recommender Systems, Sep. 15, 2016, pp. 7-10. ACM, Boston, Massachusetts. ISBN: 978-1-4503-4795-2. DOI: 10.1145/2988450.2988454.

Dogan, T. "HPO2GO: Prediction of Human Phenotype Ontology Term Associations for Proteins Using Cross Ontology Annotation Co-Occurrences," PeerJ, Aug. 2, 2018. [Retrieved From the Internet Sep. 10, 2019] <https://peerj.com/articles/5298/?utm_source=TrendMD&utm_campaign=PeerJ_TrendMD_1&utm_medium=TrendMD>.

Dogan, Tunca et al. "Human Phenotype Ontology Prediction With the Detection of Co-Occurrences Between HPO Terms and GO Terms," Jul. 20, 2017, (1 page), Middle East Technical University, Dumlupinar Bulv. No. 1, 06800 Çankaya Ankara, Turkey.

Romero, Francisco P. et al. "An Ontology-Based Recommender System for Health Information Management," In Proceedings on the International Conference on Artificial Intelligence (ICAI), (2012), (6 pages), the Steering Committee of the World Congress in Computer Science, Computer Engineering and Applied Computing (WorldComp).

(56) References Cited

OTHER PUBLICATIONS

Wiesner, Martin et al. "Health Recommender Systems: Concepts, Requirements, Technical Basics and Challenges," International Journal of Environmental Research and Public Health, Mar. 2014, vol. 11, No. 3, pp. 2580-2607. DOI: 10.3390/IJERPH110302580.

Final Office Action for U.S. Appl. No. 16/523,391, dated May 30, 2023, (30 pages), United States Patent and Trademark Office, US.

Final Office Action for U.S. Appl. No. 16/523,315, dated Oct. 12, 2023, (31 pages), United States Patent and Trademark Office, US.

Notice of Allowance and Fees Due for U.S. Appl. No. 18/050,074, dated Sep. 7, 2023, (8 pages), United States Patent and Trademark Office, US.

NonFinal Office Action for U.S. Appl. No. 16/523,391, dated Nov. 29, 2023, (34 pages), United States Patent and Trademark Office, US.

Alnashwan et al., "Classification of Online Medical Discourse by Modified Co-training," 2019 IEEE Fifth International Conference on Big Data Computing Service and Applications (BigDataService), Apr. 4-9, 2019 (Year: 2019).

Chen et al., "A Co-training Based Entity Recognition Approach for Cross-Disease Clinical Documents," Concurrency Computat Pract Exper. 2019;31:e4505 (Apr. 27, 2018) (Year: 2018).

Non-Final Rejection Mailed on Mar. 11, 2024 for U.S. Appl. No. 16/523,315, 35 page(s).

Final Rejection Mailed on Mar. 20, 2024 for U.S. Appl. No. 16/523,391, 36 page(s).

Wu, Qingyun, et al. "Returning is believing: Optimizing long-term user engagement in recommender systems." Proceedings of the 2017 ACM on Conference on Information and Knowledge Management. 2017. https://dl.acm.org/doi/abs/10.1145/3132847.3133025 (Year: 2017).

\* cited by examiner

```
                                                                    502
                                                                   ↙

┌─────────────────────────────────────────────────────────────────────────┐
│                                                                         │
│   OBTAIN A FIRST FTRL MODEL CHARACTERIZED BY AN INITIAL VALUE AND A BIAS TERM │
│                                    1001                                 │
│                                                                         │
└─────────────────────────────────────────────────────────────────────────┘
                                     │
                                     ▼
┌─────────────────────────────────────────────────────────────────────────┐
│                                                                         │
│       SET THE INITIAL VALUE TO A NEGATIVE VALUE IN THE FIRST FTRL MODEL │
│                                    1002                                 │
│                                                                         │
└─────────────────────────────────────────────────────────────────────────┘
                                     │
                                     ▼
┌─────────────────────────────────────────────────────────────────────────┐
│                                                                         │
│                   REMOVE THE BIAS TERM FROM THE FTRL MODEL              │
│                                    1003                                 │
│                                                                         │
└─────────────────────────────────────────────────────────────────────────┘
```

FIG. 10

APPEND EACH FEATURE STRING TO EACH CORRESPONDING PREDICTION LABEL
1101
FOR EACH APPENDED TRAINING DATA ENTRY, GENERATE A CORRESPONDING ENCODING LOCATION IN A HIGHLY SPARSE DATA OBJECT
1102
STORE EACH APPENDED TRAINING DATA ENTRY IN THE HIGHLY SPARSE DATA OBJECT BASED ON THE CORRESPONDING ENCODING LOCATION FOR THE APPENDED TRAINING DATA ENTRY
1103
FIG. 11

1600

1601　　　　　　　　　　　　　　　　　　　　　　　　　　　1602

| | HPO | HPO | HPO | HPO | HPO | HPO | HPO | HPO | HPO | HPO | HPO | HPO | HPO | HPO | HPO | HPO | HPO | HPO | HPO | HPO-20 |
|---|---|---|---|---|---|---|---|---|---|---|---|---|---|---|---|---|---|---|---|---|
| ICD-1 | 36 | 22 | 32 | 71 | 33 | 18 | 83 | 6 | 6 | 2 | 82 | 68 | 36 | 71 | 68 | 16 | 88 | 18 | 21 | 28 |
| ICD-2 | 11 | 37 | 8 | 76 | 24 | 18 | 6 | 98 | 84 | 73 | 47 | 47 | 16 | 89 | 93 | 27 | 62 | 46 | 81 | 83 |
| ICD-3 | 6 | 23 | 73 | 83 | 33 | 33 | 47 | 3 | 57 | 38 | 93 | 15 | 73 | 37 | 99 | 32 | 35 | 84 | 97 | 20 |
| ICD-4 | 85 | 66 | 90 | 24 | 69 | 52 | 3 | 34 | 80 | 92 | 27 | 17 | 29 | 47 | 58 | 20 | 57 | 63 | 84 | 76 |
| ICD-5 | 47 | 46 | 12 | 99 | 26 | 38 | 68 | 13 | 74 | 93 | 7 | 19 | 69 | 86 | 43 | 98 | 19 | 16 | 85 | 43 |
| ICD-6 | 77 | 50 | 23 | 54 | 28 | 48 | 86 | 55 | 57 | 77 | 62 | 3 | 62 | 13 | 3 | 70 | 57 | 63 | 19 | 13 |
| ICD-7 | 76 | 36 | 35 | 56 | 60 | 38 | 68 | 96 | 28 | 72 | 84 | 47 | 21 | 42 | 57 | 42 | 1 | 72 | 3 | 93 |
| ICD-8 | 80 | 99 | 37 | 54 | 41 | 93 | 90 | 100 | 55 | 100 | 62 | 21 | 28 | 37 | 5 | 10 | 36 | 88 | 10 | 93 |
| ICD-9 | 89 | 51 | 27 | 17 | 3 | 77 | 89 | 7 | 83 | 64 | 88 | 22 | 2 | 65 | 35 | 43 | 8 | 69 | 86 | 18 |
| ICD-10 | 61 | 74 | 4 | 76 | 90 | 95 | 38 | 64 | 48 | 73 | 25 | 76 | 91 | 15 | 76 | 22 | 84 | 3 | 37 | 43 |
| ICD-11 | 66 | 42 | 86 | 60 | 2 | 3 | 56 | 47 | 89 | 31 | 23 | 40 | 16 | 78 | 71 | 30 | 88 | 68 | 38 | 5 |
| ICD-12 | 13 | 93 | 1 | 75 | 38 | 16 | 44 | 91 | 61 | 20 | 45 | 78 | 88 | 99 | 95 | 74 | 41 | 34 | 50 | 58 |
| ICD-13 | 47 | 47 | 40 | 78 | 65 | 18 | 20 | 16 | 27 | 37 | 14 | 94 | 17 | 85 | 55 | 83 | 90 | 60 | 58 | 35 |
| ICD-14 | 63 | 38 | 32 | 78 | 21 | 84 | 82 | 15 | 40 | 73 | 31 | 15 | 11 | 65 | 76 | 71 | 65 | 89 | 96 | 3 |
| ICD-15 | 57 | 100 | 96 | 92 | 8 | 15 | 38 | 42 | 70 | 77 | 42 | 11 | 34 | 1 | 38 | 25 | 59 | 69 | 21 | 28 |
| ICD-16 | 91 | 20 | 68 | 6 | 8 | 28 | 88 | 52 | 62 | 80 | 30 | 67 | 98 | 14 | 65 | 36 | 64 | 20 | 60 | 30 |
| ICD-17 | 52 | 27 | 99 | 90 | 57 | 47 | 78 | 49 | 86 | 67 | 13 | 48 | 21 | 72 | 87 | 20 | 47 | 50 | 71 | 56 |
| ICD-18 | 36 | 52 | 78 | 11 | 95 | 71 | 99 | 35 | 99 | 4 | 5 | 92 | 2 | 48 | 73 | 96 | 83 | 81 | 62 | 82 |
| ICD-19 | 78 | 57 | 50 | 4 | 55 | 32 | 85 | 84 | 78 | 18 | 24 | 17 | 77 | 23 | 50 | 82 | 4 | 34 | 55 | 71 |
| ICD-20 | 31 | 22 | 1 | 99 | 53 | 89 | 5 | 57 | 74 | 27 | 7 | 76 | 53 | 8 | 63 | 42 | 50 | 59 | 23 | 64 |

┌─────────────────────────────────────────────────────────────────────────┐
│  OBTAIN K STRUCTURALLY HIERARCHICAL PREDICTIONS AND M STRUCTURALLY NON- │
│                       HIERARCHICAL PREDICTIONS                          │
│                                  2001                                   │
└─────────────────────────────────────────────────────────────────────────┘
                                    │
                                    ▼
┌─────────────────────────────────────────────────────────────────────────┐
│   FOR EACH STRUCTURALLY HIERARCHICAL PREDICTION, DETERMINE AN UP-WEIGHTING │
│                                  SCORE                                  │
│                                  2002                                   │
└─────────────────────────────────────────────────────────────────────────┘
                                    │
                                    ▼
┌─────────────────────────────────────────────────────────────────────────┐
│ APPLY THE UP-WEIGHTING SCORES TO THE STRUCTURALLY HIERARCHICAL PREDICTIONS TO │
│ GENERATE AN UPWEIGHTED PREDICTION SCORE FOR EACH STRUCTURALLY HIERARCHICAL │
│                               PREDICTION                                │
│                                  2003                                   │
└─────────────────────────────────────────────────────────────────────────┘
                                    │
                                    ▼
┌─────────────────────────────────────────────────────────────────────────┐
│   GENERATE N SELECTED PREDICTIONS BASED ON EACH UPWEIGHTED PREDICTION SCORE │
│                                  2004                                   │
└─────────────────────────────────────────────────────────────────────────┘
```

| Ranked list | FTR recommendation list | Parents | GrandParents | Great-GrandParents | Great-Great-GrandParents | Upweighting Score |
|---|---|---|---|---|---|---|
| 1 | HPO_0008 | HPO_0027, HPO_0022 | HPO_0213, HPO_0224 | HPO_2113, HPO_2225 | HPO_0000 | 0 |
| 2 | HPO_0006 | HPO_0022 | HPO_0211, HPO_0226 | HPO_2119, HPO_2228 | HPO_0000 | 4·2=2 |
| 3 | HPO_0001 | HPO_0022 | HPO_0222, HPO_0213, HPO_0224 | HPO_2111, HPO_0228 | HPO_0000 | 0 |
| 4 | HPO_0002 | HPO_0021, HPO_0022, HPO_0213, HPO_0222, HPO_0213, HPO_0224 | HPO_2119, HPO_2227 | HPO_0000 | 4·0=4 |
| 5 | HPO_0004 | HPO_0021, HPO_0022 | HPO_0222, HPO_0213, HPO_0224 | HPO_2113, HPO_2228 | HPO_0000 | 4·1=3 |

2400

| One possible newly Ranked list | FTRL recommendation list | Upweighting |
|---|---|---|
| 1 | HPO_0002 | 4 |
| 2 | HPO_0006 | 2 |
| 3 | HPO_0008 | 0 |
| 4 | HPO_0004 | 3 |
| 5 | HPO_0001 | 0 |

OBTAIN NON-STRUCTURE-BASED PREDICTIONS
2501

USE THE NON-STRUCTURE-BASED PREDICTIONS AS GROUND-TRUTH PREDICTION LABELS TO RETRAIN STRUCTURE-BASED PREDICTION MODELS AND GENERATE NEW STRUCTURE-BASED PREDICTIONS USING THE RETRAINED STRUCTURE-BASED PREDICTION MODELS
2502

GENERATE UNSTRUCTURED-FUSED PREDICTIONS BASED ON THE NON-STRUCTURE-BASED PREDICTIONS AND THE NEW STRUCTURED PREDICTIONS
2503

2701 * "A pedigree of branchio-oto-renal dysplasia (the BOR syndrome) is reported, including the documentation by serial audiometric studies of the onset and rapid progression of hearing loss in the twin sister of an affected child..." 2711 2712 2713

* 2721 [27-42] HP_0000110 | renal dysplasia
2722 [150-167] HP_0003678 | rapid progression
2723 [171-183] HP_0000365 | hearing loss

```
In [60]: individual_data[2:]

Out[60]: ['nhi_individual_id_33084158308.0',
          'age_5',
          'gender_F',
          'state_code_TX',
          'icd_9_78060',
          'icd_9_28243',
          'icd_10_B349',
          'icd_9_9953',
          'icd_9_4779',
          'icd_9_4644',
          'icd_9_79009',
          'icd_10_J029',
          'icd_10_J069',
          'icd_9_4659',
          'icd_9_53081',
          'icd_9_V202',
          'icd_9_0340',
          'icd_9_38101',
          'icd_9_0743',
          'icd_9_462',
          'icd_9_7862',
          'icd_10_R197',
          'icd_10_J0190',
          'icd_9_6918',
          'icd_9_2809',
          'icd_9_2859']
```

CLASSIFICATION IN HIERARCHICAL PREDICTION DOMAINS

BACKGROUND

Various embodiments of the present invention address technical challenges related to performing classification in hierarchical prediction domains. Existing classification systems are ill-suited to efficiently and reliably perform classification in hierarchical prediction domains. Various embodiments of the present invention address the shortcomings of the noted existing classification systems and disclose various techniques for efficiently and reliably performing classification in hierarchical prediction domains.

BRIEF SUMMARY

In general, embodiments of the present invention provide methods, apparatus, systems, computing devices, computing entities, and/or the like for classification in hierarchical prediction domains. Certain embodiments utilize systems, methods, and computer program products that enable entity sensitivity classification by using at least one of online machine learning (ML) in hierarchical prediction domains, co-occurrence analysis in hierarchical prediction domains, fusion of structurally hierarchical predictions and structurally non-hierarchical predictions in hierarchical prediction domains, fusion of structure-based predictions and non-structure-based predictions in hierarchical prediction domains, and Human Phenotype Ontology (HPO) predictions in the hierarchical HPO label domain.

In accordance with one aspect, a method is provided. In one embodiment, the method comprises obtaining one or more structurally hierarchical predictions for the one or more prediction inputs, wherein (i) the one or more structurally hierarchical predictions are associated with a hierarchical prediction domain, (ii) the hierarchical prediction domain is associated with one or more predictive hierarchical relationships among a plurality of prediction nodes, (iii) the one or more predictive hierarchical relationships define, for each of the plurality of prediction nodes, a corresponding hierarchical predictive position, and (iv) each structurally hierarchical prediction is determined based at least in part on the hierarchical predictive position of the corresponding prediction node; obtaining one or more structurally non-hierarchical predictions for the one or more prediction inputs, wherein each of the one or more structurally non-hierarchical predictions is determined without regard to the hierarchical predictive position of the corresponding prediction node; obtaining access to a structured fusion machine learning model, wherein the structured fusion machine learning model is configured to perform a structured fusion machine learning analysis based at least in part on the one or more the structurally non-hierarchically predictions and the one or more structurally non-hierarchically predictions to generate one or more structure-based predictions; performing the structured fusion machine learning analysis to generate the one or more structure-based predictions; and generating, based at least in part on the one or more structure-based predictions, the predictive output.

In accordance with another aspect, a computer program product is provided. The computer program product may comprise at least one computer-readable storage medium having computer-readable program code portions stored therein, the computer-readable program code portions comprising executable portions configured to obtain one or more structurally hierarchical predictions for the one or more prediction inputs, wherein (i) the one or more structurally hierarchical predictions are associated with a hierarchical prediction domain, (ii) the hierarchical prediction domain is associated with one or more predictive hierarchical relationships among a plurality of prediction nodes, (iii) the one or more predictive hierarchical relationships define, for each of the plurality of prediction nodes, a corresponding hierarchical predictive position, and (iv) each structurally hierarchical prediction is determined based at least in part on the hierarchical predictive position of the corresponding prediction node; obtain one or more structurally non-hierarchical predictions for the one or more prediction inputs, wherein each of the one or more structurally non-hierarchical predictions is determined without regard to the hierarchical predictive position of the corresponding prediction node; obtain access to a structured fusion machine learning model, wherein the structured fusion machine learning model is configured to perform a structured fusion machine learning analysis based at least in part on the one or more the structurally non-hierarchically predictions and the one or more structurally non-hierarchically predictions to generate one or more structure-based predictions; perform the structured fusion machine learning analysis to generate the one or more structure-based predictions; and generate, based at least in part on the one or more structure-based predictions, the predictive output.

In accordance with yet another aspect, an apparatus comprising at least one processor and at least one memory unit including computer program code is provided. In one embodiment, the at least one memory unit and the computer program code may be configured to, with the processor, cause the apparatus to obtain one or more structurally hierarchical predictions for the one or more prediction inputs, wherein (i) the one or more structurally hierarchical predictions are associated with a hierarchical prediction domain, (ii) the hierarchical prediction domain is associated with one or more predictive hierarchical relationships among a plurality of prediction nodes, (iii) the one or more predictive hierarchical relationships define, for each of the plurality of prediction nodes, a corresponding hierarchical predictive position, and (iv) each structurally hierarchical prediction is determined based at least in part on the hierarchical predictive position of the corresponding prediction node; obtain one or more structurally non-hierarchical predictions for the one or more prediction inputs, wherein each of the one or more structurally non-hierarchical predictions is determined without regard to the hierarchical predictive position of the corresponding prediction node; obtain access to a structured fusion machine learning model, wherein the structured fusion machine learning model is configured to perform a structured fusion machine learning analysis based at least in part on the one or more the structurally non-hierarchically predictions and the one or more structurally non-hierarchically predictions to generate one or more structure-based predictions; perform the structured fusion machine learning analysis to generate the one or more structure-based predictions; and generate, based at least in part on the one or more structure-based predictions, the predictive output.

BRIEF DESCRIPTION OF THE DRAWINGS

Figure 1:
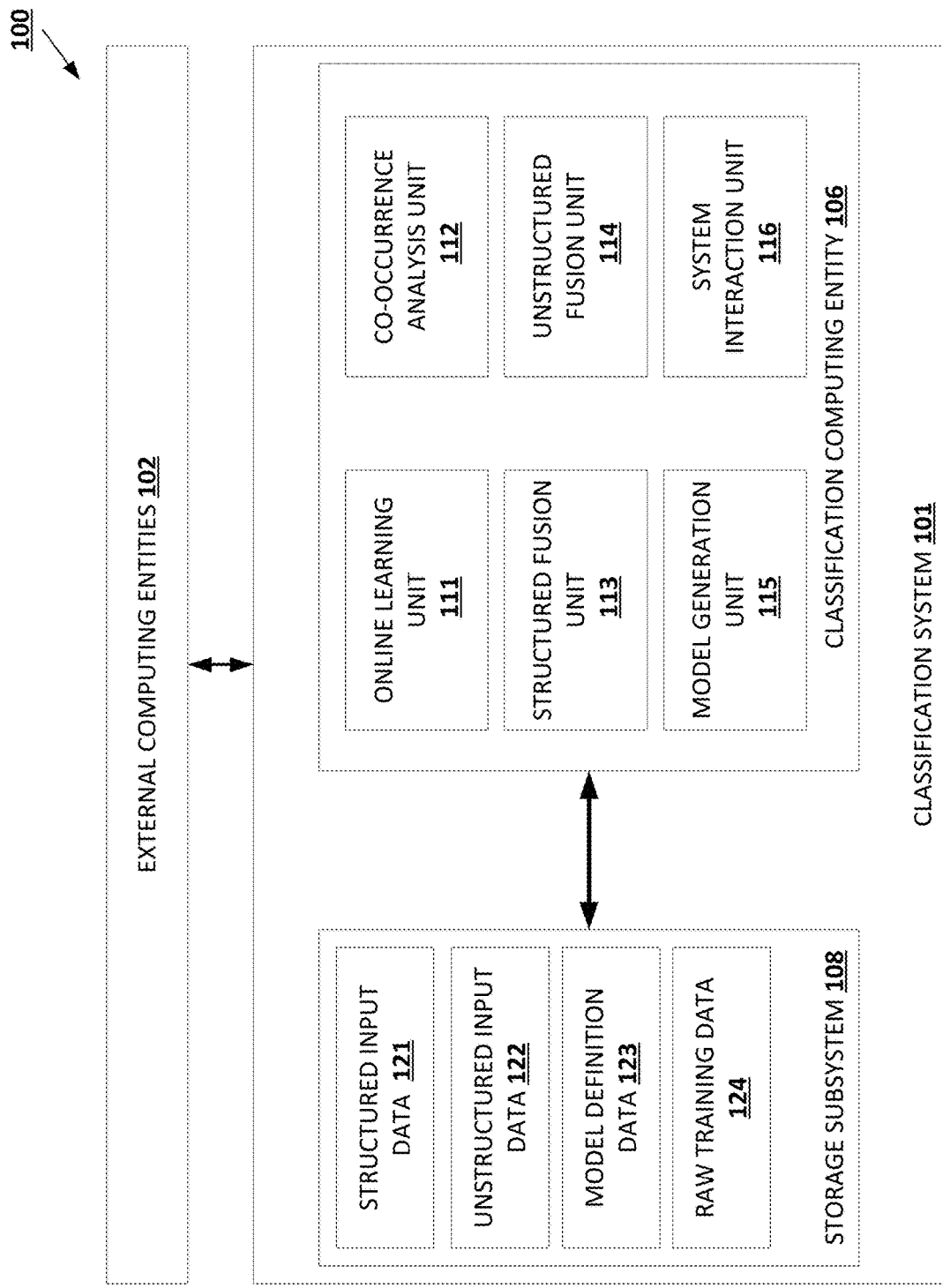

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
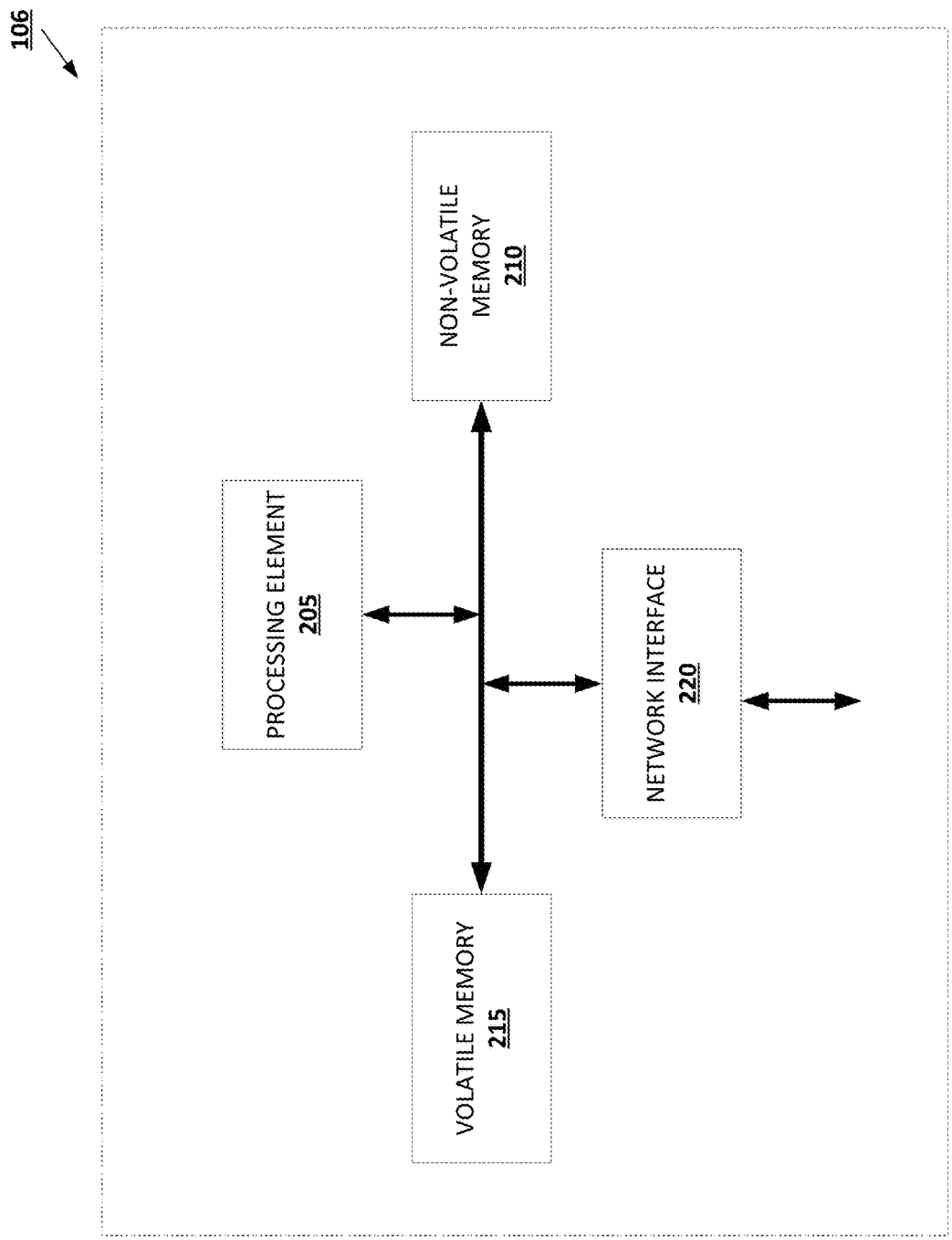

FIG. 2 provides an example classification computing entity in accordance with some embodiments discussed herein.

Figure 3:
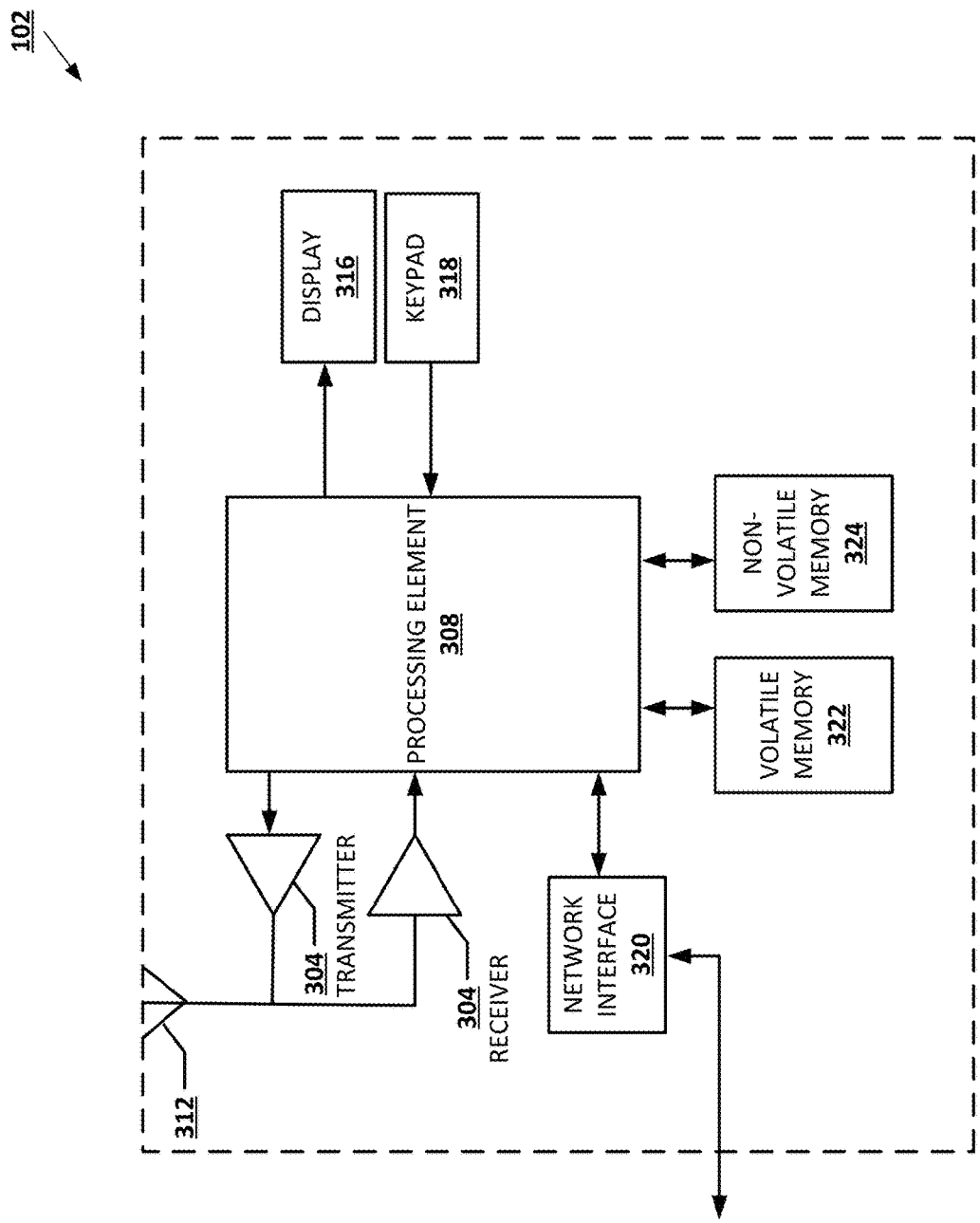

FIG. 3 provides an example external computing entity in accordance with some embodiments discussed herein.

Figure 4A:
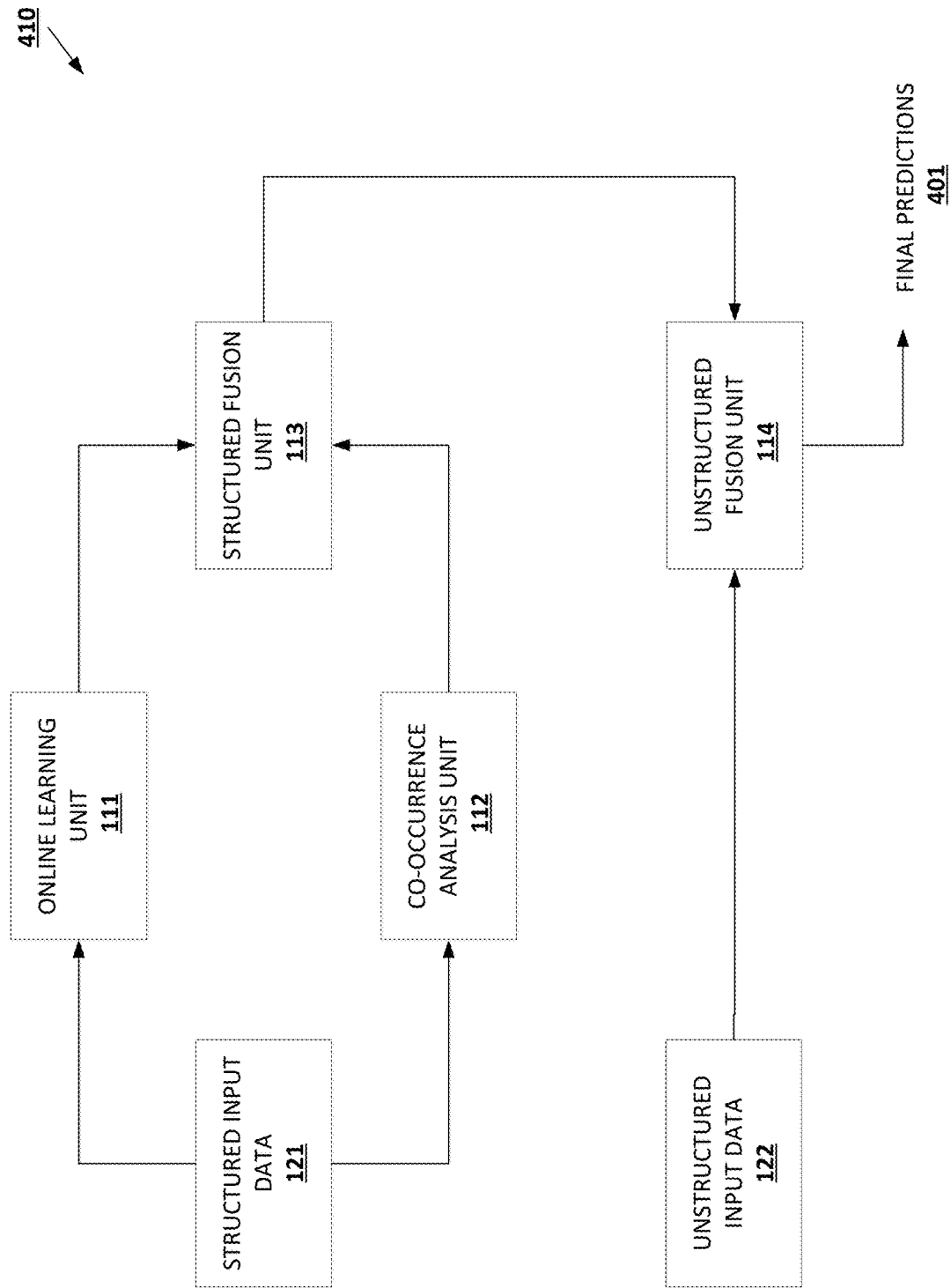
Figure 4B:
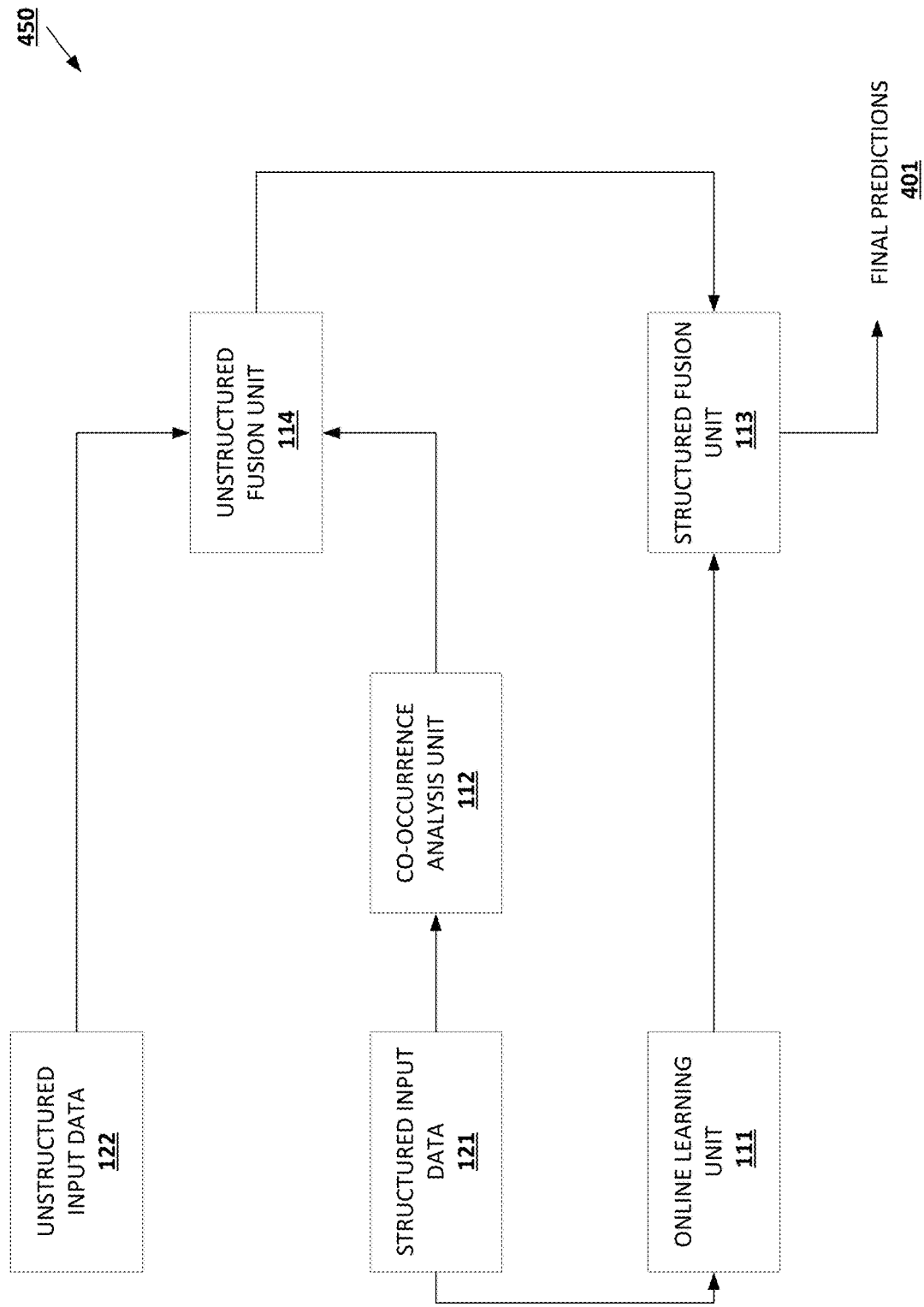

FIGS. 4A-4B provide data flow diagrams of example ensemble architectures for classification in a hierarchical prediction domain in accordance with some embodiments discussed herein.

Figure 5:
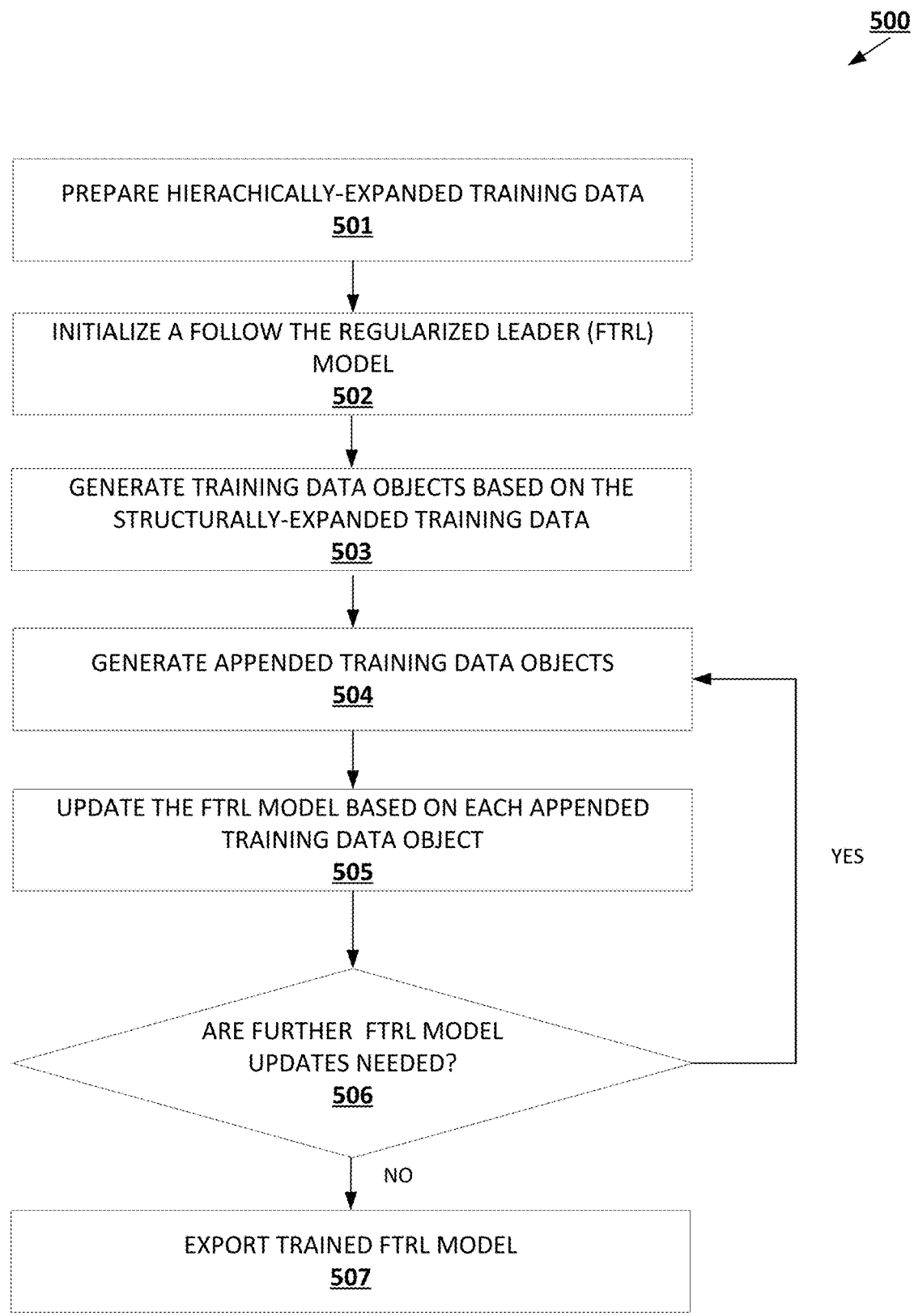

FIG. 5 is a flowchart diagram of an example process for training an online ML model to perform predictive inferences related to a hierarchical prediction domain in accordance with some embodiments discussed herein.

Figure 6:
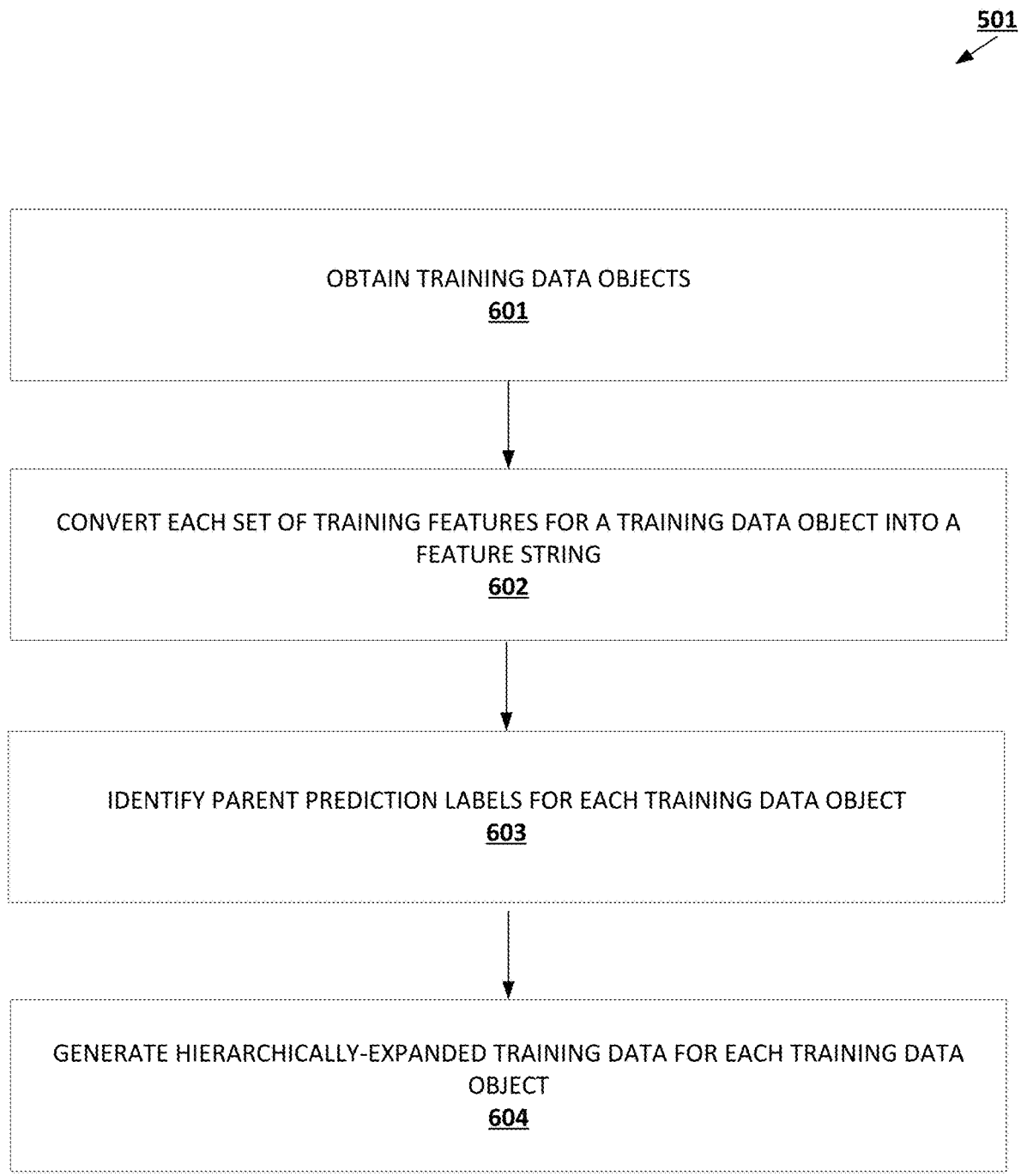

FIG. 6 is a flowchart diagram of an example process for generating hierarchically-expanded training data in accordance with some embodiments discussed herein.

Figure 7:
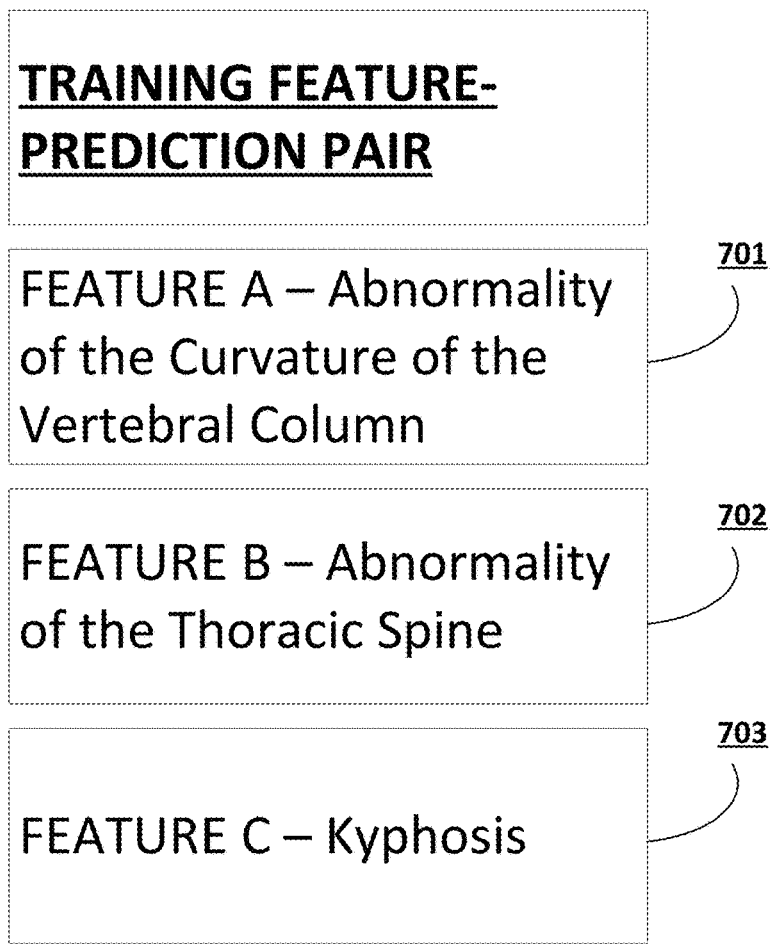

FIG. 7 provides an operational example of a raw training data object set in accordance with some embodiments discussed herein.

Figure 8:
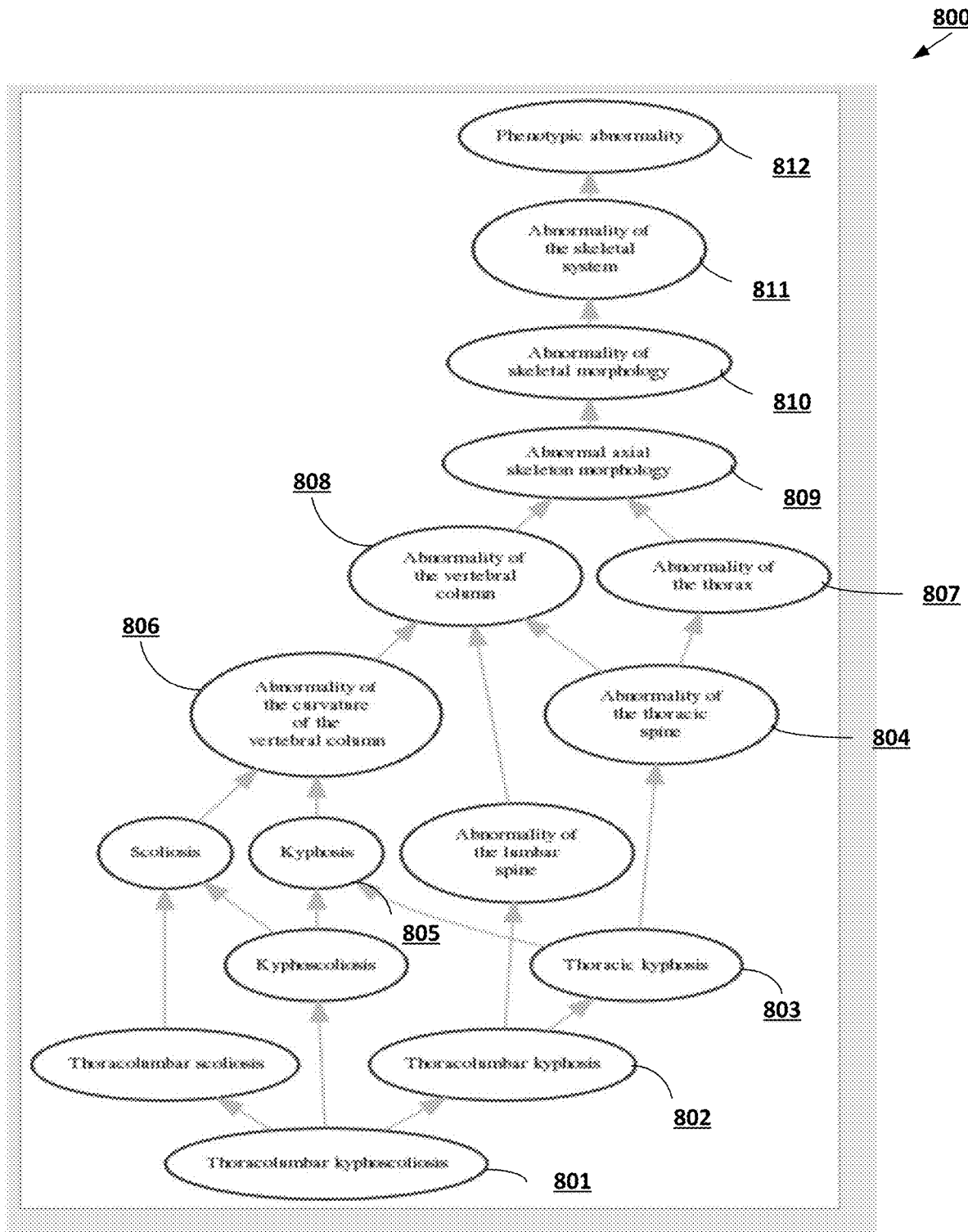

FIG. 8 provides an operational example of a hierarchical prediction domain in accordance with some embodiments discussed herein.

Figure 9:
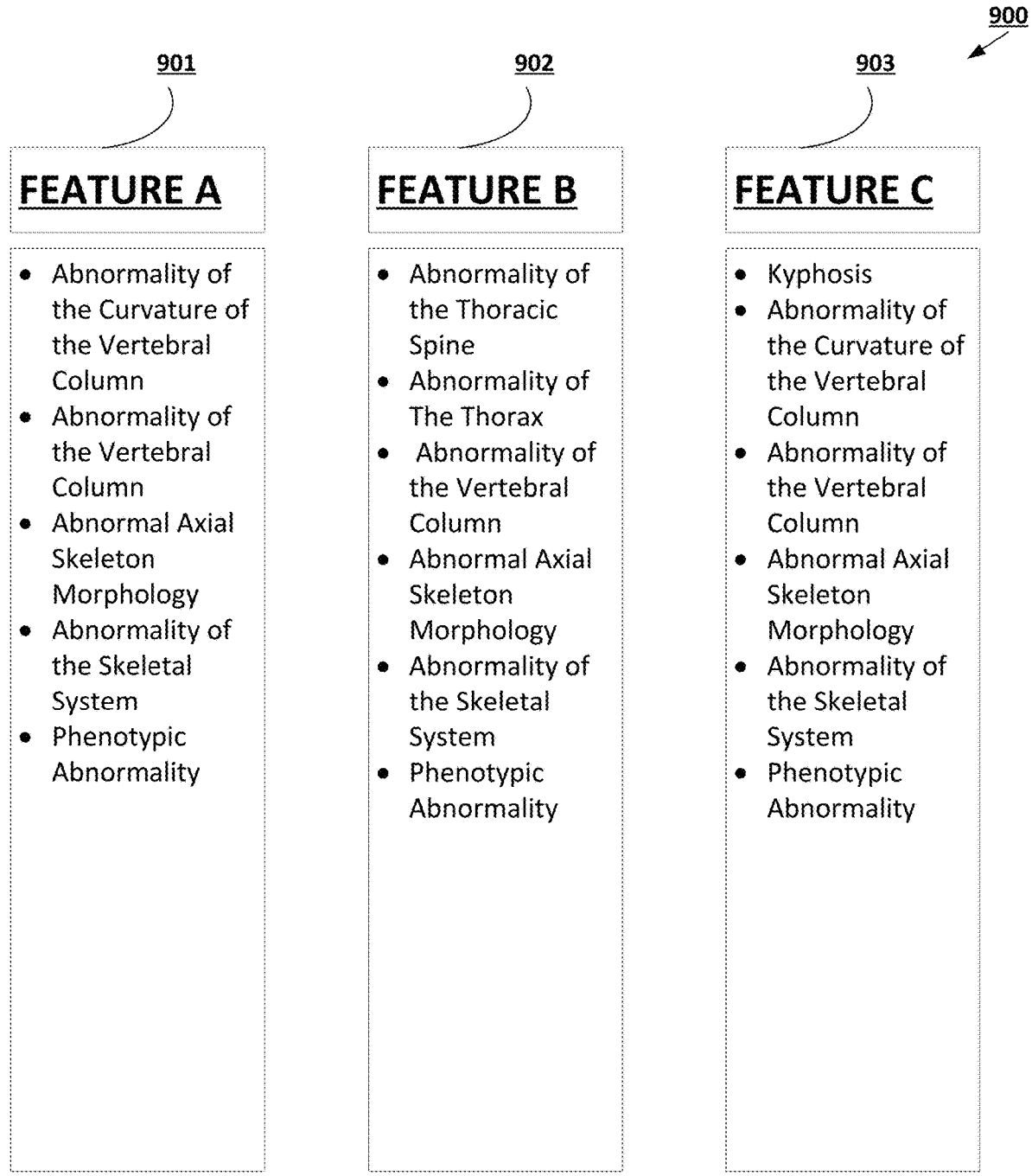

FIG. 9 provides an operational example of a hierarchically-expanded training data object set in accordance with some embodiments discussed herein.

FIG. 10 is a flowchart diagram of an example process for generating initial weight values for a Follow-the-Regularized-Leader (FTRL) ML model in accordance with some embodiments discussed herein.

FIG. 11 is a flowchart diagram of an example process for storing appended training data objects in accordance with some embodiments discussed herein.

Figure 12:
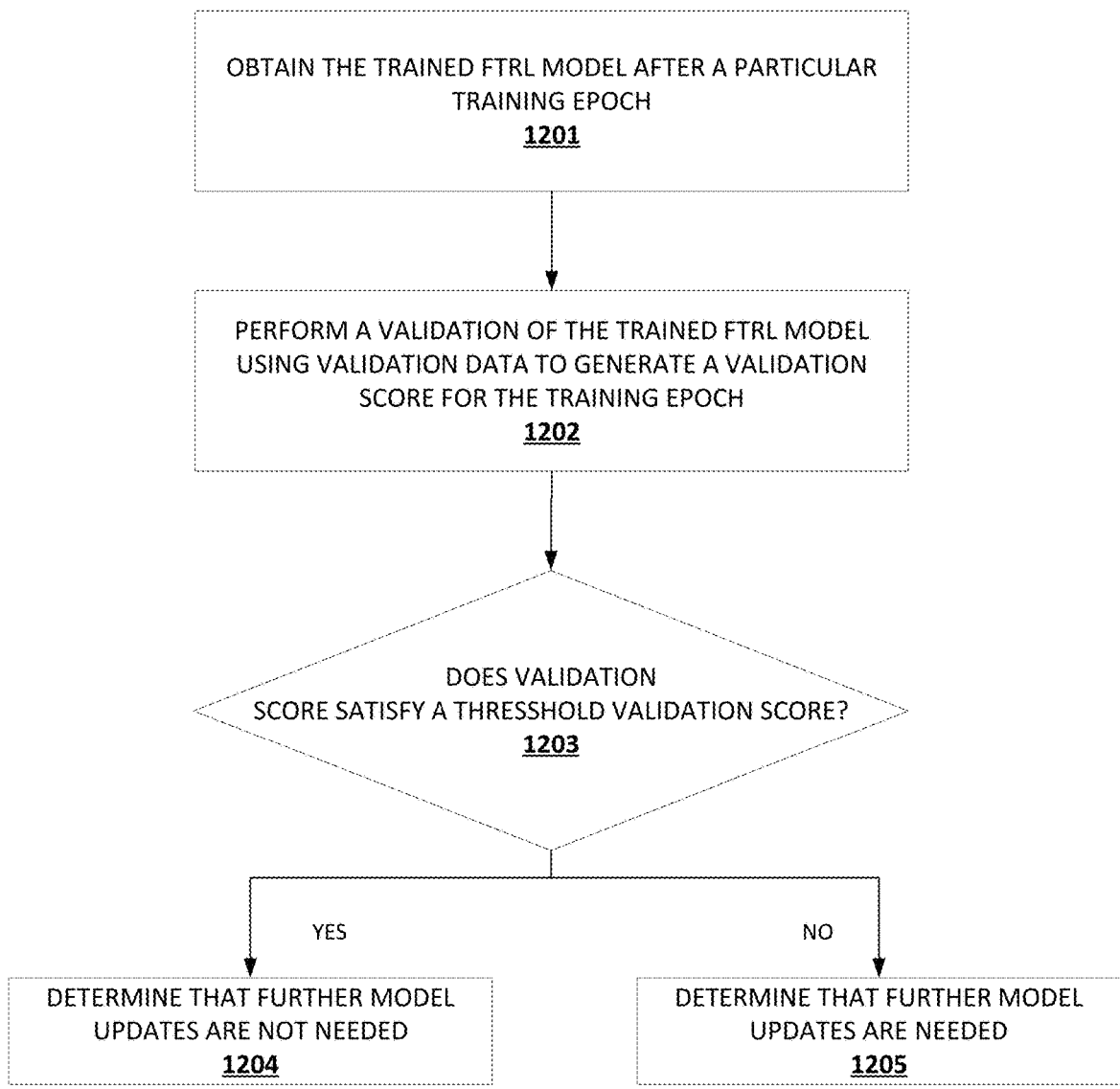

FIG. 12 is a flowchart diagram of an example process for validating an FTRL ML model in accordance with some embodiments discussed herein.

Figure 13:
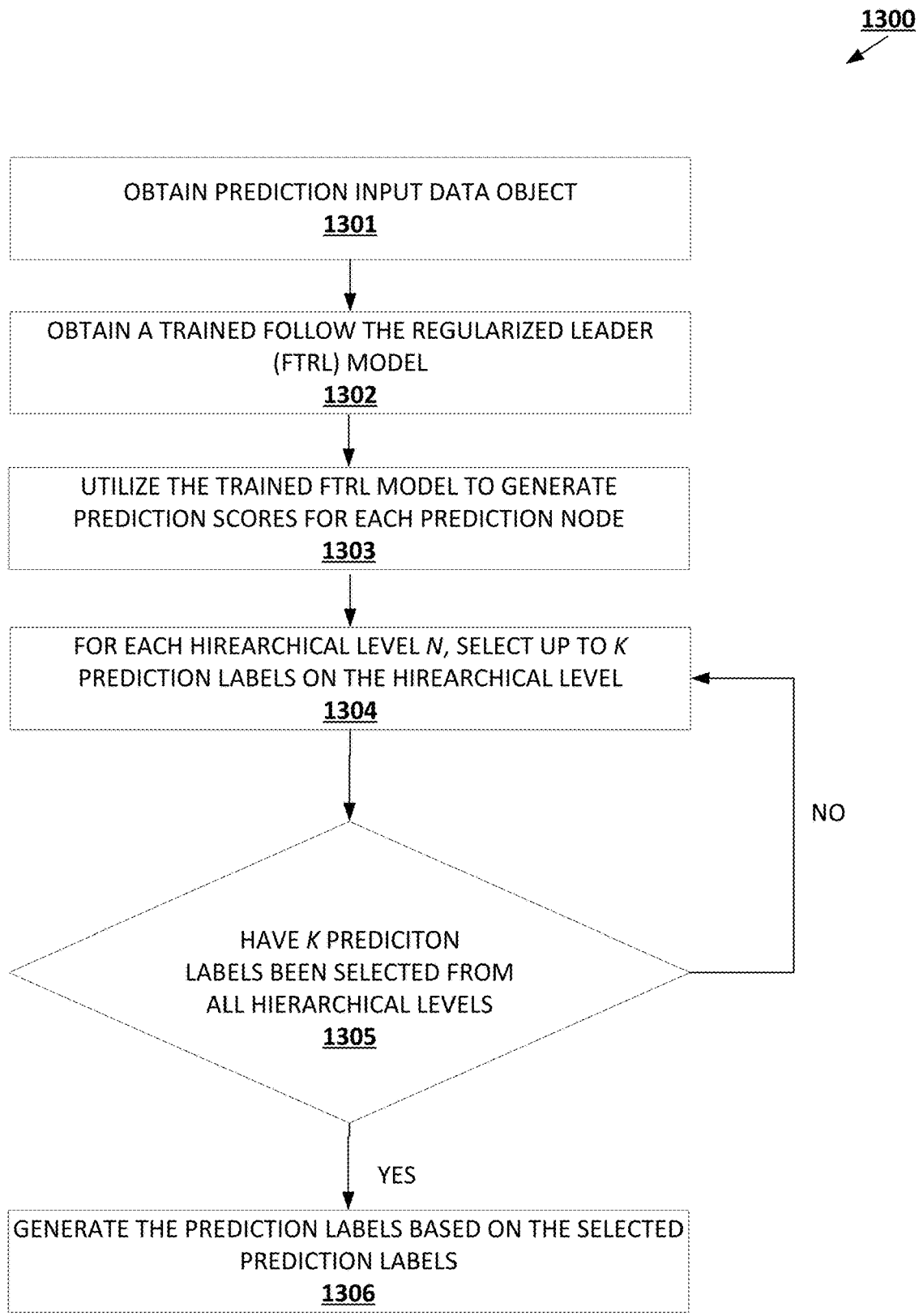

FIG. 13 provides a flowchart diagram of an example process for generating prediction labels using a trained FTRL ML model and in a hierarchical prediction domain in accordance with some embodiments discussed herein.

Figure 14:
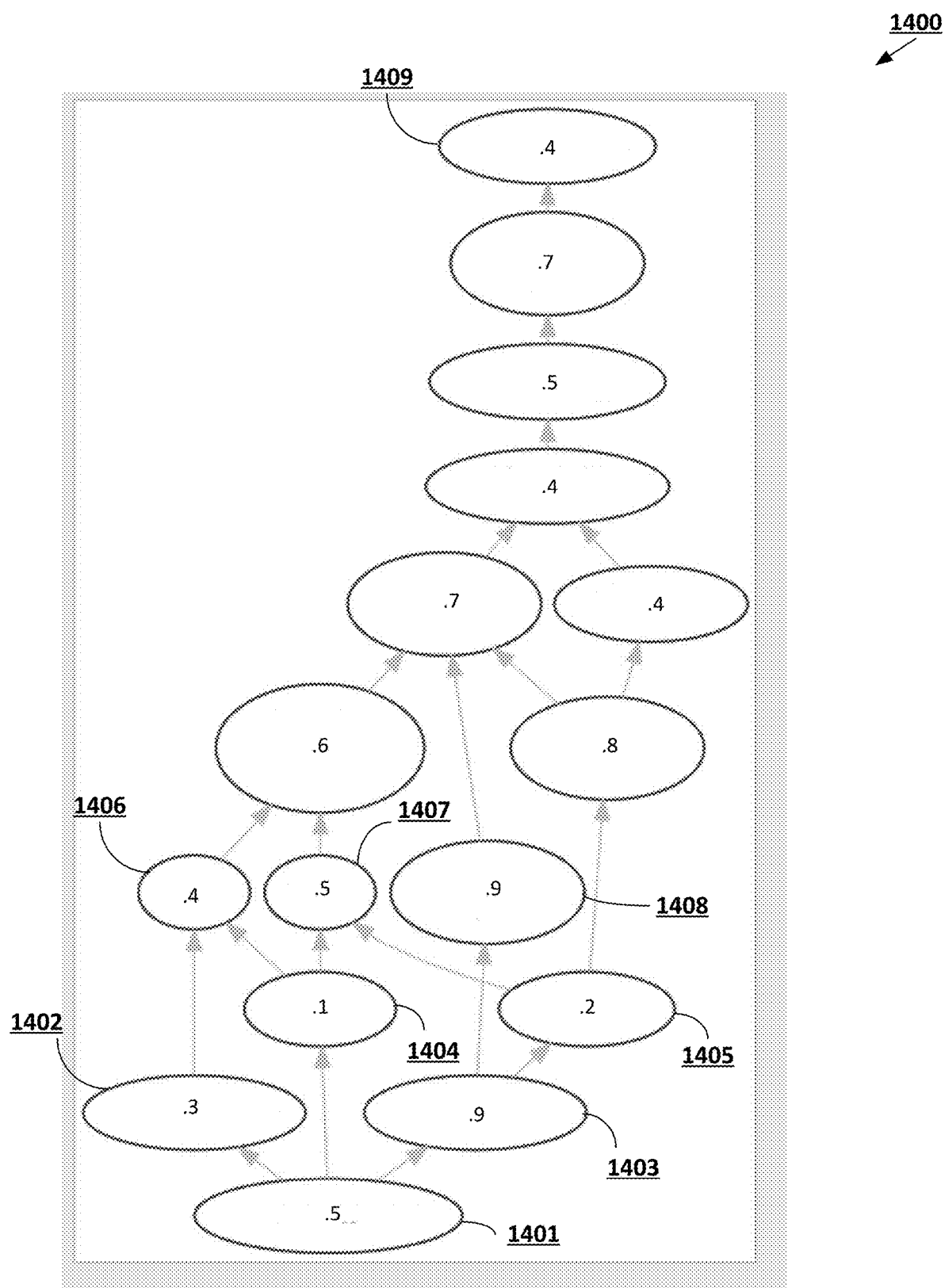

FIG. 14 provides an operational example of a predictive score data object in accordance with some embodiments discussed herein.

Figure 15:
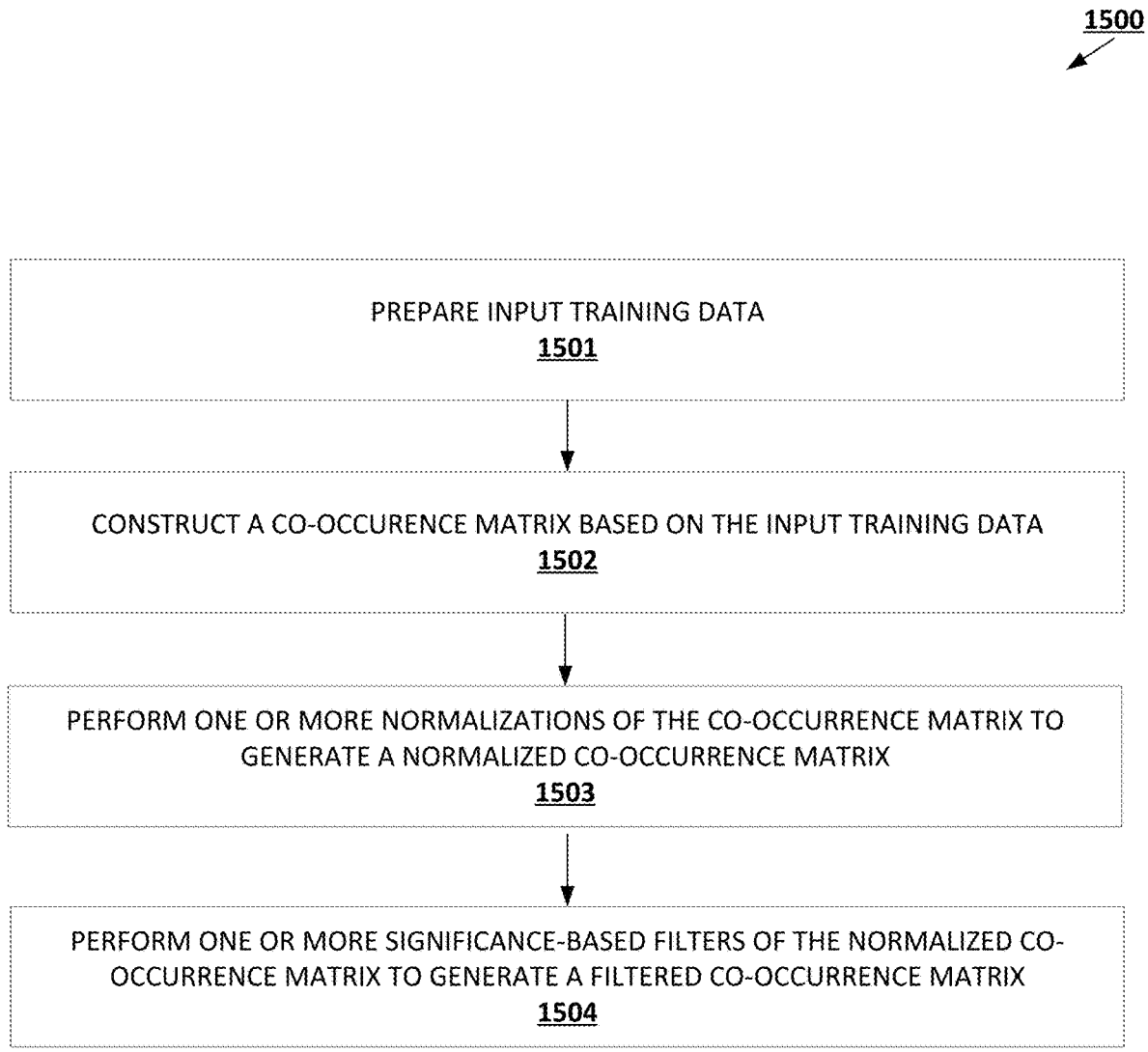

FIG. 15 is a flowchart diagram of an example process for training a co-occurrence analysis ML model in accordance with some embodiments discussed herein.

FIG. 16 provides an operational example of a co-occurrence matrix in accordance with some embodiments discussed herein.

Figure 17:
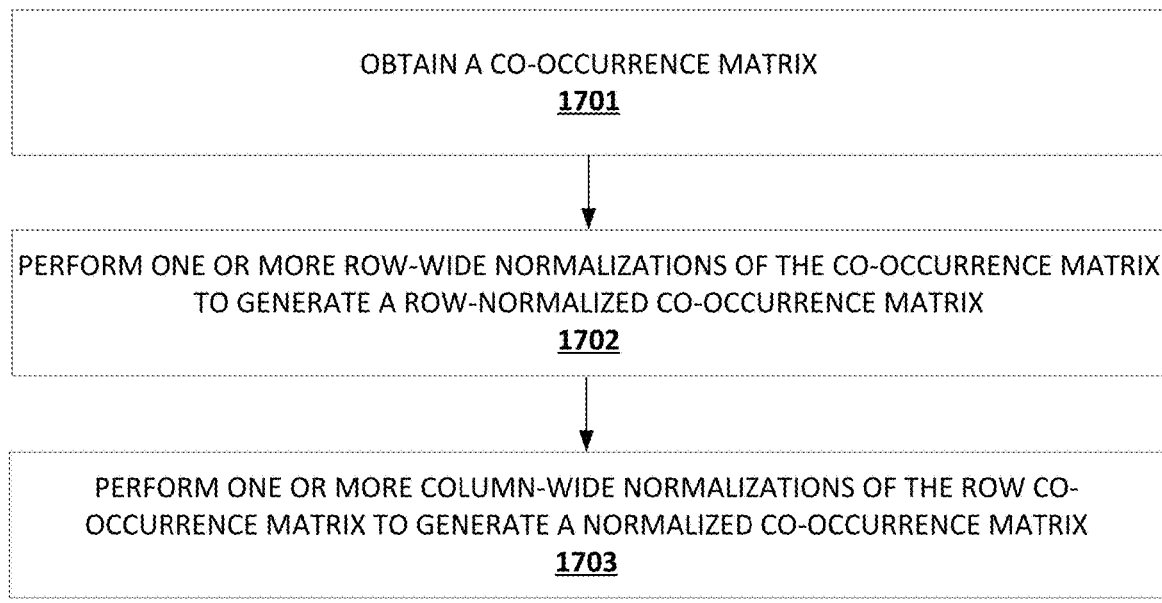

FIG. 17 is a flowchart diagram of an example process for generating a normalized co-occurrence matrix in accordance with some embodiments discussed herein.

Figure 18:
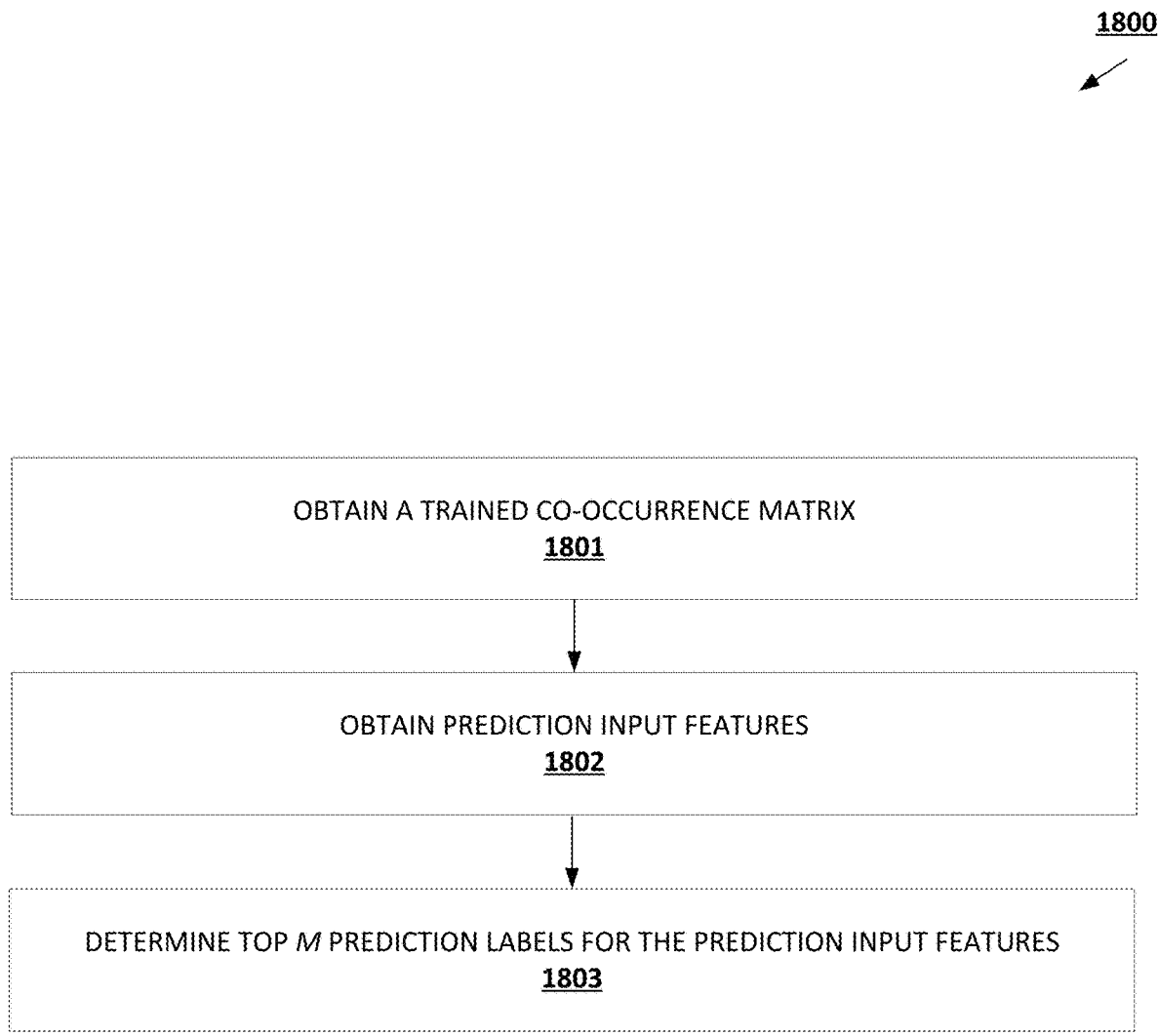

FIG. 18 is a flowchart diagram of an example process for generating predictions using a trained co-occurrence analysis ML model in accordance with some embodiments discussed herein.

Figure 19:
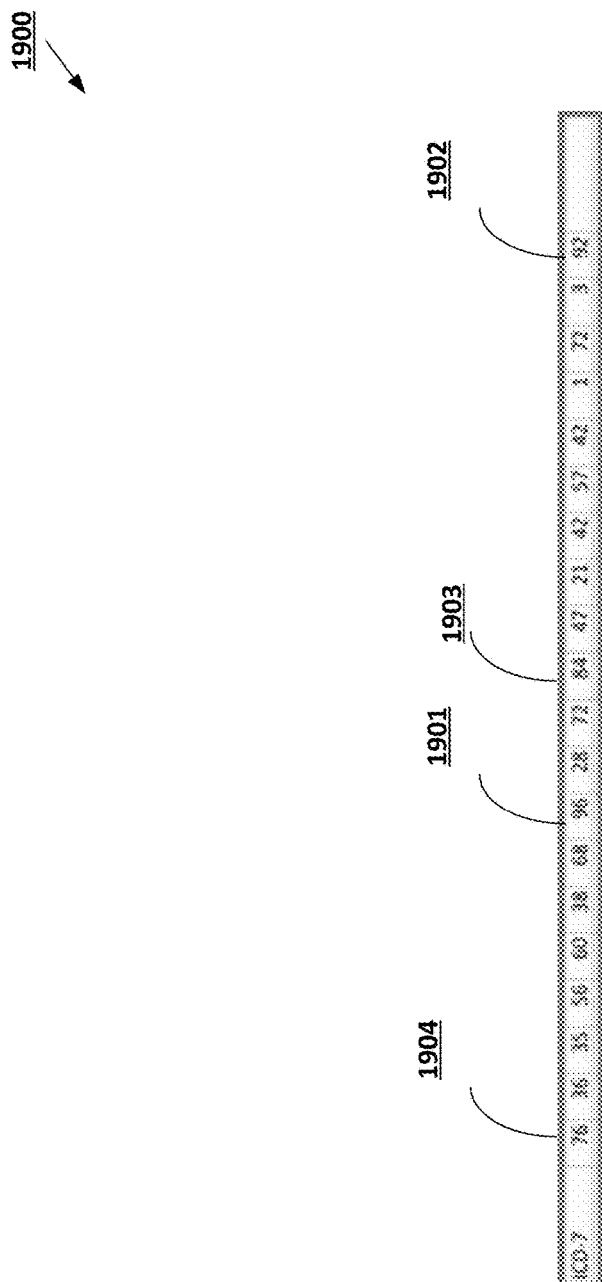

FIG. 19 provides an operational example of a co-occurrence values set for a training feature in accordance with some embodiments discussed herein.

FIG. 20 is a flowchart diagram of an example process for generating predictions based on structurally hierarchical predictions and structurally non-hierarchically predictions in accordance with some embodiments discussed herein.

Figure 21:

FIG. 21 provides an operational example of a structurally hierarchical prediction set in accordance with some embodiments discussed herein.

Figure 22:
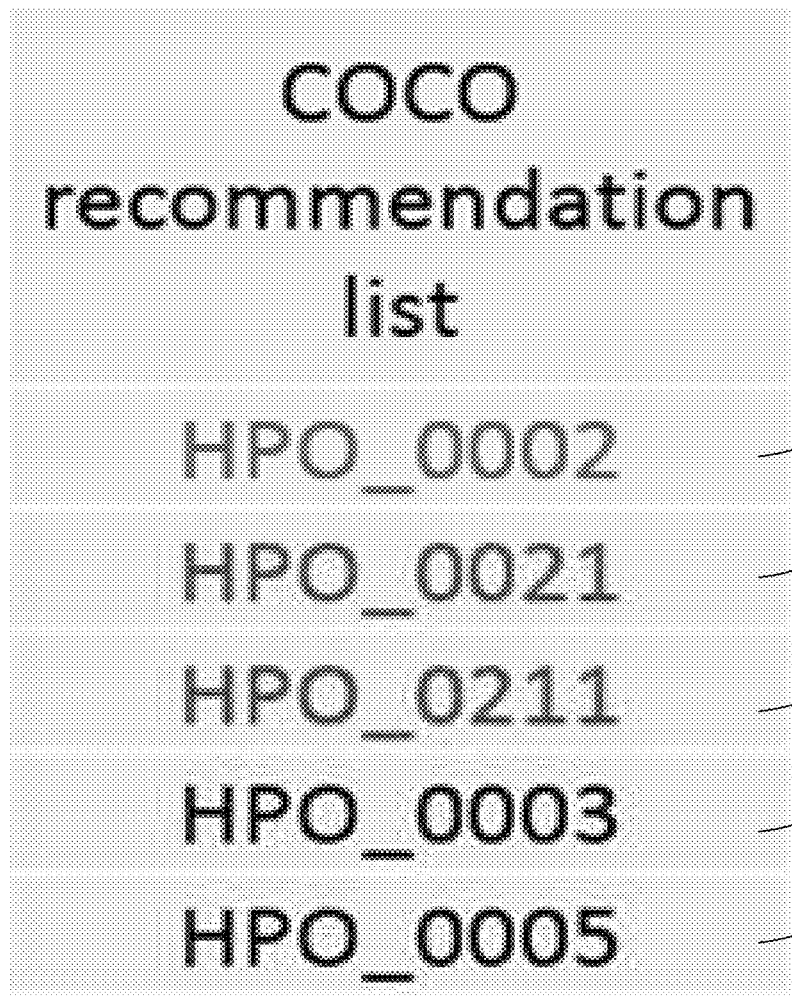

FIG. 22 provides an operational example of a structurally non-hierarchical prediction set in accordance with some embodiments discussed herein.

FIG. 23 provides operational example of an up-weighting score generation data structure in accordance with some embodiments discussed herein.

FIG. 24 provides an operational example of an up-weighting adjustment data structure in accordance with some embodiments discussed herein.

FIG. 25 provides a flowchart diagram of an example process for performing an unstructured fusion of structure-based predictions and non-structure-based predictions in accordance with some embodiments discussed herein.

Figure 26:
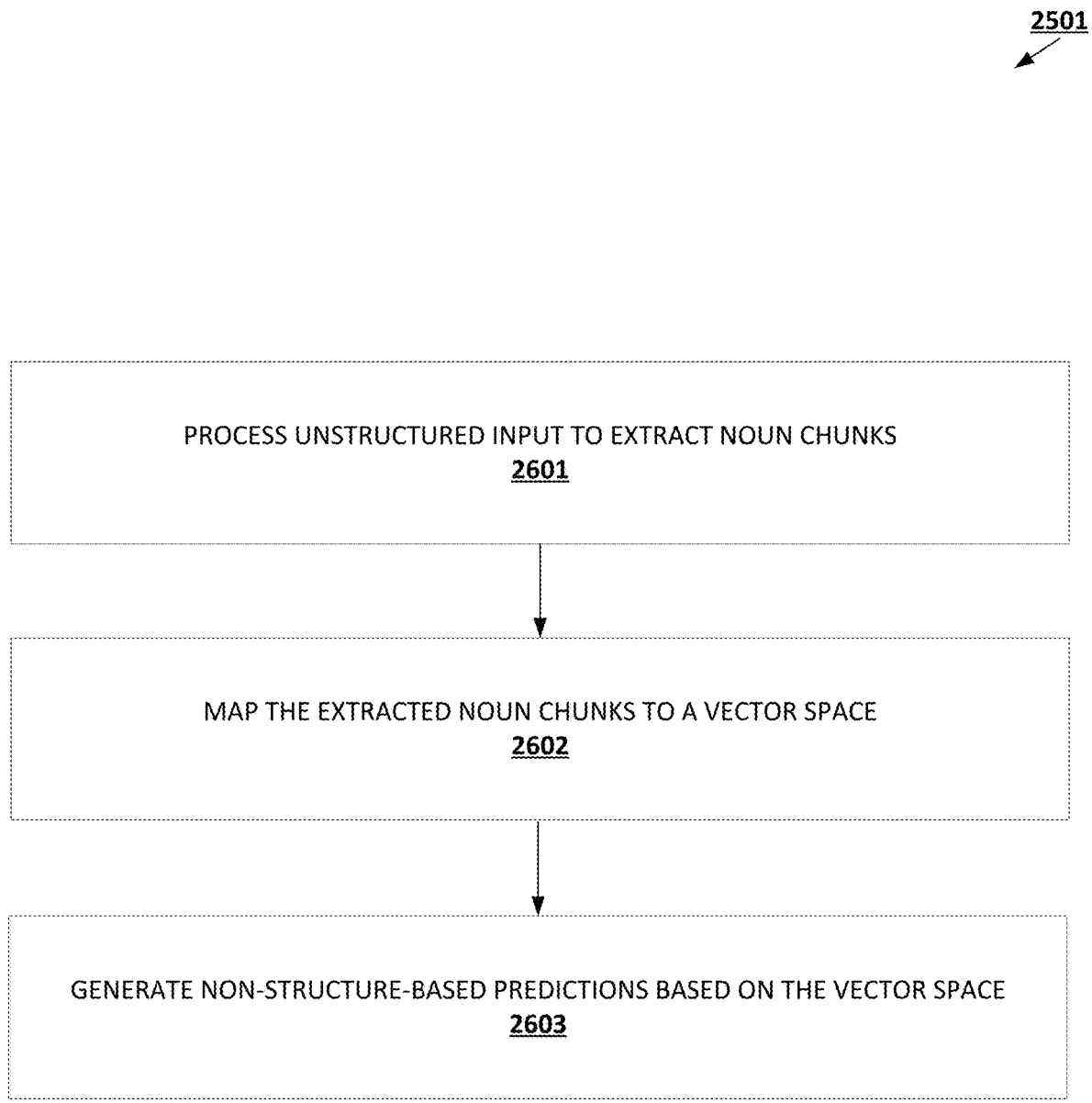

FIG. 26 is a flowchart diagram of an example process for generating structurally non-hierarchical predictions based on unstructured prediction inputs in accordance with some embodiments discussed herein.

FIG. 27 provides an operational example of an unstructured input data object in accordance with some embodiments discussed herein.

Figure 28:
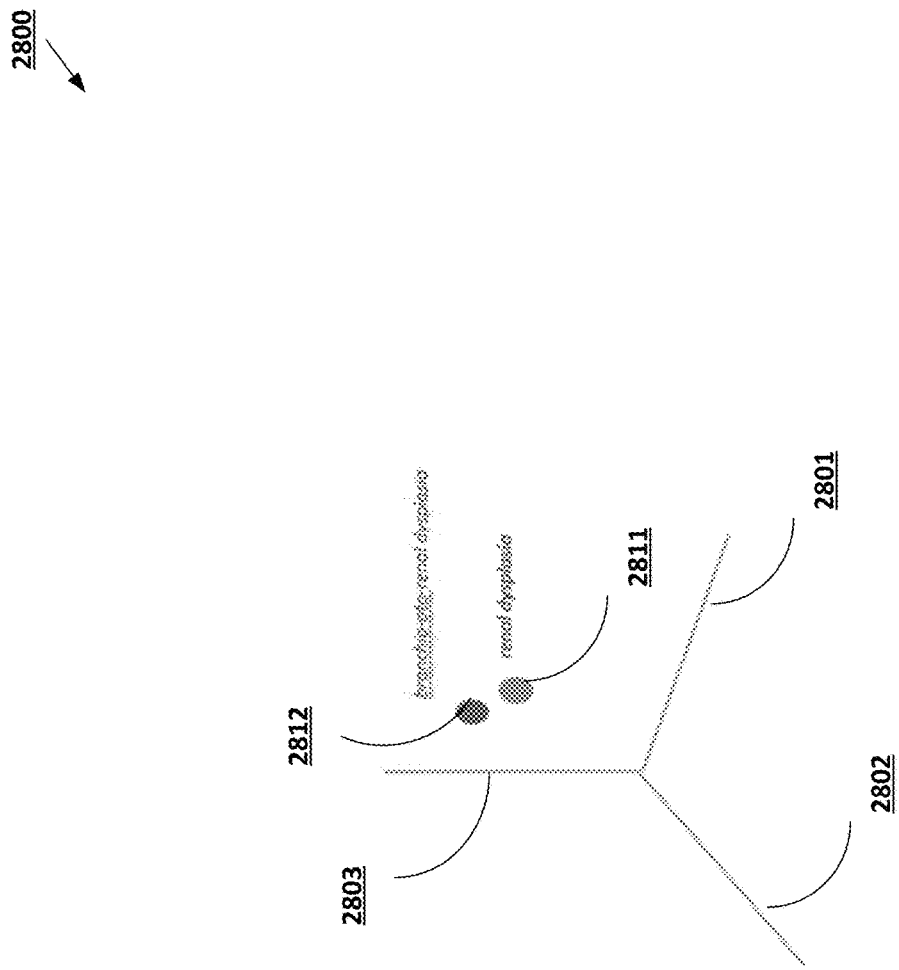

FIG. 28 provides an operational example of a non-structure-based prediction vector space in accordance with some embodiments discussed herein.

Figure 29:
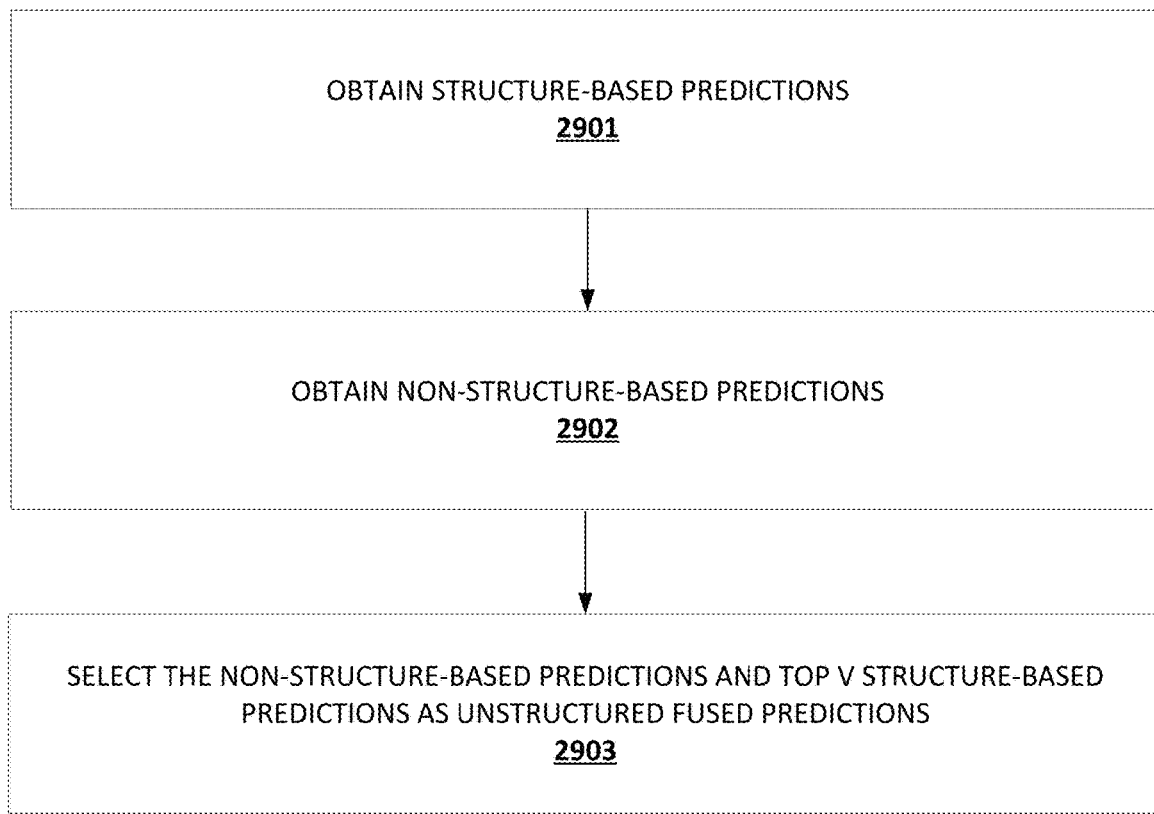

FIG. 29 is a flowchart diagram of an example process for generating unstructured-fused predictions in accordance with some embodiments discussed herein.

Figure 30:
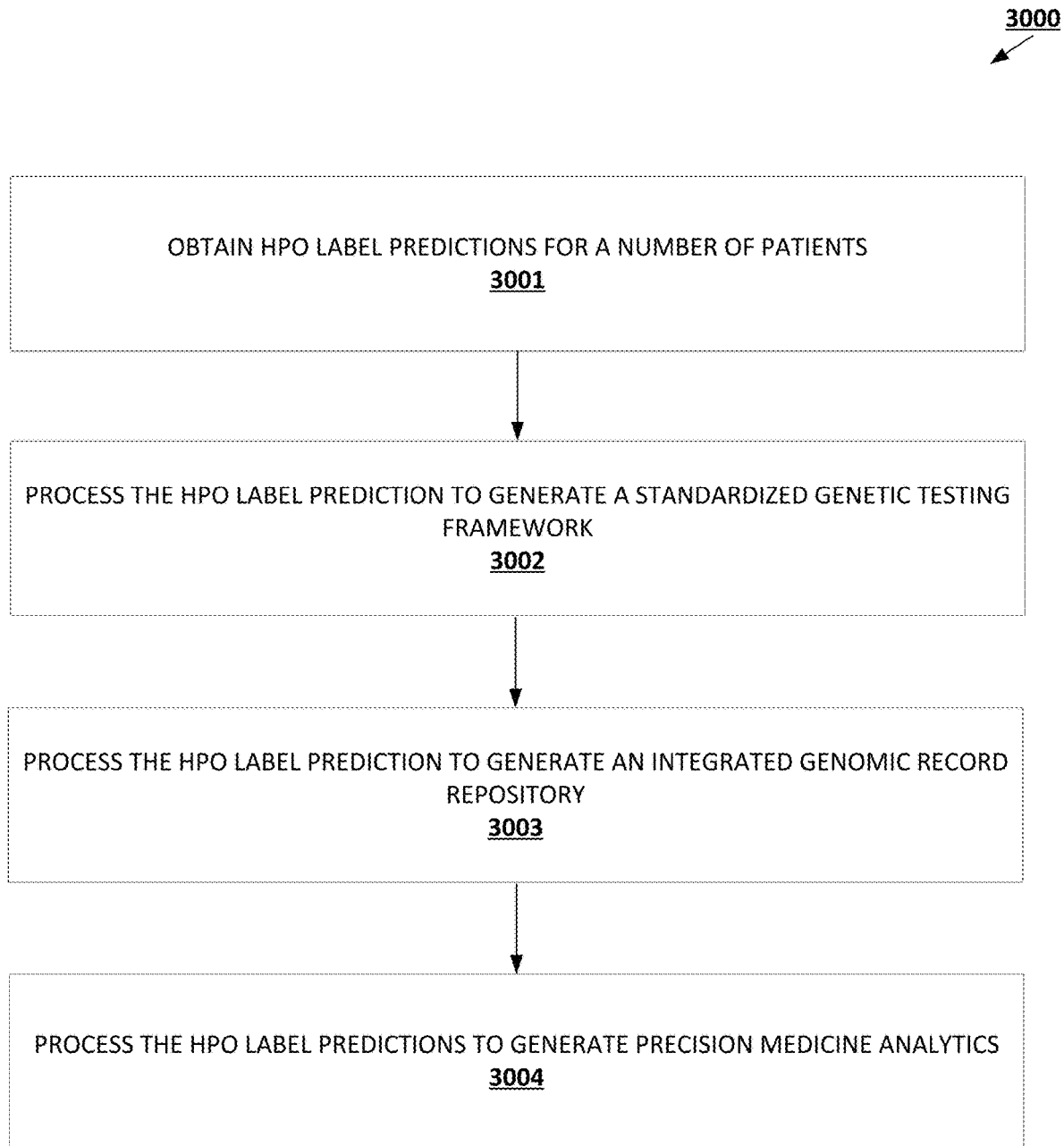

FIG. 30 is a flowchart diagram of an example process for performing HPO-based predictions in accordance with some embodiments discussed herein.

FIG. 31 provides an operational example of a patient-specific medical code record in accordance with some embodiments discussed herein.

FIG. 32 provides an operational example of a patient-specific phenotypic record in accordance with some embodiments discussed herein.

Figure 33:
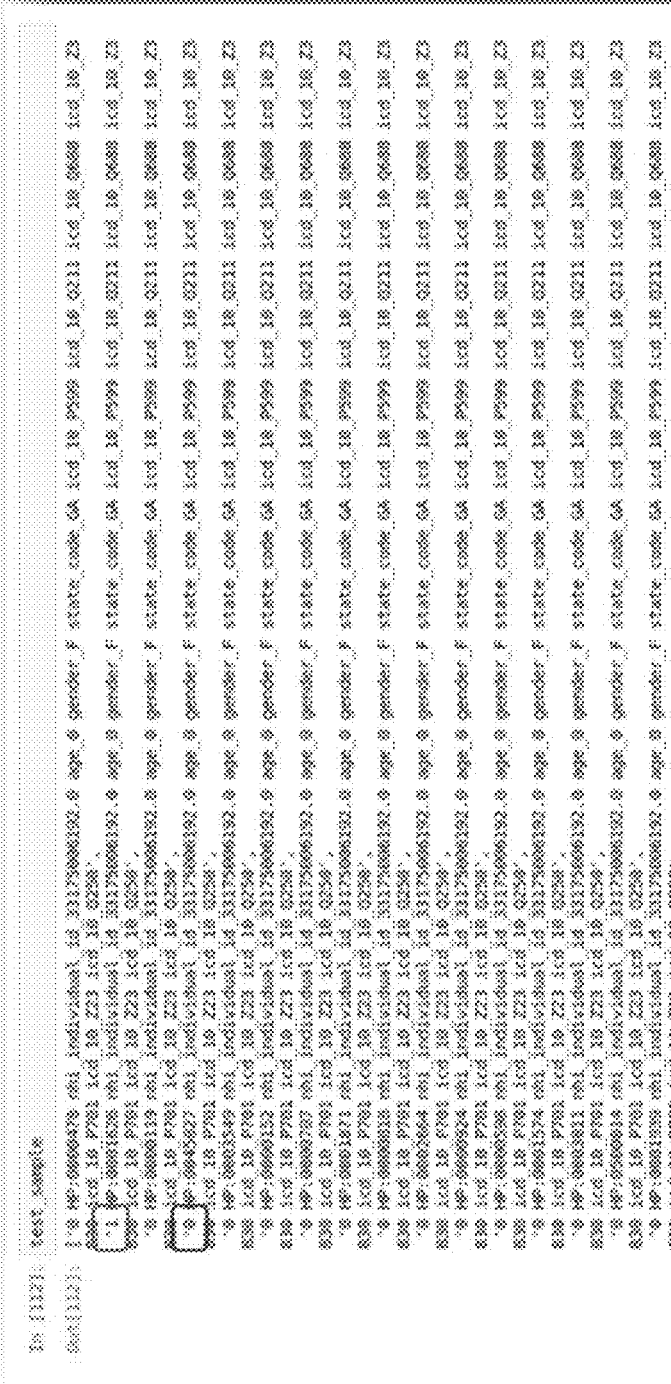

FIG. 33 provides an operational example of a cross patient holistic record in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to classification, one of ordinary skill in the art will recognize that the disclosed concepts can be used to perform other types of data analysis.

I. OVERVIEW

Discussed herein methods, apparatus, systems, computing devices, computing entities, and/or the like for classification in hierarchical prediction domains. As will be recognized, however, the disclosed concepts can be used to perform any type of predictive data analysis and/or to perform classification in non-hierarchical prediction domains.

A. Some Technical Contributions of the Present Invention

Efficient and Reliable Classification in Hierarchical Prediction Domains

A hierarchical prediction domain is a prediction domain characterized by at least one hierarchical predictive relationship. In some embodiments, a hierarchical predictive relationship between two or more prediction nodes is a relationship between the prediction nodes based on which a first prediction node has all of the attributes of each prediction node from which it is deemed to be hierarchically dependent and one or more additional attributes. For example, given the hierarchical predictive relationships C>>A and C>>B (where X>>Y denotes that prediction node Y is hierarchically dependent on the prediction node X) in a particular prediction domain, a classification system may infer that prediction nodes A and B each have all of the attributes of prediction node C in addition to one or more additional attributes.

Various embodiments of the present invention are directed to classification in a hierarchical prediction domain by using at least one of structured input data and unstructured data. Structured data may refer to data that can be divided into semantically-defined data objects based on a predefined format of the data. Examples of structured data include data defined using a Structured Query Language (SQL), data defined using a file format language (such as the JavaScript Object Notation (JSON) language, a Comma-Separated Value (CSV) language, or an Extensible Markup Language (XML) language), and/or the like. In some embodiments, structured data used to perform classification may be represented in a tabulated data format, e.g., a tabulated data format according to which rows represent entities and columns represent attributes associated with various entities. In the healthcare context, structured data may include medical claims data, which may include information associated with each medical claim (e.g., information about time of a medical operation associated with a medical claim, one or more operation codes associated with a medical claim, cost of a medical operation associated with a medical, and/or the like.) in a structured format. Unstructured data may refer to data that cannot be divided into semantically-defined data objects based on a predefined format of the data, e.g., free text data, hand-written note data, transcribed speech data, etc. Examples of unstructured data include various types of natural language data, such as medical notes data which includes medical notes provided by a medical provider.

Thus, various embodiments of the present invention relate to performing predictions related to prediction tasks characterized by a hierarchically complex prediction domain as well as a structurally complex input space. An example of a prediction task that present the complexities referred to herein is predicting HPO labels for a patient based on medical data associated with the patient, such as medical claims data associated with the patient and medical notes data associated with the medical patient. The HPO label space, which provides a standardized vocabulary of phenotypic abnormalities associated with thousands of diseases, is an example of a hierarchical prediction domain, as further described below. To perform HPO label prediction using structured medical data and unstructured medical data, there is a need for predictive analysis solutions that address the complexities associated with the HPO label space as well as the complexities associated with processing both structured medical data and unstructured medical data.

To perform predictions in a hierarchical prediction domains using structured input data and/or unstructured input data, various embodiments of the present invention propose various arrangements of one or more of the following ML models: an online ML model for processing structured input data to generate structure-based predictions, a co-occurrence analysis ML model for processing structured input data to generate structure-based predictions, a structured fusion ML model for combining structure-based predictions, and an unstructured fusion ML model for combining structure-based predictions and non-structure-based predictions. In some embodiments, at least two of the mentioned ML models are organized in an ensemble architecture to generate a final prediction based on predictions of the at least two ML models. In some embodiments, all of the mentioned ML models are organized in an ensemble architecture to generate a final prediction based on predictions of the at least two ML models.

Efficient and Reliable Online ML in Hierarchical Prediction Domains

Online learning is a method of ML in which a ML model is sequentially updated over time based on incoming training data. During training, some online learning algorithms aim to set parameters of a prediction function in a manner that minimizes measures of error between predictions and existing training data labels, including new training data labels and/or sequentially updated training data labels. For example, online learning algorithms are typically utilized to generate recommendations for a user (e.g., promotional recommendations for a user), where the user reaction to the recommendation is in turn utilized to update a ML model. In some online learning algorithms, a positive user reaction (e.g., a selection of a link corresponding to a recommendation) is used to change model parameters in a manner that increases a likelihood of future generation of the recommendation and decreases a likelihood of future generation of other recommendations, while a negative user reaction (e.g., lack of selection of a link corresponding to a recommendation) is used to change model parameters in a manner that decreases a likelihood of future generation of the recommendation and increases a likelihood of future generation of other recommendations.

Hierarchical prediction domains present unique challenges for online learning algorithms. When utilized to generate predictions related to hierarchical prediction domains, online learning algorithms should accommodate hierarchical predictive relationships between various prediction nodes in determining how to interpret incoming training data. Without applying appropriate operational adjustments that address hierarchical nature of a relevant prediction domain, online learning algorithms will require higher amounts of training data, will take longer to train, and will once trained be less accurate and reliable. Because of those challenges, various existing online learning algorithms are ill-suited for efficiently and reliably performing classification in relation to hierarchical prediction domains.

Various embodiments of the present invention address efficiency and reliability challenges related to utilizing online learning algorithms to generate predictions related to hierarchical prediction domains. According to one aspect that relates to improving efficiency and reliability of online learning in hierarchical prediction domains, various embodiments of the present invention eliminate a bias term used to penalize lack of selection of a prediction node, as hierarchical predictive relationships complicate implications of such a lack of selection for adjusting model parameters. For example, selection of a prediction node may have different implications for prediction nodes that are dependent on the particular prediction node, prediction nodes from which the particular prediction node depends, and other prediction nodes without hierarchical relationships with the particular prediction node. To address such complications, various embodiments of the present invention will not penalize lack of selection of a particular node when adjusting parameters of a relevant ML model. In doing so, various embodiments of the present invention address efficiency and reliability challenges related to utilizing online learning algorithms to generate predictions related to hierarchical prediction domains.

According to another aspect that relates to improving efficiency and reliability of online learning in hierarchical prediction domains, various embodiments of the present invention perform predictive inferences by selecting prediction nodes having sufficiently high predictive scores starting from dependent prediction nodes. In doing so, the mentioned embodiments of the present invention increase the likelihood that prediction nodes having more detailed semantic implications (e.g., more "meaningful" prediction nodes) will be selected over prediction nodes having less detailed semantic associations, thus increasing the reliability of the predictive analysis performed using online learning. For example, a prediction node associated with a thoracolumbar scoliosis HPO label will have a higher chance of selection that a prediction node associated with a scoliosis HPO label, as the former has a more meaningful semantic association than the former. This will lead to generation of structurally hierarchical predictions which have greater predictive utility. Moreover, selection of prediction labels in a hierarchical manner decreases the range of predictive scores that need to be analyzed during a predictive inference. This is because, according to various embodiments of the present invention, predictive inference will halt if a requisite number of prediction nodes are selected inmost-dependent nodes. Such techniques have the added advantage of increasing efficiency of online learning in hierarchical prediction domains by decreasing the range of prediction nodes which need to be traversed before a final prediction output is generated as part of a particular predictive inference. Thus, by selecting prediction nodes having sufficiently high predictive scores starting from dependent prediction nodes, various embodiments of the present invention address efficiency and reliability challenges related to utilizing online learning algorithms to generate predictions related to hierarchical prediction domains.

According to yet another aspect that relates to improving efficiency and reliability of online learning in hierarchical prediction domains, various embodiments of the present invention provide techniques for efficiently storing and retrieving training data. Online learning algorithms face challenges related to efficiently storing and retrieving training data during training of relevant ML models. In the absence of efficient solutions for storing and retrieving training data during training of relevant ML models, many conventional online learning algorithms are slow to train, which undermines the utility of such algorithms for predictive tasks that require real-time training and/or real-time model updates. To address such challenges, various embodiments of the present invention store training data entries in a highly sparse vector using a hashing mechanism. This aspect serves to increase efficiency and reliability of online learning in all domains, including in in hierarchical prediction domains. Thus, by storing training data entries in a highly sparse vector using a hashing mechanism, various embodiments of the present invention address efficiency and reliability challenges related to utilizing online learning algorithms to generate predictions related to hierarchical prediction domains.

Effective and Reliable Co-Occurrence Analysis in Hierarchical Prediction Domains While online ML provides important insights about relationships among hierarchical structures in a hierarchical prediction domains and has the flexibility of sequential updatability over time, other important insights can be inferred from analyzing statistical relations of particular features and particular prediction labels among training data. However, given large amounts of training data, such statistical analyses may suffer from reliability drawbacks if they do not properly accommodate for factors that complicate conceptual predictive inferences from numeric patterns. For example, trivially frequent correlations can complicate accurate and reliable conceptual inferences from statistical correlations. As another example, markedly infrequent occurrences can also complicate statistical analysis of predictive data in order to infer conceptual notions that can facilitate effective classification. As a further example, conceptually obvious correlations may distort cross-data analyses of correlations between features and prediction labels without contributing sufficient conceptual value to the predictive inference process.

Because of such complexities associated with translation of numeric patterns to conceptual predictive frameworks, many existing statistical ML problems face substantial challenges when it comes to efficiently and reliably performing predictive inferences based on co-occurrence data. To address reliability concerns stemming from complexities associated with translation of numeric patterns to conceptual predictive frameworks, many conventional statistical ML problems resort to expensive training operations that undermine efficiency of ML solutions without sufficiently contributing to the reliability and accuracy of the predictions performed by those ML solutions. Thus, there is a continuing technical need for efficient and reliable solutions for statistical ML in various classification domains, such as in hierarchical prediction domains.

Various embodiments of the present invention address the efficiency and reliability challenges related to complexities associated with translation of numeric patterns to conceptual predictive frameworks. For example, various embodiments of the present invention provide innovative solutions for both normalizing feature-label co-occurrence data and significance-based filtering of such co-occurrence data. Through the noted techniques, various embodiments of the present invention provide computationally efficient solutions that address complexities associated with translation of numeric patterns to conceptual predictive frameworks, such as complexities associated with trivially frequent co-occurrences, complexities associated with mistakenly under-recorded co-occurrences, and complexities associated with conceptually obvious co-occurrences. Accordingly, by both normalizing feature-label co-occurrence data and significance-based filtering of such co-occurrence data, various embodiments of the present invention address technical challenges related to efficiency and reliability of statistical ML solutions and improve efficiency and reliability of various existing conventional statistical ML solutions. The resulting improvements address efficiency and reliability of all statistical ML solutions, including statistical ML solutions utilized in hierarchical prediction domains. Thus, while aspects of the co-occurrence analysis ML models are described herein with respect to statistical ML solutions utilized in hierarchical prediction domains, one of ordinary skill in the art will recognize that the co-occurrence analysis ML models can be utilized to improve efficiency and reliability of all statistical ML solutions, including statistical ML solutions utilized in non-hierarchical prediction domains.

In addition to improving efficiency and reliability of all statistical ML solutions, some aspects of the co-occurrence analysis ML models described herein include important contributions to efficiency and reliability of ML in hierarchical prediction domains. In hierarchical prediction domains, the presence of hierarchical relationships between prediction nodes in the output space complicates the task of inferring a prediction output based on prediction scores for various prediction nodes. On the one hand, the hierarchical relationships between prediction nodes in the output space provide important domain information that can facilitate efficient and reliable predictive inferences. On the other hand, important predictive conclusions may be inferred from ignoring the hierarchical relationships, especially in instances where the available hierarchical models do not capture all of the relevant information about conceptual relationships between prediction nodes and/or include potentially erroneous information about conceptual relationships between prediction nodes. Thus, there is a continuing technical challenge associated with performing predictive analyses in a manner that takes into account both hierarchical composition of the output space and cross-hierarchical composition of the output space.

Various embodiments of the present invention address the mentioned technical challenges associated with considering both hierarchical composition of the output space and cross-hierarchical composition of the output space when performing classification in hierarchical prediction domains. For example, various embodiments of the present invention relate to co-occurrence analysis ML models that generate structurally non-hierarchical predictions. A structurally non-hierarchical prediction may be a prediction determined without regard to a position of the corresponding prediction node in a structural hierarchy characterizing the hierarchical prediction domain that includes the corresponding prediction node. For example, in some embodiments, a co-occurrence analysis ML model may be configured to generate the one or more co-occurrence analysis predictions based on prediction values for prediction nodes regardless of whether the prediction nodes are deemed to be dependent prediction nodes in a structurally hierarchy characterizing the prediction domain associated with the co-occurrence analysis ML model. In at least some of those embodiments, the co-occurrence analysis ML model may generate predictions that correspond to both most-dependent nodes and non-most-dependent nodes in the structural hierarchically characterizing the prediction domain associated with the online ML model.

By generating structurally non-hierarchical predictions, various embodiments of the present invention provide predictions that are agnostic to the hierarchical composition of the prediction output space. When used in combination and/or in fusion with structurally hierarchical predictions (e.g., online learning predictions generated by an online ML model), such predictions can provide important cross-hierarchical conceptual inferences that can in turn facilitate efficient and effective classification in conceptually hierarchical domains. Thus, by generating structurally non-hierarchical predictions that can in turn be used in combination and/or in fusion with structurally hierarchical predictions, various embodiments of the present invention address technical challenges related to accounting for both hierarchical composition of the output space and cross-hierarchical composition of the output space when performing classification in hierarchical prediction domains. In doing so, various embodiments of the present invention make important technical contributions to efficiency and reliability of classification in hierarchical prediction domains, such as in classification in an HPO prediction domain.

Efficient and Reliable Fusion of Structurally Hierarchical Predictions and Structurally Non-Hierarchical Predictions As discussed above with reference to co-occurrence analysis ML models, in hierarchical prediction domains, the presence of hierarchical relationships between prediction nodes in the output space complicates the task of inferring a prediction output based on prediction scores for various prediction nodes. On the one hand, the hierarchical relationships between prediction nodes in the output space provide important domain information that can facilitate efficient and reliable predictive inferences. On the other hand, important predictive conclusions may be inferred from ignoring the hierarchical relationships, especially in instances where the available hierarchical models do not capture all of the relevant information about conceptual relationships between prediction nodes and/or include potentially erroneous information about conceptual relationships between prediction nodes. Thus, there is a continuing technical challenge associated with performing predictive analyses in a manner that considers both hierarchical composition of the output space and cross-hierarchical composition of the output space.

Various embodiments of the present invention address the mentioned technical challenges associated with considering both hierarchical composition of the output space and cross-hierarchical composition of the output space when performing classification in hierarchical prediction domains. For example, various embodiments of the present invention relate to co-occurrence analysis ML models that generate structurally non-hierarchical predictions. A structurally non-hierarchical prediction may be a prediction determined without regard to a position of the corresponding prediction node in a structural hierarchy characterizing the hierarchical prediction domain that includes the corresponding prediction node. For example, in some embodiments, a co-occurrence analysis ML model may be configured to generate the one or more co-occurrence analysis predictions based on prediction values for prediction nodes regardless of whether the prediction nodes are deemed to be dependent prediction nodes in a structurally hierarchy characterizing the prediction domain associated with the co-occurrence analysis ML model. In at least some of those embodiments, the co-occurrence analysis ML model may generate predictions that correspond to both most-dependent nodes and non-most-dependent nodes in the structural hierarchically characterizing the prediction domain associated with the online ML model.

By generating structurally non-hierarchical predictions, various embodiments of the present invention provide predictions that are agnostic to the hierarchical composition of the prediction output space. Such structurally non-hierarchical predictions can in turn be used in combination and/or in fusion with structurally hierarchical predictions, such as structurally hierarchical predictions generated by an online learning unit 111. When structurally non-hierarchical predictions are used in combination and/or in fusion with structurally hierarchical predictions to generate structure-based predictions, such structured-fused predictions can provide important cross-hierarchical conceptual inferences that can in turn facilitate efficient and effective classification in conceptually hierarchical domains. Various embodiments of the present invention provide efficient and reliable techniques for fusing structurally hierarchical predictions and structurally non-hierarchical predictions. Such solutions make important technical contributions to classification models in hierarchical prediction domains, as they enable such models to utilize both predictive insights provided by hierarchical relationships of the output space and predictive insights provided without taking hierarchical relationships among training data into account. In doing so, various embodiments of the present invention address key challenges related to efficiency and reliability of classification in hierarchical prediction domains, such as the efficiency and reliability of HPO label prediction.

Efficient and Reliable Fusion of Structure-Based Predictions and Non-Structure-Based Predictions Various embodiments of the present invention are directed to classification in a hierarchical prediction domain by using at least one of structured input data and unstructured data. Structured data may refer to data that can be divided into semantically-defined data objects based on a predefined format of the data. Examples of structured data include data defined using a Structured Query Language (SQL), data defined using a file format language (such as the JavaScript Object Notation (JSON) language, a Comma-Separated Value (CSV) language, or an Extensible Markup Language (XML) language), and/or the like. In some embodiments, structured data used to perform classification may be represented in a tabulated data format, e.g., a tabulated data format according to which rows represent entities and columns represent attributes associated with various entities. In the healthcare context, structured data may include medical claims data, which may include information associated with each medical claim (e.g., information about time of a medical operation associated with a medical claim, one or more operation codes associated with a medical claim, cost of a medical operation associated with a medical, and/or the like.) in a structured format. Unstructured data may refer to data that cannot be divided into semantically-defined data objects based on a predefined format of the data, e.g., handwritten note data, transcribed speech data, image data, etc. Examples of unstructured data include various types of natural language data, such as medical notes data which includes medical notes provided by a medical provider.

Both structured data and unstructured data provide valuable predictive insights for predictive analysis tasks, e.g., for predictive analysis tasks related to hierarchical prediction domains. For example, structured data can provide important insights about statistical distribution of features and prediction labels as well as sequential change of correlations between features and prediction labels over time. In some cases, structured data can provide insights that are out of the reach of semantically-unsophisticated and/or primarily-lexical natural language processing algorithms for processing unstructured data. On the other hand, when properly analyzed (e.g., when analyzed using semantically-sophisticated synonym-based natural language processing algorithms), unstructured data can provide a strong source of predictive insights about a predictive task associated with a hierarchical prediction domain.

Despite the complimentary utility of structured data and unstructured data in providing predictive insights relevant to classification in hierarchical prediction domains, the problem of efficiently and effectively integrating predictions derived from structured data (e.g., structure-based predictions) and predictions derived from unstructured data (e.g., non-structure-based predictions) is a non-trivial problem from a technical standpoint. Indeed, many conventional classification solutions fail to efficiently and reliably integrate structure-based predictions and non-structure-based predictions to generate predictive outputs. For example, a naive combination of particular structure-based predictions and non-structure-based predictions fails to properly appreciate the reciprocal implications of structure-based predictions and non-structure-based predictions for improving models utilized to generate each other. Indeed, one innovative aspect of the present invention relates to techniques for efficiently and reliably integrating structure-based predictions and non-structure-based predictions in a manner that causes at least one of the noted sets of predictions to provide feedback to a model utilized to generate the other.

Accordingly, various embodiments of the present invention address technical challenges related to efficient and reliable fusion of structure-based predictions and non-structure-based predictions by utilizing at least one of the noted sets of predictions to provide feedback to a model utilized to generate the other. For example, in some embodiments, non-structure-based predictions are used as ground-truth data to retrain one or more ML models utilized to generate structure-based predictions, e.g., one or more of an online ML model and a co-occurrence analysis ML model. Through this and similar techniques, various embodiments of the present invention enable feedback-loop mechanism relationships between structure-based predictions and non-structure-based predictions which serve to render the models utilized to generate at least one of the structure-based predictions and the non-structure-based predictions more efficient (both in terms of training efficiency and in terms of inference efficiency) as well as more reliable. Thus, by utilizing at least one of the noted sets of predictions to provide feedback to a model utilized to generate the other, various embodiments of the present invention address technical challenges related to efficient and reliable fusion of structure-based predictions and non-structure-based predictions and make substantial technical improvements to conventional solutions for classification, such as conventional solutions for classification in hierarchical prediction domains.

Efficient and Reliable HPO Label Prediction

HPO label prediction is an example of a prediction task related to a hierarchical prediction domain. As discussed above and further described below, the hierarchical prediction domains such as the HPO label domain present significant problems for various classification approaches. Examples of these challenges include challenges associated with structural complexity of the output space of such hierarchical prediction domains as well as challenges associated with complexity of input space of hierarchical prediction domains. Accordingly, to perform HPO label prediction using structured medical data and unstructured medical data, there is a need for predictive analysis solutions that address the complexities associated with the HPO label space as well as the complexities associated with processing both structured medical data and unstructured medical data.

To perform predictions in a hierarchical prediction domains using structured input data and/or unstructured input data, various embodiments of the present invention propose various arrangements of one or more of the following ML models: an online ML model for processing structured input data to generate structure-based predictions, a co-occurrence analysis ML model for processing structured input data to generate structure-based predictions, a structured fusion ML model for combining structure-based predictions, and an unstructured fusion ML model for combining structure-based predictions and non-structure-based predictions. In some embodiments, at least two of the mentioned ML models are organized in an ensemble architecture to generate a final prediction based on predictions of the at least two ML models. In some embodiments, all of the mentioned ML models are organized in an ensemble architecture to generate a final prediction based on predictions of the at least two ML models. Such ensemble architectures provide efficient and reliable solutions for classification in hierarchical prediction domain, such as for HPO label prediction in relation to the HPO label domain.

In addition, hierarchical prediction domains like the HPO domain present unique challenges for online learning algorithms. When utilized to generate predictions related to hierarchical prediction domains, online learning algorithms should accommodate hierarchical predictive relationships between various prediction nodes in determining how to interpret incoming training data. Without applying appropriate operational adjustments that address hierarchical nature of a relevant prediction domain, online learning algorithms will require higher amounts of training data, will take longer to train, and will once trained be less accurate and reliable. Because of those challenges, various existing online learning algorithms are ill-suited for efficiently and reliably performing classification in relation to hierarchical prediction domains.

Various embodiments of the present invention address efficiency and reliability challenges related to utilizing online learning algorithms to generate predictions related to hierarchical prediction domains. According to one aspect that relates to improving efficiency and reliability of online learning in hierarchical prediction domains, various embodiments of the present invention eliminate a bias term used to penalize lack of selection of a prediction node, as hierarchical predictive relationships complicate implications of such a lack of selection for adjusting model parameters. For example, selection of a prediction node may have different implications for prediction nodes that are dependent on the particular prediction node, prediction nodes from which the particular prediction node depends, and other prediction nodes without hierarchical relationships with the particular prediction node. To address such complications, various embodiments of the present invention will not penalize lack of selection of a particular node when adjusting parameters of a relevant ML model. In doing so, various embodiments of the present invention address efficiency and reliability challenges related to utilizing online learning algorithms to generate predictions related to hierarchical prediction domains, such generating HPO label predictions related to the HPO label domain.

Next, some aspects of the co-occurrence analysis ML models described herein include important contributions to efficiency and reliability of ML in hierarchical prediction domains, such as the HPO prediction domain. In hierarchical prediction domains, the presence of hierarchical relationships between prediction nodes in the output space complicates the task of inferring a prediction output based on prediction scores for various prediction nodes. On the one hand, the hierarchical relationships between prediction nodes in the output space provide important domain information that can facilitate efficient and reliable predictive inferences. On the other hand, important predictive conclusions may be inferred from ignoring the hierarchical relationships, especially in instances where the available hierarchical models do not capture all of the relevant information about conceptual relationships between prediction nodes and/or include potentially erroneous information about conceptual relationships between prediction nodes.

Thus, there is a continuing technical challenge associated with performing predictive analyses in a manner that takes into account both hierarchical composition of the output space and cross-hierarchical composition of the output space.

Various embodiments of the present invention address the mentioned technical challenges associated with considering both hierarchical composition of the output space and cross-hierarchical composition of the output space when performing classification in hierarchical prediction domains. For example, various embodiments of the present invention relate to co-occurrence analysis ML models that generate structurally non-hierarchical predictions. A structurally non-hierarchical prediction may be a prediction determined without regard to a position of the corresponding prediction node in a structural hierarchy characterizing the hierarchical prediction domain that includes the corresponding prediction node. By generating structurally non-hierarchical predictions, various embodiments of the present invention provide predictions that are agnostic to the hierarchical composition of the prediction output space. When used in combination and/or in fusion with structurally hierarchical predictions (e.g., online learning predictions generated by an online ML model), such predictions can provide important cross-hierarchical conceptual inferences that can in turn facilitate efficient and effective classification in conceptually hierarchical domains. Thus, by generating structurally non-hierarchical predictions that can in turn be used in combination and/or in fusion with structurally hierarchical predictions, various embodiments of the present invention address technical challenges related to accounting for both hierarchical composition of the output space and cross-hierarchical composition of the output space when performing classification in hierarchical prediction domains. In doing so, various embodiments of the present invention make important technical contributions to efficiency and reliability of classification in hierarchical prediction domains, such as in classification in an HPO prediction domain and with respect to the HPO label prediction predictive task.

Furthermore, hierarchical prediction domains like the HPO prediction domain present challenges related to fusion of structurally hierarchical predictions and non-structurally hierarchical predictions. By generating structurally non-hierarchical predictions, various embodiments of the present invention provide predictions that are agnostic to the hierarchical composition of the prediction output space. Such structurally non-hierarchical predictions can in turn be used in combination and/or in fusion with structurally hierarchical predictions, such as structurally hierarchical predictions generated by an online learning unit 111. When structurally non-hierarchical predictions are used in combination and/or in fusion with structurally hierarchical predictions are used to generate structure-based predictions, such structured-fused predictions can provide important cross-hierarchical conceptual inferences that can in turn facilitate efficient and effective classification in conceptually hierarchical domains.

Various embodiments of the present invention provide efficient and reliable techniques for fusing structurally hierarchical predictions and structurally non-hierarchical predictions. Such solutions make important technical contributions to classification models in hierarchical prediction domains, as they enable such models to utilize both predictive insights provided by hierarchical relationships of the output space and predictive insights provided without taking hierarchical relationships among training data into account. In doing so, various embodiments of the present invention address key challenges related to efficiency and reliability of classification in hierarchical prediction domains, such as the efficiency and reliability of HPO label prediction.

Moreover, hierarchical prediction domains like the HPO domain present challenges related to fusion of structure-based predictions and non-structure-based predictions. Both structured data and unstructured data provide valuable predictive insights for predictive analysis tasks, e.g., for predictive analysis tasks related to hierarchical prediction domains. However, despite the complimentary utility of structured data and unstructured data in providing predictive insights relevant to classification in hierarchical prediction domains, the problem of efficiently and effectively integrating predictions derived from structured data (i.e., structure-based predictions) and predictions derived from unstructured data (i.e., non-structure-based predictions) is a non-trivial problem from a technical standpoint. Indeed, many conventional classification solutions fail to efficiently and reliably integrate structure-based predictions and non-structure-based predictions to generate predictive outputs. For example, a naive combination of particular structure-based predictions and non-structure-based predictions fails to properly appreciate the reciprocal implications of structure-based predictions and non-structure-based predictions for improving models utilized to generate each other. Indeed, one innovative aspect of the present invention relates to techniques for efficiently and reliably integrating structure-based predictions and non-structure-based predictions in a manner that causes at least one of the noted sets of predictions to provide feedback to a model utilized to generate the other.

Accordingly, various embodiments of the present invention address technical challenges related to efficient and reliable fusion of structure-based predictions and non-structure-based predictions by utilizing at least one of the noted sets of predictions to provide feedback to a model utilized to generate the other. For example, in some embodiments, non-structure-based predictions are used as ground-truth data to retrain one or more ML models utilized to generate structure-based predictions, e.g., one or more of an online ML model and a co-occurrence analysis ML model. Through this and similar techniques, various embodiments of the present invention enable feedback-loop mechanism relationships between structure-based predictions and non-structure-based predictions which serve to render the models utilized to generate at least one of the structure-based predictions and the non-structure-based predictions more efficient (both in terms of training efficiency and in terms of inference efficiency) as well as more reliable. Thus, by utilizing at least one of the noted sets of predictions to provide feedback to a model utilized to generate the other, various embodiments of the present invention address technical challenges related to efficient and reliable fusion of structure-based predictions and non-structure-based predictions and make substantial technical improvements to conventional solutions for classification, such as conventional solutions for classification in hierarchical prediction domains.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

The architecture 100 includes one or more external computing entities 102 that interact with a classification system 101 via a communication network (not shown). The classification system 101 includes a storage subsystem 108 and a classification computing entity 106. Each computing entity, computing subsystem, and/or computing system in the architecture 100 may include any suitable network server and/or other type of processing device. The communication network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

In some embodiments, the architecture 100 is configured to enable the external computing entities 102 to provide prediction inputs to the classification system 101 and, in response, receive predictions generated based on the prediction inputs. For example, a particular external computing entity 102 may provide a request for an HPO label prediction for a patient, where the request may include data associated with the patient (e.g., personal attribute data associated with the patient, medical codes associated with the medical history of the patient, and/or the like.). The classification system 101 is configured to generate the requested HPO label predictions and provide the generated HPO label predictions to the particular external computing entity 102.

The classification computing entity 106 includes a model generation unit 115 configured to train at least one ML model utilized by the classification computing entity 106 to perform predictions. Examples of models trained by the model generation unit 115 may include an online ML model and a co-occurrence analysis ML model. The classification computing entity 106 further includes an online learning unit 111 configured to apply the online ML model to a particular prediction input to generate a corresponding co-occurrence analysis prediction.

In some embodiments, at least some of the ML models utilized by the classification computing entity 106 to perform predictions may produce structurally hierarchical predictions while at least some other ML models utilized by the classification computing entity 106 to perform predictions may produce non-structurally hierarchical predictions. In some of those embodiments, a structured fusion unit 113 of the classification computing entity 106 is configured to combine at least one structurally hierarchical prediction and at least one structurally non-hierarchical prediction to generate a structure-based prediction.

In some embodiments, at least some of the ML models utilized by the classification computing entity 106 to perform predictions may utilize structured data to produce structure-based predictions, while at least some other ML models utilized by the classification computing entity 106 to perform predictions may utilize unstructured data to produce non-structure-based predictions. In some of those embodiments, an unstructured fusion unit 114 of the classification computing entity 106 is configured to combine at least one structure-based prediction and at least one non-structure-based prediction to generate an unstructured-fused prediction.

The classification computing entity 106 may further include a system interaction unit 116 configured to generate predictions based on at least one of the ML models utilized by the classification computing entity 106, for example based on at least one of the online ML model, the co-occurrence analysis ML model, the structured fusion ML model, and the unstructured fusion ML model. In some embodiments, the system interaction unit 116 is configured to utilize one or more ML models to generate HPO labels. In some of those embodiments, the system interaction unit 116 is further configured to generate HPO-based predictions and/or HPO-based data reports, such as standardized genomic testing frameworks, integrated genomic record repositories, and precision medicine analytics. In some embodiments, the system interaction unit 116 is configured to perform one or more actions (e.g., transmission of communications, activation of alerts, automatic scheduling of appointments, and/or the like.) based on the predicted HPO labels and/or based on the generated HPO-based predictions.

The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The storage subsystem 108 may include structured input data 121, unstructured input data 122, model definition data 123 (e.g., data defining at least one parameter and/or at least one hyper-parameter of at least one ML model utilized by the classification computing entity 106), and raw training data 124 (e.g., data utilized by the model generation unit 115 to train at least one ML model utilized by the classification computing entity 106, such as hierarchically non-expanded data utilized by the model generation unit 115 to train at least one ML model utilized by the classification computing entity 106).

B. Exemplary Classification Computing Entity

FIG. 2 provides a schematic of a classification computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the classification computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the classification computing entity 106 may include or be in communication with one or more processing elements 205 (also referred to as processors, processing circuitry, and/or similar terms used herein interchangeably) that communicate with other elements within the classification computing entity 106 via a bus, for example. As will be understood, the processing element 205 may be embodied in a number of different ways. For example, the processing element 205 may be embodied as one or more Complex Pogrammable Logic Devices (CPLDs), microprocessors, multi-core processors, coprocessing entities, Application-Specific Instruction-Set Processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, Application Specific Integrated Circuits (ASICs), Field Programmable Gate Arrays (FPGAs), Programmable Logic Arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the classification computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the classification computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the classification computing entity 106 with the assistance of the processing element 205 and operating system.

As indicated, in one embodiment, the classification computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the classification computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the classification computing entity 106 may include or be in communication with one or more input elements, such as a keyboard input, a mouse input, a touch screen/display input, motion input, movement input, audio input, pointing device input, joystick input, keypad input, and/or the like. The classification computing entity 106 may also include or be in communication with one or more output elements (not shown), such as audio output, video output, screen/display output, motion output, movement output, and/or the like.

C. Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the classification computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the classification computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the classification computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the classification computing entity 106 and/or various other computing entities.

In another embodiment, the external computing entity 102 may include one or more components or functionality that are the same or similar to those of the classification computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. EXEMPLARY SYSTEM OPERATION

The operation of various embodiments of the present invention will now be described. As discussed herein, various embodiments are directed to systems and methods for classification in hierarchical prediction domains. Various embodiments of the disclosed techniques enable classification in hierarchical prediction domains by using at least one of online ML in hierarchical prediction domains, co-occurrence analysis in hierarchical prediction domains, fusion of structurally hierarchical predictions and structurally non-hierarchical predictions in in hierarchical prediction domains, fusion of structure-based predictions and non-structure-based predictions in hierarchical prediction domains, and HPO predictions in the hierarchical HPO label domain.

A. Classification in a Hierarchical Prediction domain

Various embodiments of the present invention are directed to classification in a hierarchical prediction domain by using at least one of structured input data and unstructured data. Structured data may refer to data that can be divided into semantically-defined data objects based on a predefined format of the data. Examples of structured data include data defined using a Structured Query Language (SQL), data defined using a file format language (such as the JavaScript Object Notation (JSON) language, a Comma-Separated Value (CSV) language, or an Extensible Markup Language (XML) language), and/or the like. In the healthcare context, structured data may include medical claims data, which may include information associated with each medical claim (e.g., information about time of a medical operation associated with a medical claim, one or more operation codes associated with a medical claim, cost of a medical operation associated with a medical, and/or the like.) in a structured format. Unstructured data may refer to data that cannot be divided into semantically-defined data objects based on a predefined format of the data. Examples of unstructured data include various types of natural language data, such as medical notes data which includes medical notes provided by a medical provider. Although various solutions exist for inferring semantically-defined data objects from unstructured data (such as various natural language processing solutions), such an inference is distinct from a straightforward division of structured data into semantically-defined data objects based on a predefined format of the structured data.

Thus, various embodiments of the present invention relate to performing predictions related to prediction tasks characterized by a hierarchically complex prediction domain as well as a structurally complex input space. An example of a prediction task that present the complexities referred to herein is predicting HPO labels for a patient based on medical data associated with the patient, such as medical claims data associated with the patient and medical notes data associated with the medical patient. The HPO label space, which provides a standardized vocabulary of phenotypic abnormalities associated with thousands of diseases, is an example of a hierarchical prediction domain, as further described below. To perform HPO label prediction using structured medical data and unstructured medical data, there is a need for predictive analysis solutions that address the complexities associated with the HPO label space as well as the complexities associated with processing both structured medical data and unstructured medical data.

To perform predictions in a hierarchical prediction domains using structured input data and/or unstructured input data, various embodiments of the present invention propose various arrangements of one or more of the following ML models: an online ML model for processing structured input data to generate structure-based predictions, a co-occurrence analysis ML model for processing structured input data to generate structure-based predictions, a structured fusion ML model for combining structure-based predictions, and an unstructured fusion ML model for combining structure-based predictions and non-structure-based predictions. In some embodiments, at least two of the mentioned ML models are organized in an ensemble architecture to generate a final prediction based on predictions of the at least two ML models. In some embodiments, all of the mentioned ML models are organized in an ensemble architecture to generate a final prediction based on predictions of the at least two ML models.

FIGS. 4A and 4B depict two example ensemble architectures utilizing all of the four above-mentioned ML models. However, a person of ordinary skill in the art will recognize that the four mentioned ML models can be utilized individually or in any particular combination of two or more of the four mentioned ML models. Furthermore, a person of ordinary skill in the art will recognize that, if two or more ML models are utilized to generate a prediction (e.g., all four mentioned ML models are utilized to generate a prediction), the four ML models may be organized in accordance with any ensemble architecture, including an ensemble architecture that is different from either or both of the ensemble architectures depicted in FIGS. 4A and 4B. Moreover, a person of ordinary skill in the art will recognize that one or more of each of the four mentioned ML models may be utilized in combination of one or more other ML models in accordance with various ensemble architectures to generate a multi-model prediction framework. Thus, the depiction of example ensemble architectures in FIGS. 4A and 4B, and the accompanying description of the noted example ensemble architectures provided herein, is not meant to be limiting as to the scope of the present invention.

FIG. 4A is an operational flow diagram for an ensemble architecture 410 with an online ML model for processing structured input data, a co-occurrence analysis ML model for processing structured input data, a structured fusion ML model for combining structure-based predictions, and an unstructured fusion ML model for combining structure-based predictions and non-structure-based predictions, where the ensemble architecture 410 performs a structured fusion before performing an unstructured fusion. As depicted in the ensemble architecture 410, the online learning unit 111 retrieves the structured input data 121 from the storage subsystem and processes the structured input data 121 in accordance with an online ML model to generate one or more online learning predictions. Moreover, the co-occurrence analysis unit 112 retrieves the structured input data 121 from the storage subsystem and processes the structured input data 121 in accordance with a co-occurrence analysis ML model to generate one or more co-occurrence analysis predictions. In some embodiments, both the one or more online learning predictions and the one or more co-occurrence analysis predictions are structure-based predictions, i.e., predictions generated based on structured input data.

In some embodiments, to generate the one or more online learning predictions, the online learning unit 111 processes the structured input data 121 in accordance with an online ML model. The online ML model may be a ML model that utilizes sequential updates to a ML model in order to infer a relationship between a prediction input space and a prediction output space. For example, the online ML model may be an online ML model that utilizes structured medical claim data to generate one or more HPO label predictions. An example of such an online ML model may be a ML model that utilizes an FTRL ML algorithm. In some embodiments, the one or more online learning predictions may be structurally hierarchical predictions. A structurally hierarchical prediction may be a prediction determined based at least in part on a position of a corresponding prediction node in a structural hierarchy characterizing the hierarchical prediction domain that includes the corresponding prediction node. For example, in some embodiments, an online ML model may be configured to generate the one or more online learning predictions based on prediction values for prediction nodes deemed to be most-dependent prediction nodes in a structurally hierarchy characterizing the prediction domain associated with the online ML model. In at least some of those embodiments, the online ML model will not generate predictions that correspond to non-most-dependent nodes in the structural hierarchically characterizing the prediction domain associated with the online ML model.

In some embodiments, to generate the one or more co-occurrence analysis predictions, the co-occurrence analysis unit 112 processes the structured input data 121 in accordance with a co-occurrence analysis ML model. The co-occurrence analysis ML model may be a ML model that infers one or more statistical relationships based on co-occurrences of particular prediction input values (e.g., medical codes in medical claims data, such as medical codes corresponding to the 10th Revision of the International Classification of Diseases Procedure Classification System (ICD-10-PCS) and/or medical codes corresponding to the 10th Revision of the International Classification of Diseases Clinical Modification (ICD-10-CM) system) and particular prediction output values (e.g., HPO labels). In some embodiments, the one or more co-occurrence analysis predictions may be structurally non-hierarchical predictions. A structurally non-hierarchical prediction may be a prediction determined without regard to a position of the corresponding prediction node in a structural hierarchy characterizing the hierarchical prediction domain that includes the corresponding prediction node. For example, in some embodiments, a co-occurrence analysis ML model may be configured to generate the one or more co-occurrence analysis predictions based on prediction values for prediction nodes regardless of whether the prediction nodes are deemed to be dependent prediction nodes in a structurally hierarchy characterizing the prediction domain associated with the co-occurrence analysis ML model. In at least some of those embodiments, the co-occurrence analysis ML model may generate predictions that correspond to both most-dependent nodes and non-most-dependent nodes in the structural hierarchically characterizing the prediction domain associated with the online ML model.

Returning to FIG. 4A, the ensemble architecture 410 further includes processing the online learning predictions generated by the online learning unit 111 and the co-occurrence analysis predictions generated by the co-occurrence analysis unit 112 using the structured fusion unit 113 to generate one or more structured fusion predictions. To process the online learning predictions generated by the online learning unit 111 and the co-occurrence analysis predictions generated by the co-occurrence analysis unit 112 to generate one or more structured fusion predictions, the structured fusion unit 113 may utilize a structured fusion ML model. The structured fusion ML model may be a ML model configured to generate/predict one or more structured fusion predictions based on unfused predictions generated by two or more unfused ML models, where the unfused predictions include at least one prediction generated by a ML model configured to generate/predict structurally hierarchical predictions and at least one prediction generated by a ML model configured to generate/predict structurally non-hierarchical predictions. In the particular ensemble architecture 410 depicted in FIG. 4A, the structured fusion ML model utilized by the structured fusion unit 113 is configured to generate one or more structured fusion predictions based on unfused predictions generated by two or more unfused ML models: structurally hierarchical predictions (i.e., the one or more online learning predictions) generated by the online ML model utilized by the online learning unit 111 and structurally non-hierarchical predictions (i.e., the one or more co-occurrence analysis predictions) generated by the co-occurrence analysis ML model utilized by the co-occurrence analysis unit 112. While the particular ensemble architecture 410 depicted in FIG. 4A includes a structured fusion unit 113 configured to process structure-based predictions (i.e., the one or more online learning predictions and the one or more co-occurrence analysis predictions, both of which are determined based on the structured input data 121), a person of ordinary skill in the art will recognize that the structured fusion ML model utilized by the structured fusion unit 113 may be configured to process structurally hierarchical predictions determined based on unstructured input data and/or structurally non-hierarchical predictions determined based on unstructured input data.

Returning to FIG. 4A, the ensemble architecture 410 further includes processing the one or more structured fusion predictions generated by the structured fusion unit 113 with one or more non-structure-based predictions determined based on the unstructured input data 122 using the unstructured fusion unit 114 to generate one or more final predictions 401. To process the one or more structured-fusion predictions generated by the structured fusion unit 113 with one or more non-structure-based predictions determined based on the unstructured input data 122 in order to generate one or more final predictions 401, the unstructured fusion unit 114 may utilize an unstructured fusion ML model. The unstructured fusion ML model may be a ML model configured to generate/predict one or more unstructured-fused predictions based on unfused predictions generated by two or more unfused ML models, where the unfused predictions include at least one prediction generated by a ML model configured to generate/predict structure-based predictions and at least one prediction generated by a ML model configured to generate/predict non-structure-based predictions. In some embodiments, a structure-based prediction is a prediction determined based on structured input data, while a non-structure-based prediction is a prediction determined based on unstructured input data.

In the particular ensemble architecture 410 depicted in FIG. 4A, the unstructured fusion ML model utilized by the unstructured fusion unit 114 is configured to generate unstructured-fused predictions based on structured-fused predictions generated by the structured fusion unit 113 and non-structure-based predictions generated based on the unstructured input data 122 stored in the storage subsystem 108. However, a person of ordinary skill in the art will recognize that the unstructured fusion ML model utilized by the unstructured fusion unit 114 may be configured to process any combination of structure-based predictions and non-structure-based predictions. In some embodiments, the unstructured fusion unit 114 is further configured to perform natural language processing on the unstructured input data 122 to generate unfused non-structure-based predictions based on the unstructured input data 122, while in other embodiments the unstructured input data 122 includes predetermined unfused non-structure-based predictions determined based on particular natural language input data (e.g., feature data extracted from medical notes data using a synonym-based natural language processing analysis).

FIG. 4B is an operational flow diagram for an ensemble architecture 450 with an online ML model for processing structured input data, a co-occurrence analysis ML model for processing structured input data, a structured fusion ML model for combining structure-based predictions, and an unstructured fusion ML model for combining structure-based predictions and non-structure-based predictions, where the ensemble architecture 410 performs an unstructured fusion before performing a structured fusion. As depicted in the ensemble architecture 450, the co-occurrence analysis unit 112 retrieves the structured input data 121 from the storage subsystem and processes the structured input data 121 in accordance with a co-occurrence analysis ML model to generate one or more co-occurrence analysis predictions.

In some embodiments, to generate the one or more co-occurrence analysis predictions, the co-occurrence analysis unit 112 processes the structured input data 121 in accordance with a co-occurrence analysis ML model. The co-occurrence analysis ML model may be a ML model that infers one or more statistical relationships based on co-occurrences of particular prediction input values (e.g., medical codes in medical claims data, such as medical codes corresponding to the ICD-10-PCS and/or ICD-10-CM systems) and particular prediction output values (e.g., HPO labels). In some embodiments, the one or more co-occurrence analysis predictions may be structurally non-hierarchical predictions. For example, in some embodiments, a co-occurrence analysis ML model may be configured to generate the one or more co-occurrence analysis predictions based on prediction values for prediction nodes regardless of whether the prediction nodes are deemed to be dependent prediction nodes in a structurally hierarchy characterizing the prediction domain associated with the co-occurrence analysis ML model.

Returning to FIG. 4B, the ensemble architecture 450 further includes processing the one or more co-occurrence analysis predictions generated by the co-occurrence analysis unit 112 and one or more non-structure-based predictions generated based on the unstructured input data 122 using the unstructured fusion unit 114 to generate one or more unstructured-fused predictions. To process the one or more co-occurrence analysis predictions generated by the co-occurrence analysis unit 112 and the one or more non-structure-based predictions generated based on the unstructured input data 122 in order to generate one or more unstructured-fused predictions, the unstructured fusion unit 114 may utilize an unstructured fusion ML model. The unstructured fusion ML model may be a ML model configured to generate/predict one or more unstructured-fused predictions based on unfused predictions generated by two or more unfused ML models, where the unfused predictions include at least one prediction generated by a ML model configured to generate/predict structure-based predictions and at least one prediction generated by a ML model configured to generate/predict non-structure-based predictions.

In the particular ensemble architecture 450 depicted in FIG. 4B, the unstructured fusion ML model utilized by the unstructured fusion unit 114 is configured to generate unstructured-fused predictions based on structure-based unfused predictions generated by the co-occurrence analysis unit 112 and non-structure-based predictions generated based on the unstructured input data 122 stored in the storage subsystem 108. However, a person of ordinary skill in the art will recognize that the unstructured fusion ML model utilized by the unstructured fusion unit 114 may be configured to process any combination of structure-based predictions and non-structure-based predictions. In some embodiments, the unstructured fusion unit 114 is further configured to perform natural language processing on the unstructured input data 122 to generate unfused non-structure-based predictions based on the unstructured input data 122, while in other embodiments the unstructured input data 122 include pre-determined unfused non-structure-based predictions determined based on particular natural language input data (e.g., feature data extracted from medical notes data using a synonym-based natural language processing analysis).

Returning to FIG. 4B, the ensemble architecture 450 further includes retrieving the structured input data 121 from the storage subsystem and processing the structured input data 121 using the online learning unit 111 to generate one or more online learning predictions. To process the structured input data 121 to generate one or more online learning predictions, the online learning unit 111 may utilize an online ML model. The online ML model may be a ML model that utilizes sequential updates to a ML model in order to infer a relationship between a prediction input space and a prediction output space. For example, the online ML model may be an online ML model that utilizes structured medical claim data to generate one or more HPO label predictions, such as a ML model that utilizes a FTRL ML algorithm. In some embodiments, the one or more online learning predictions may be structurally hierarchical predictions. For example, in some embodiments, an online ML model may be configured to generate the one or more online learning predictions based on prediction values for prediction nodes deemed to be children prediction nodes in a structurally hierarchy characterizing the prediction domain associated with the online ML model.

The ensemble architecture 450 further includes processing the unstructured-fused predictions generated by the unstructured fusion unit 114 and the online learning predictions generated by the online learning unit 111 using the structured fusion unit 113 to generate the final predictions 401. In some embodiments, to process the unstructured-fused predictions generated by the unstructured fusion unit 114 and the online learning predictions generated by the online learning unit 111 in order to generate the final predictions 401, the structured fusion unit 113 utilizes a structured fusion ML model. The structured fusion ML model may be a ML model configured to generate/predict one or more structured-fused predictions based on unfused predictions generated by two or more unfused ML models, where the unfused predictions include at least one prediction generated by a ML model configured to generate/predict structurally hierarchical predictions and at least one prediction generated by a ML model configured to generate/predict structurally non-hierarchical predictions.

In the particular ensemble architecture 410 depicted in FIG. 4B, the structured fusion ML model utilized by the structured fusion unit 113 is configured to generate one or more structure-based predictions based on unfused predictions generated by two or more unfused ML models: structurally hierarchical predictions (i.e., the one or more online learning predictions) generated by the online ML model utilized by the online learning unit 111 and structurally non-hierarchical predictions (i.e., the one or more unstructured-fused predictions) generated by the unstructured fusion ML model utilized by the co-unstructured fusion unit 114. While the particular ensemble architecture 410 depicted in FIG. 4A includes a structured fusion unit 113 configured to process both structure-based predictions (i.e., the one or more online learning predictions) and non-structure-based predictions (the one or more unstructured-fused predictions), a person of ordinary skill in the art will recognize that the structured fusion ML model utilized by the structured fusion unit 113 may be configured to process any combination of structurally hierarchical predictions (e.g., structurally hierarchical predictions generated based on structured data, unstructured, and/or a fusion of structure-based predictions and non-structure-based predictions) and structurally non-hierarchical predictions (e.g., structurally non-hierarchical predictions generated based on structured data, unstructured, and/or a fusion of structure-based predictions and non-structure-based predictions).

B. Online ML in a Hierarchical Prediction Domain

Online learning is a method of ML in which a ML model is sequentially updated over time based on incoming training data. During training, some online learning algorithms aim to set parameters of a prediction function in a manner that optimizes co-occurrence of the prediction function with existing training data, including new training data items and/or sequentially updated training data items. For example, online learning algorithms are typically utilized to generate recommendations for a user (e.g., promotional recommendations for a user), where the user reaction to the recommendation is in turn utilized to update a ML model. In some online learning algorithms, a positive user reaction (e.g., a selection of a link corresponding to a recommendation) is used to change model parameters in a manner that increases a likelihood of future generation of the recommendation and decreases a likelihood of future generation of other recommendations, while a negative user reaction (e.g., lack of selection of a link corresponding to a recommendation) is used to change model parameters in a manner that decreases a likelihood of future generation of the recommendation and increases a likelihood of future generation of other recommendations.

Hierarchical prediction domains present unique challenges for online learning algorithms. When utilized to generate predictions related to hierarchical prediction domains, online learning algorithms should accommodate hierarchical predictive relationships between various prediction nodes in determining how to interpret incoming training data. Without applying appropriate operational adjustments that address hierarchical nature of a relevant prediction domain, online learning algorithms will require higher amounts of training data, will take longer to train, and will once trained be less accurate and reliable. Because of those challenges, various existing online learning algorithms are ill-suited for efficiently and reliably performing classification in relation to hierarchical prediction domains.

Various embodiments of the present invention address efficiency and reliability challenges related to utilizing online learning algorithms to generate predictions related to hierarchical prediction domains. According to one aspect that relates to improving efficiency and reliability of online learning in hierarchical prediction domains, various embodiments of the present invention eliminate a bias term used to penalize lack of selection of a prediction node, as hierarchical predictive relationships complicate implications of such a lack of selection for adjusting model parameters. For example, selection of a prediction node may have different implications for prediction nodes that are dependent on the particular prediction node, prediction nodes from which the particular prediction node depends, and other prediction nodes without hierarchical relationships with the particular prediction node. To address such complications, various embodiments of the present invention will not penalize lack of selection of a particular node when adjusting parameters of a relevant ML model. In doing so, various embodiments of the present invention address efficiency and reliability challenges related to utilizing online learning algorithms to generate predictions related to hierarchical prediction domains.

According to another aspect that relates to improving efficiency and reliability of online learning in hierarchical prediction domains, various embodiments of the present invention perform predictive inferences by selecting prediction nodes having sufficiently high predictive scores starting from dependent prediction nodes. In doing so, the mentioned embodiments of the present invention increase the likelihood that prediction nodes having more detailed semantic implications (e.g., more "meaningful" prediction nodes) will be selected over prediction nodes having less detailed semantic associations, thus increasing the reliability of the predictive analysis performed using online learning. For example, a prediction node associated with a thoracolumbar scoliosis HPO label will have a higher chance of selection that a prediction node associated with a scoliosis HPO label, as the former has a more meaningful semantic association than the former. This will lead to generation of structurally hierarchical predictions which have greater predictive utility. Moreover, selection of prediction labels in a hierarchical manner decreases the range of predictive scores that need to be analyzed during a predictive inference. This is because, according to various embodiments of the present invention, predictive inference will halt if a requisite number of prediction nodes are selected inmost-dependent nodes. Such techniques have the added advantage of increasing efficiency of online learning in hierarchical prediction domains by decreasing the range of prediction nodes which need to be traversed before a final prediction output is generated as part of a particular predictive inference. Thus, by selecting prediction nodes having sufficiently high predictive scores starting from dependent prediction nodes, various embodiments of the present invention address efficiency and reliability challenges related to utilizing online learning algorithms to generate predictions related to hierarchical prediction domains.

According to yet another aspect that relates to improving efficiency and reliability of online learning in hierarchical prediction domains, various embodiments of the present invention provide techniques for efficiently storing and retrieving training data. Online learning algorithms face challenges related to efficiently storing and retrieving training data during training of relevant ML models. In the absence of efficient solutions for storing and retrieving training data during training of relevant ML models, many conventional online learning algorithms are slow to train, which undermines the utility of such algorithms for predictive tasks that require real-time training and/or real-time model updates. To address such challenges, various embodiments of the present invention store training data entries in a highly sparse vector using a hashing mechanism. This aspect serves to increase efficiency and reliability of online learning in all domains, including in in hierarchical prediction domains. Thus, by storing training data entries in a highly sparse vector using a hashing mechanism, various embodiments of the present invention address efficiency and reliability challenges related to utilizing online learning algorithms to generate predictions related to hierarchical prediction domains.

FIG. 5 provides a flowchart diagram of an example process 500 for training an online ML model to perform predictive inferences related to a hierarchical prediction domain. Via the various steps/operations of process 500, the model generation unit 115 of the classification computing entity 106 can train predictive inferences using a ML model that eliminates a bias term used to penalize lack of selection of a prediction node, selects prediction nodes having sufficiently high predictive scores starting from dependent prediction nodes, and/or stores training data entries in a highly sparse vector using a hashing mechanism.

The process 500 begins at step/operation 501 when the model generation unit 115 prepares hierarchically-expanded training data. In some embodiments, to prepare hierarchically-expanded training data, the model generation unit 115 first retrieves raw training data 124 from the storage subsystem 108. The raw training data 124 may include, for each training entity (e.g., patient), one or more training features (e.g., medical codes) and one or more training prediction labels (e.g., one or more HPO labels), where at least one of the training prediction labels is associated with a hierarchical predictive relationship. After retrieving raw training data 124, the model generation unit 115 may identify each prediction node that is a parent to the at least one of the training prediction labels and generate a corresponding training data object for each identified prediction node. For example, given raw training data objects {A1, A2, A3→X1}, {A4, A5, A6→X2}, and {A7, A8, A9→X3} (where $\{\alpha, \beta, \varsigma \to \varepsilon\}$ denotes that training features $\alpha, \beta, \varsigma$ are associated with the training prediction label $\varepsilon$), and further given that X1 and X2 both depend from X3, the model generation unit 115 may generate the following hierarchically-expanded training data objects: {A1, A2, A3→X1}, {A4, A5, A6→X2}, {A7, A8, A9→X3}, {A1, A2, A3→X3}, {A4, A5, A6→X3}.

In some embodiments, step/operation 501 can be performed in accordance with the various steps/operations depicted in FIG. 6. The process depicted in FIG. 6 begins at step/operation 601 when the model generation unit 115 obtains one or more training data objects each associated with one or more training features and one or more training prediction labels. In some embodiments, the one or more training prediction labels are ground-truth predictions associated with particular training features. For example, training features may include medical procedure codes associated with medical procedures for a patient, while training prediction labels may include HPO labels for the patient.

At step/operation 602, the model generation unit 115 converts each set of training features for a training data object obtained in step/operation 601 into a feature string for the training data object. In some embodiments, the model generation unit 115 generates a feature string for each training data object identified in step/operation 601 based on each training feature associated with the training data object. For example, for training data object {A1, A2, A3→X1} (where {α, β, ç→ε} denotes that training features α, β, ç are associated with the training prediction label ç) the model generation unit 115 may generate the following feature string for the respective training data object: A1A2A3X1. In some embodiments, the model generation unit 115 generates one or more inferred features from the training features identified in step/operation 601. Then, for each training data object identified in step/operation 601, the model generation unit 115 generates a feature string for each training data object identified in step/operation 601 based on each inferred training feature associated with the training data object. For example, for training data object {A1, A2, A3→X1} (where {α, β, ç→ε} denotes that training features α, β, ç are associated with the training prediction label ε), the model generation unit 115 may generate the inferred training features B1 and B2 based on the training features A1, A2, and A3 and then generate the following feature string for the respective training data object: B1B2.

At step/operation 603, the model generation unit 115 identifies, for each training data object obtained in step/operation 601, each parent prediction label for at least one prediction label associated with the training data object, where the parent prediction label for a particular prediction label is a prediction label from which the particular prediction label depends according to the hierarchical predictive relationships characterizing a relevant hierarchical prediction domain. For example, given raw training data object {A1, A2, A3→X1} (where {α, β, ç→ε} denotes that training features α, β, ç are associated with the training prediction label ε), and further given that X1 depends from the prediction label X3, the model generation unit 115 may identify the prediction label X3 as a parent prediction label for a prediction label associated with the mentioned training data object. In some embodiments, to identify parent prediction labels, the model generation unit 115 utilizes a graph traversal algorithm.

At step/operation 604, the model generation unit 115 generates hierarchically-expanded training data based on each feature string generated in step/operation 602, each training prediction label obtained in step/operation 601, and each parent prediction label identified in step/operation 603. In some embodiments, to generate the hierarchically-expanded training data, the model generation unit 115 generates a hierarchically-expanded training data object for each parent prediction node which associates the parent prediction node to the training features that are associated with the prediction node which depends from the parent prediction node. For example, given raw training data objects {A1, A2, A3→X1}, {A4, A5, A6→X}, and {A7, A8, A9→X3} (where {α, β, çε} denotes that training features α, β, ç are associated with the training prediction label ε), and further given that X1 and X2 both depend from X3, the model generation unit 115 may generate the following hierarchically-expanded training data objects, which include the latter hierarchically-expanded training data objects for the parent prediction node X3: {A1, A2, A3→X1}, {A4, A5, A6→X2}, {A7, A8, A9→X3}, {A1, A2, A3→X3}, {A4, A5, A6→X3}.

FIGS. 7-9 provide operational examples of various aspects of an example process for generating hierarchically-expanded training data objects based on particular raw training data objects. In particular, FIG. 7 provides an operational example of a raw training data object set 700 that includes three training data objects: a first training data object 701 which associates a particular training feature A to a particular training prediction label related to abnormality of the curvature of the vertebral column; a second training data object 702 which associates a particular training feature B to a particular training prediction label related to abnormality of the thoracic spine; and a third training data object 703 which associates a particular training feature C to a particular prediction label related to kyphosis. The three training data objects in the raw training data object set 700 may be represented as {A→abnormality of the curvature of the vertebral column} for the first training data object 701, {B→abnormality of the thoracic spine} for the second training data object 702, and {C→kyphosis} for the third training data object 703, where {α, β, ç→ε} denotes that training features α, β, ç are associated with the training prediction label ε. A feature as depicted in FIG. 7 may include one or more feature attributes, e.g., one or more patient descriptor attributes, one or more procedure attributes, and/or one or more ICD codes, etc.

FIG. 8 provides an operational example of a hierarchical prediction domain 800. The depicted exemplary hierarchical prediction domain 800 comprises a number of prediction nodes each of which has a number of predictive hierarchical relationships, including child-hierarchical relationships and/or parent-dependence relationship. For example, prediction node 804 associated with the abnormality of the thoracic spine (which relates to the training feature for the second training data object 702 in the raw training object data set 700 of FIG. 7) has child-dependence relationships with the following prediction nodes: prediction node 803 associated with thoracic kyphosis, prediction node 802 associated with thoracolumbar kyphosis, and prediction node 801 associated with thoracolumbar kyphoscoliosis. As another example, prediction node 804 has parent-dependence relationships with the following prediction nodes: prediction node 807 associated with the abnormality of the thorax, prediction node 808 associated with the abnormality of the vertebral column, prediction node 809 associated with abnormal axial skeleton morphology, prediction node 810 associated with the abnormality of the skeletal morphology, prediction node 811 associated with abnormality of the skeletal system, and prediction node 812 associated with the phenotypic abnormality.

As yet another example in the depicted exemplary hierarchical prediction domain 800 of FIG. 8, prediction node 806 associated with the abnormality of the curvature of the vertebral column (which relates to the training feature for the first training data object 701 in the raw training object data set 700 of FIG. 7) is associated with the following parent-dependence relationships: prediction node 808 associated with the abnormality of the vertebral column, prediction node 809 associated with abnormal axial skeleton morphology, prediction node 810 associated with the abnormality of the skeletal morphology, prediction node 811 associated with abnormality of the skeletal system, and prediction node 812 associated with the phenotypic abnormality. As a further example, prediction node 805 associated with kyphosis (which relates to the training feature for the third training data object 703 in the raw training object data set 700 of FIG. 7) is associated with the following parent-dependence relationships: prediction node 806 associated with the abnormality of the curvature of the vertebral column (which relates to the training feature for the first training data object 701 in the raw training object data set 700 of FIG. 7), prediction node 808 associated with the abnormality of the vertebral column, prediction node 809 associated with abnormal axial skeleton morphology, prediction node 810 associated with the abnormality of the skeletal morphology, prediction node 811 associated with abnormality of the skeletal system, and prediction node 812 associated with the phenotypic abnormality.

FIG. 9 provides an operational example of a hierarchically-expanded training data object set 900 which includes, for each raw training data object depicted in the raw training object data set 700 of FIG. 7, a hierarchically-expanded training data object with the parent prediction labels for the training prediction label in the raw training data object in addition to the training prediction label itself. Thus, the hierarchically-expanded training data object set 900 includes a first hierarchically-expanded training data object 901 which includes, for feature A associated with the first training data object 701 in the raw training object data set 700, the following prediction labels: abnormality of the curvature of the vertebral column (corresponding to prediction node 806), abnormality of the vertebral column (which corresponds to prediction node 808), abnormal axial skeleton morphology (which corresponds to prediction node 809), skeletal morphology (which corresponds to prediction node 810), abnormality of the skeletal system (which corresponds to prediction node 811), and phenotypic abnormality (which corresponds to prediction node 812). Furthermore, the hierarchically-expanded training data object set 900 includes a second hierarchically-expanded training data object 902 which includes, for feature B associated with the second training data object 702 in the raw training object data set 700, the following prediction labels: abnormality of the thoracic spine (which corresponds to prediction node 804), abnormality of the thorax (which corresponds to prediction node 807), abnormality of the vertebral column (which corresponds to prediction node 808), abnormal axial skeleton morphology (which corresponds to prediction node 809), skeletal morphology (which corresponds to prediction node 810), abnormality of the skeletal system (which corresponds to prediction node 811), and phenotypic abnormality (which corresponds to prediction node 812). Moreover, the hierarchically-expanded training data object set 900 includes a third hierarchically-expanded training data object 903 which includes, for feature B associated with the third training data object 703 in the raw training object data set 700, the following prediction labels: kyphosis (which corresponds to prediction node 805), abnormality of the curvature of the vertebral column (corresponding to prediction node 806), abnormality of the vertebral column (which corresponds to prediction node 808), abnormal axial skeleton morphology (which corresponds to prediction node 809), skeletal morphology (which corresponds to prediction node 810), abnormality of the skeletal system (which corresponds to prediction node 811), and phenotypic abnormality (which corresponds to prediction node 812).

In some embodiments, the model generation unit 115 may generate the following hierarchically-expanded training data objects based on the hierarchically-expanded training data object set 900 depicted in FIG. 9 (where {α, β, ç→ε} denotes that training features α, β, ç are associated with the training prediction label ε): {Feature A→Abnormality of the Curvature of the Vertebral Column}, {Feature A→Abnormality of the Vertebral Column}, {Feature A→Abnormality of the Axial Skeleton Morphology}, {Feature A→Abnormality of the Skeletal System}, {Feature A→Phenotypic Abnormality}, {Feature B→Abnormality of the Thoracic Spine}, {Feature B→Abnormality of the Thorax}, {Feature B→Abnormality of the Vertebral Column}, {Feature B→Abnormality of the Axial Skeleton Morphology}, {Feature B→Abnormality of the Skeletal System}, {Feature B→Phenotypic Abnormality}, {Feature C→, Kyphosis}, {Feature C→Abnormality of the Vertebral Column}, {Feature C→Abnormality of the Axial Skeleton Morphology}, {Feature C→Abnormality of the Skeletal System}, {Feature C→Phenotypic Abnormality}.

Returning to FIG. 5, at step/operation 502, the model generation unit 115 initializes an FTRL ML model. The FTRL ML model may be an example of an online learning algorithm which is configured to perform at least the following operations: (1) obtain a prediction input (e.g., an input vector); (2) obtain a parameter data object (e.g., a parameter data object) having an initial value; (3) perform a prediction data object (e.g., a prediction vector) using the prediction object and the parameter data object (e.g., using logistic regression with a sigmoid function); (4) obtain a ground-truth observation data object (e.g., a ground-truth observation data object); and (5) update the parameter data object based on the ground-truth observation data object (e.g., based on a gradient of the error between the prediction data object and the ground-truth observation data object, for example by using online gradient descent). In many conventional FTRL ML models, the initial value of the parameter data object is configured to generate a zero-valued prediction data object and the update in the fifth operation is characterized by a reward term configured to reward occurrence of a positive ground-truth observation data object (e.g., a ground-truth observation data object indicating selection of a predicted item by an end-user) and a bias term configured to penalize lack of occurrence of a negative ground-truth observation data object (e.g., a ground-truth observation data object indicating lack of selection of a predicted item by an end-user).

In some embodiments, step/operation 502 may be performed in accordance with the various steps/operations depicted in FIG. 10, which depicts the steps/operations of an example process for an generating initial weight values for an FTRL ML model. The example process depicted in FIG. 10 begins at step/operation 1001 when the model generation unit 115 obtains an FTRL ML model characterized by an initial value and a bias term. In some embodiments, the FTRL ML model in step/operation 1001 integrates at least some of the steps/operations denoted in the below algorithm:

---
Algorithm 1 Per-Coordinate FTRL-Proximal
with $L_1$ and $L_2$ Regularization for Logistic Regression
---

\#With per-coordinate learning rates of Eq. (2).
Input: parameters $\alpha, \beta, \lambda_1, \lambda_2$
($\forall i \in \{1, \ldots, d\}$), initialize $z_i = 0$ and $n_i = 0$
for $t = 1$ to T do
   Receive feature vector $x_t$ and let $I = \{i \mid x_i \neq 0\}$
   For $i \in I$ compute $$w_{t,i} = \begin{cases} 0 & \text{if } |z_i| \leq \lambda_1 \\ -\left(\frac{\beta + \sqrt{n_i}}{\alpha} + \lambda_2\right)^{-1}(z_i - \text{sgn}(z_i)\lambda_1) & \text{otherwise.} \end{cases}$$

Predict $p_t = \sigma(x_t \cdot w)$ using the $w_{t,i}$ computed above
Observe label $y_t \in \{0, 1\}$
for all $i \in I$ do
   $g_i = (p_t - y_t)x_i$    \#gradient of loss w.r.t. $w_i$ $$\sigma_i = \frac{1}{\alpha}\left(\sqrt{n_i + g_i^2} - \sqrt{n_i}\right) \quad \text{\#equals } \frac{1}{\eta_{t,i}} - \frac{1}{\eta_{t-1,i}}$$

-continued

Algorithm 1 Per-Coordinate FTRL-Proximal
with $L_1$ and $L_2$ Regularization for Logistic Regression $z_i \leftarrow z_i + g_i - \sigma_i w_{t,i}$
$n_i \leftarrow n_i + g_i^2$
end for
end for Algorithm 1 (from McMahan et al., "Ad-Click Prediction: A View from the Trenches," (2015), available online at http://www.eecs.tufts.edu/~dsculley/papers/ad-click-prediction-.pdf)

At step/operation 1002, the model generation unit 115 sets the initial value of the FTRL ML model (e.g., the values corresponding to $z_i$ in the above-depicted algorithm) to a negative value. In some embodiments, the negative value is determined based on an expected distribution of the ratio of positive ground-truth observations to negative-ground-truth observations among all the training data objects. At step/operation 1003, the model generation unit 115 removes the bias term from the FTRL ML model.

Returning to FIG. 5, at step/operation 503, the model generation unit 115 generates training data objects based on the hierarchically-expanded training data objects generated in step/operation 501. In some embodiments, to generate training data objects based on the hierarchically-expanded training data objects generated in step/operation 501, the model generation unit 115 associates each hierarchically-expanded data object generated in step/operation 604 to a prediction label for the hierarchically-expanded data object. For example, given hierarchically-expanded training data objects {A1, A2, A3→X1}, {A4, A5, A6→X2}, {A7, A8, A9→X3}, {A1, A2, A3→X3}, {A4, A5, A6→X3} where {α, β, ç→ε} denotes that training features α, β, ç are associated with the training prediction label ε, the model generation unit 115 may associate the first hierarchically-expanded training data object to the prediction label X1, the second hierarchically-expanded training data object to the prediction label X2, and the latter three hierarchically-expanded training data objects to the prediction label X3. The model generation unit 115 may thereafter generate the training data objects based on the noted associations.

At step/operation 504, the model generation unit 115 generates appended training data objects based on the training data objects generated in step/operation 503. In some embodiments, to generate the appended training data objects based on the training data objects generated in step/operation 503, the model generation unit 115 appends each training data object generated in step/operation 503 to the prediction label determined to be associated with the corresponding training data object. For example, given the training data objects {A1, A2, A3→X1} associated with the prediction label X1, {A4, A5, A6→X2} associated with the prediction label X2, {A7, A8, A9→X3} associated with the prediction label X3, {A1, A2, A3→X3} associated with the prediction label X3, and {A4, A5, A6→X3} associated with the prediction label X3, where {α, β, ç→ε} denotes that training features α, β, ç are associated with the training prediction label ε, the model generation unit 115 may generate the following appended training data objects: A1A2A3X1, A4A5A6X2, A7A8A9X3, A1A2A3X3, and A4A5A6X3.

In some embodiments, step/operation 504 may be performed in accordance with the various steps/operations depicted in FIG. 11, which depicts the steps/operations of an example process for storing appended training data objects. The example process depicted in FIG. 11 begins at step/operation 1101 when the model generation unit 115 appends each feature string generated in step/operation 602 to each corresponding prediction label for the feature string and to each parent prediction label for the feature string identified in step/operation 603 to generate one or more appended training data objects for the feature string. For example, given the training feature string A1A2A3 associated with the prediction node X1 which is in turn a hierarchical child of the prediction node X3, the model generation unit 115 may generate the following appended training data objects for the feature string A1A2A3: A1A2A3X1 and A1A2A3X3. As another example, given the training feature string A4A5A6 associated with the prediction node X2 which is in turn a hierarchical child of the prediction node X3, the model generation unit 115 may generate the following appended training data objects for the feature string A4A5A6: A4A5A6X2 and A4A5A6X3. As a further example, given the training feature string A7A8A9X3 associated with the prediction node X3 which is in turn a hierarchical child of the prediction node X4, the model generation unit 115 may generate the following appended training data objects for the feature string A7A8A9X3: A7A8A9X3 and A7A8A9X4.

At step/operation 1102, the model generation unit 115 generates a corresponding encoding location for each appended training data entry generated in step/operation 1101 in a highly sparse data object (e.g., a highly sparse vector). In some embodiments, a highly sparse vector is a vector whose sparsity exceeds a sparsity threshold. In some embodiments, to a corresponding encoding location for each appended training data entry generated in step/operation 1101 in a highly sparse data object, the model generation unit 115 utilizes a hashing function configured to deterministically associate each appended training data entry generated in step/operation 1101 to a particular encoding location in the highly sparse data object. For example, in some embodiments, the model generation unit 115 may first convert each appended training data object to a numeric value, e.g., based on the American Standard Code for Information Interchange (ASCII) values for the characters of the appended training data object. Thereafter, the model generation unit 115 may apply a hashing function to the numeric value to determine the encoding location.

At step/operation 1103, the model generation unit 115 stores each appended training data object in the highly sparse data object based on the encoding location for the appended training data object determined in step/operation 1102. In some embodiments, the model generation unit 115 identifies a particular location in the highly sparse data object that corresponds to the encoding location for a particular appended training data object and stores the particular appended training data object in the particular location. In some embodiments, the model generation unit 115 applies an offset to the encoding location for a particular appended training data object to determine an offset-applied location for the particular appended training data object, identifies a particular location in in the highly sparse data object that corresponds to the offset-applied location for the particular appended training data object, and stores the particular appended training data object in the particular location. In some embodiments, the model generation unit 115 stores the highly sparse data object in the storage subsystem 108 (e.g., as part of the structured input data 121 in the storage subsystem 108).

Returning to FIG. 5, at step/operation 505, the model generation unit 115 updates the FTRL ML model based on each appended training data object generated in step/operation 504. In some embodiments, to update the FTRL ML model based on each appended training data object generated in step/operation 504, the model generation unit 115 first retrieves the appended training data objects (e.g., form the highly sparse data object generated in step/operation 1103, which may be stored as part of the structured input data 121 in the storage subsystem 108). The model generation unit 115 then performs a prediction on the appended training data object based on the feature string included in the appended training data object and using the FTRL ML model initialized in step/operation 502. Afterward, the model generation unit 115 determines a measure of error between the prediction and the training label included in the appended training object. The model generation unit 115 then updates the FTRL ML model based on the measure of error (e.g., using a gradient descent algorithm, such as an online gradient descent algorithm). In some embodiments, to perform a prediction on the appended data object, the model generation unit 115 retrieves the model definition data 123 for the FTRL ML model from the storage subsystem 108. In some embodiments, after generating an updated FTRL ML model, the model generation unit 115 stores the parameters and/or hyper-parameters associated with the FTRL ML model as part of the model definition data 123 for the FTRL ML model from the storage subsystem 108.

In some embodiments, to update the FTRL ML model parameters w for the FTRL ML model based on a measure of error g at a time step t, the model generation unit 115 performs the operations corresponding to the equation $w_{t+1}=w_t\eta g_t$, where n is a non-increasing learning schedule rate value which may for example be set to $1/\sqrt{t}$. In some embodiments, to update the FTRL ML model parameters w for the FTRL ML model based on a measure of error g at a time step t, the model generation unit 115 performs the operations corresponding to the equation $w_{t+1}=\mathrm{argmin}_w (g_{1:t}, w+0.5*\Sigma_{s=1}^{t}\sigma_s\|w-w_s\|_2^2+\varphi_1\|w\|_1)$, where σ may be a predictive parameter defined based on a non-increasing learning schedule rate value n such that $\sigma_{1:t}=1/nt$. In some embodiments, to update the FTRL ML model parameters w for the FTRL ML model based on a measure of error g at a time step t, the model generation unit 115 performs the operations corresponding to the $\mathrm{argmin}_w$ $$\left(g_{1:t} - \sum_{s=1}^{t}(\sigma_s w_s)*w + \frac{1}{nt}\|w\|_2^2 + \varphi_1\|w\|_1\right),$$

where n is a non-increasing learning schedule rate value which may for example be set to $1/\sqrt{t}$.

At step/operation 506, the model generation unit 115 determines whether further FTRL ML model updates are needed. In some embodiments, to determine whether further FTRL ML model updates are needed, the model generation unit 115 first obtains the updated FTRL ML model generated in step/operation 505 (e.g., retrieves the parameters and/or hyper-parameters associated with the FTRL ML model from the model definition data 123 for the FTRL ML model stored in the storage subsystem 108). The model generation unit 115 then applies the updated FTRL to one or more validation data objects and determines a prediction for each validation data object. The model generation unit 115 then determines a validation score for the updated FTRL ML model based on the predictions determined by the FTRL ML model for the one or more validation data objects and ground-truth validation labels for the one or more validation data objects. The model generation unit 115 then determines whether further FTRL ML model updates are needed based on the validation score for the FTRL ML model (e.g., based on whether the validation score exceeds a predefined threshold validation score).

In some embodiments, step/operation 506 may be performed in accordance with the various steps/operations depicted in FIG. 12, which is a flowchart diagram of an example process for validating an FTRL ML model. The example process depicted in FIG. 12 begins at step/operation 1201 when the model generation unit 115 obtains the trained FTRL ML model after a particular training epoch (e.g., after a particular execution of the FTRL ML model updating discussed with respect to the step/operation 505). In some embodiments, a training epoch may be determined as the set of updates to an FTRL ML model performed using a particular batch of training data. In some embodiments, a training epoch may be determined as the set of updates to an FTRL performing using n training data objects, where n may be a preconfigured parameter and/or hyper-parameter of the FTRL ML model, a preconfigured parameter and/or hyper-parameter of the particular training algorithm utilized by the model generation unit 115 to train the FTRL ML model, a parameter and/or hyper-parameter of the FTRL ML model determined by using a ML algorithm, a parameter and/or hyper-parameter of the particular training algorithm utilized by the model generation unit 115 to train the FTRL ML model which is determined by using a ML algorithm, and/or the like.

At step/operation 1202, the model generation unit 115 performs a validation of the FTRL ML model using validation data to generate a validation score for the particular training epoch. In some embodiments, to perform validation of the FTRL ML model using the validation data to generate a validation score for the particular training epoch, the model generation unit 115 first retrieves validation data entries (e.g., from the structured input data 121 on the storage subsystem 108 and/or from the raw training data 124 stored on the storage subsystem 108). In some embodiments, for each training data batch having n training data entries, the model generation unit 115 designates i/n portion of the training data batch as training data utilized to train the FTRL ML model during a training epoch and j/m portion of the training data batch as validation data utilized to validate the FTRL ML model during a validation epoch, where at least one of n, i, and j may be a preconfigured parameter and/or hyper-parameter of the FTRL ML model, a preconfigured parameter and/or hyper-parameter of the particular training algorithm utilized by the model generation unit 115 to train the FTRL ML model, a parameter and/or hyper-parameter of the FTRL ML model determined by using a ML algorithm, a parameter and/or hyper-parameter of the particular training algorithm utilized by the model generation unit 115 to train the FTRL ML model which is determined by using a ML algorithm, and/or the like.

In some embodiments, subsequent to retrieving validation data entries, the model generation unit 115 performs predictions corresponding to the validation data entries using the FTRL ML model. The model generation unit 115 may apply one or more parameters of the FTRL ML model to the validation data entries to determine a corresponding prediction for each validation data entry. Thereafter, the model generation unit 115 determines a measure of error between each prediction associated with a corresponding validation data object and a ground-truth label associated with the corresponding validation data object. In some embodiments, the model generation unit 115 determines, for each validation data object characterized by a ground-truth prediction label and associated with an inferred prediction generated based on the FTRL ML model, a measure of numeric deviation between the ground-truth prediction for the validation data object and the associated inferred prediction for the validation data object.

In some embodiments, subsequent to determining each measure of error between a prediction associated with a corresponding validation data object and a ground-truth label associated with the corresponding validation data object, model generation unit 115 then determines a validation score for the FTRL ML model based on an aggregation of each noted measure of error. In some embodiments, the model generation unit 115 determines the validation score based on a measure of statistical distribution (e.g., a mean, median, mode, and/or the like.) of each measure of error between a prediction associated with a corresponding validation data object and a ground-truth label associated with the corresponding validation data object. For example, the model generation unit 115 may determine the validation score for the FTRL ML model based on a measure of statistical distribution (e.g., a mean, median, mode, and/or the like.) of each measure of numeric deviation between a ground-truth prediction for a validation data object and the associated inferred prediction for a validation data object.

At step/operation 1203, the model generation unit 115 determines whether the validation score satisfies (e.g., exceeds and/or is equal to or greater than) a threshold validation score. If the model generation unit 115 determines that the validation score satisfies the threshold validation score, the model generation unit 115 determines at step/operation 1204 that no further updates to the FTRL ML model are needed. However, if the model generation unit 115 determines that the validation score fails to satisfy the threshold validation score, the model generation unit 115 determines at step/operation 1205 that further updates to the FTRL ML model are needed. Thus, in some embodiments, the model generation unit 115 continues the training for as many training epochs as needed until the FTRL ML model converges with validation data entries and/or until the validation score determined for the FTRL ML model satisfies a threshold validation score.

In some embodiments, the threshold validation score is determined based on at least one of a preconfigured parameter and/or hyper-parameter of the FTRL ML model, a preconfigured parameter and/or hyper-parameter of the particular training algorithm utilized by the model generation unit 115 to train the FTRL ML model, a parameter and/or hyper-parameter of the FTRL ML model determined by using a ML algorithm, a parameter and/or hyper-parameter of the particular training algorithm utilized by the model generation unit 115 to train the FTRL ML model which is determined by using a ML algorithm, and/or the like. In some embodiments, the threshold validation score is determined based on a measure of statistical distribution (e.g., a mean, median, mode, and/or the like.) of each measure of error between a prediction associated with a corresponding validation data object and a ground-truth label associated with the corresponding validation data object. In some embodiments, the threshold validation score is determined based on a measure of statistical distribution (e.g., a mean, median, mode, and/or the like.) of each measure of numeric deviation between a ground-truth prediction for a validation data object and the associated inferred prediction for a validation data object. In some embodiments, the threshold validation score is the same value for multiple training epochs associated with an FTRL ML model. In some embodiments, the threshold validation score may be different values for different training epochs associated with an FTRL ML model.

The example process depicted in FIG. 12 thus may lead to training of an FTRL ML model for as many training epochs as needed until the FTRL ML model converges with validation data entries and/or until the validation score determined for the FTRL ML model satisfies a threshold validation score. As noted above, however, this is only one example of various possible techniques for determining whether further updates to an FTRL ML model are needed. Indeed, a person of ordinary skill in the art will recognize that there are various other techniques for determining whether further updates to an FTRL ML model are needed, for example the technique of repeating the training of an FTRL ML model based on a training repetition parameterp, which may be a statistically-determined parameter or a dynamically-determined parameter. In some embodiments, the model generation unit 115 continues the training of the FTRL ML model forp training epochs. In some embodiments, the training repetition parameterp may be determined based on at least one of a preconfigured parameter and/or hyper-parameter of the FTRL ML model, a preconfigured parameter and/or hyper-parameter of the particular training algorithm utilized by the model generation unit 115 to train the FTRL ML model, a parameter and/or hyper-parameter of the FTRL ML model determined by using a ML algorithm, a parameter and/or hyper-parameter of the particular training algorithm utilized by the model generation unit 115 to train the FTRL ML model which is determined by using a ML algorithm, and/or the like.

Returning to FIG. 5, if the model generation unit 115 determines at step/operation 506 that further FTRL ML models are needed, the model generation unit 115 repeats steps/operations 504 until after the successful execution of a training epoch after which the model generation unit 115 determines at step/operation 506 that no further FTRL ML models are needed. However, if the model generation unit 115 determines at step/operation 506 that further FTRL ML models are not needed, the model generation unit 115 exports the trained FTRL ML model at step/operation 507. In some embodiments, after the model generation unit 115 determines at step/operation 506 that further FTRL ML models are not needed, the model generation unit 115 determines that the FTRL ML model is a trained FTRL ML model and transmits the trained FTRL ML model to an end-user. In some embodiments, after the model generation unit 115 determines at step/operation 506 that further FTRL ML models are not needed, the model generation unit 115 determines that the FTRL ML model is a trained FTRL ML model and stores the trained FTRL ML model is a local and/or a remote database, e.g., as part of the model definition data 123 for the FTRL ML model in the storage subsystem 108.

Once trained by the model generation unit 115, the online learning unit 111 may utilize a trained online ML model (e.g., a trained FTRL ML model) to perform predictions in a hierarchical prediction domain. To perform predictions in a hierarchical prediction domain using the trained online ML model, the online learning unit 111 can apply the trained online ML model to particular prediction inputs to generate prediction scores for each prediction node in the hierarchical prediction domain. Thereafter, the online learning unit 111 can generate a final prediction output based on each prediction score for a prediction node in the hierarchical prediction domain. To do so, the online learning unit 111 may perform a brute-force comparison of all prediction scores associated with a hierarchical prediction domain. This, however, may prove computationally expensive for large hierarchical prediction domains, such as the HPO hierarchical prediction domain.

Accordingly, various embodiments of the present invention perform predictive inferences by selecting prediction nodes having sufficiently high predictive scores starting from dependent prediction nodes. In doing so, the mentioned embodiments of the present invention increase the likelihood that prediction nodes having more detailed semantic implications (e.g., more "meaningful" prediction nodes) will be selected over prediction nodes having less detailed semantic associations, thus increasing the reliability of the predictive analysis performed using online learning. For example, a prediction node associated with a thoracolumbar scoliosis HPO label will have a higher chance of selection that a prediction node associated with a scoliosis HPO label, as the former has a more meaningful semantic association than the former. This will lead to generation of structurally hierarchical predictions which have greater predictive utility. Moreover, selection of prediction labels in a hierarchical manner decreases the range of predictive scores that need to be analyzed during a predictive inference. This is because, according to various embodiments of the present invention, predictive inference will halt if a requisite number of prediction nodes are selected inmost-dependent nodes. Such techniques have the added advantage of increasing efficiency of online learning in hierarchical prediction domains by decreasing the range of prediction nodes which need to be traversed before a final prediction output is generated as part of a particular predictive inference. Thus, by selecting prediction nodes having sufficiently high predictive scores starting from dependent prediction nodes, various embodiments of the present invention address efficiency and reliability challenges related to utilizing online learning algorithms to generate predictions related to hierarchical prediction domains.

FIG. 13 provides a flowchart diagram of an example process 1300 for generating prediction labels using a trained FTRL ML model and in a hierarchical prediction domain. Via the various steps/operations of process 1300, the online learning unit 111 of the classification computing entity 106 can perform predictive inferences by selecting prediction nodes having sufficiently high predictive scores starting from dependent prediction nodes in a manner that improves efficiency and reliability of applying the FTRL ML model to generate predictions related to hierarchical prediction domains.

The process 1300 begins at step/operation 1301 when the online learning unit 111 obtains a prediction input data object. The prediction input data object may be a data object that includes one or more prediction input features, such as one or more structured input features (e.g., medical codes for a particular patient). In some embodiments, the prediction input data object is associated with a predictive entity (e.g., a patient), which may be a real-world entity with respect to which a prediction inference is being made. In some embodiments, at least a portion of the prediction input data object is obtained from an external computing entity 102, such as an external computing entity 102 associated with a healthcare delivery organization, an external computing entity 102 associated with a health insurance provider organization, an external computing entity 102 associated with an auditing organization, an external computing entity 102 associated with a regulatory organization, and/or the like. In some embodiments, at least a portion of the prediction input data object is retrieved from a local and/or remote database, such as from the storage subsystem 108 of the classification system 101. In some embodiments, the prediction input data object is a prediction input vector, e.g., an atomic m*1 vector stored as a one-dimensional array of size m and a vector in a prediction input in an m*n matrix including n vectors stored as a two-dimensional array of size m*n.

At step/operation 1302, the online learning unit 111 obtains a trained FTRL ML model, e.g., a trained FTRL ML model trained using the example process 500 depicted in FIG. 5. In some embodiments, to obtain the trained FTRL ML model, the online learning unit 111 retrieves parameters and/or hyper-parameters associated with the FTRL ML model from the model definition data 123 in the storage subsystem 108. In some embodiments, the FTRL ML model is an FTRL ML model trained without a bias term and/or with initial weight values configured to generate negative prediction scores. Although the example process 1300 depicted in FIG. 13 discusses an FTRL ML model, a person of ordinary skill in the art will recognize that the process 1300 may be performed using any ML model, such as any online ML model.

At step/operation 1303, the online learning unit 111 utilizes the trained FTRL ML model to generate prediction score for each prediction node in the hierarchical prediction domain. In some embodiments, the trained FTRL ML model may be configured such that, for each hierarchical structure within the hierarchical prediction domain which includes a group of prediction nodes having one or more head prediction nodes, the more hierarchically dependent prediction nodes have higher prediction scores than the less hierarchically dependent prediction nodes. For example, given a hierarchical prediction structure characterized by the hierarchical prediction relationships A>>B,C; B>>D, E; C>>F; and F>>I (where X>>Y,Z denotes that prediction nodes Y and Z are hierarchically dependent on the prediction node X); the prediction node I may have a higher prediction score than the prediction nodes F and C and A, the prediction node F may have a higher prediction score than the prediction nodes C and A, the prediction scores D and E may have a higher prediction score than the prediction nodes B and A, and the predictions B and C may have a higher prediction score than the prediction node A. In other embodiments, the trained FTRL ML model may be configured to generate prediction scores irrespective of the hierarchical position of a prediction node in the hierarchical prediction domain.

FIG. 14 provides an operational example of a predictive score data object 1400 for a hierarchical structure within a hierarchical prediction domain. The hierarchical structure corresponding to the predictive score data object 1400 includes a group of sixteen prediction nodes with a head prediction node 1409, from which the fifteen non-head prediction nodes directly or indirectly depend. The predictive score data object 1400 includes a predictive score for each prediction node associated with the hierarchical structure, including the following prediction scores: a prediction score 0.5 for dependent prediction node 1401; prediction scores 0.9, 0.3, and 0.1 for second-layer prediction nodes 1402, 1403, and 1404; prediction scores 0.2, 0.4, 0.5, and 0.9 for third-layer prediction nodes 1405, 1406, 1407, and 1408; and prediction score 0.4 for the head prediction node 1409.

Returning to FIG. 13, at step/operation 1304, the online learning unit 111 selects up to K prediction labels on each hierarchical level, starting from the most-dependent hierarchical level. At step/operation 1305, the online learning unit 111 determines whether K prediction labels have been selected from all hierarchical levels. In some embodiments, starting at the most-dependent hierarchical level and going to the higher hierarchical levels, the online learning unit 111 selects top prediction nodes on each layer until it reaches K prediction nodes. Therefore, a prediction node on a lower hierarchical level may be selected over a prediction node on an upper hierarchical level even though the former prediction node has a lower prediction score than the latter prediction node. In some embodiments, K is an output diversity parameter for the FTRL ML model. In some embodiments, the output diversity parameter for the FTRL ML model may be determined based on at least one of a preconfigured parameter and/or hyper-parameter of the FTRL ML model, a preconfigured parameter and/or hyper-parameter of the particular training algorithm utilized by the model generation unit 115 to train the FTRL ML model, a parameter and/or hyper-parameter of the FTRL ML model determined by using a ML algorithm, a parameter and/or hyper-parameter of the particular training algorithm utilized by the model generation unit 115 to train the FTRL ML model which is determined by using a ML algorithm, and/or the like.

In some embodiments, step/operation 1304 may be described using the operational example of FIG. 14. For example, if K=3, the online learning unit 111 may select the following prediction nodes from the hierarchical structure associated with the prediction score data object 1400 of FIG. 14: prediction node 1401 (i.e., the prediction node having the highest prediction score in the most-dependent hierarchical level, whose selection increments a node selection count value I to generate I=1); prediction node 1403 (i.e., the prediction node having the highest prediction score in the second hierarchical level, whose selection increments I to generate I=2); and prediction node 1404 (i.e., the prediction node having the second-highest prediction score in the second hierarchical level, whose selection increments I to generate I=3, which equals K thus terminating the graph traversal).

By selecting prediction nodes based at least in part on the hierarchical level of those prediction nodes, various embodiments of the present invention perform predictive inferences by selecting prediction nodes having sufficiently high predictive scores starting from dependent prediction nodes. In doing so, the mentioned embodiments of the present invention increase the likelihood that prediction nodes having more detailed semantic implications (e.g., more "meaningful" prediction nodes) will be selected over prediction nodes having less detailed semantic associations, thus increasing the reliability of the predictive analysis performed using online learning. For example, a prediction node associated with a thoracolumbar scoliosis HPO label will have a higher chance of selection that a prediction node associated with a scoliosis HPO label, as the former has a more meaningful semantic association than the former. This will lead to generation of structurally hierarchical predictions which have greater predictive utility. Moreover, selection of prediction labels in a hierarchical manner decreases the range of predictive scores that need to be analyzed during a predictive inference. This is because, according to various embodiments of the present invention, predictive inference will halt if a requisite number of prediction nodes are selected among the most-dependent nodes. Such techniques have the added advantage of increasing efficiency of online learning in hierarchical prediction domains by decreasing the range of prediction nodes which need to be traversed before a final prediction output is generated as part of a particular predictive inference. Thus, by selecting prediction nodes having sufficiently high predictive scores starting from dependent prediction nodes, various embodiments of the present invention address efficiency and reliability challenges related to utilizing online learning algorithms to generate predictions related to hierarchical prediction domains.

Moreover, by selecting prediction nodes based at least in part on the hierarchical level of those prediction nodes, various embodiments of the present invention generate structurally hierarchical predictions. A structurally hierarchical prediction may be a prediction determined based at least in part on a position of a corresponding prediction node in a structural hierarchy characterizing the hierarchical prediction domain that includes the corresponding prediction node. For example, in some embodiments, an online ML model may be configured to generate the one or more online learning predictions based on prediction values for prediction nodes deemed to be dependent prediction nodes in a structurally hierarchy characterizing the prediction domain associated with the online ML model. In at least some of those embodiments, the online ML model will not generate predictions that correspond to non-most-dependent nodes in the structural hierarchically characterizing the prediction domain associated with the online ML model. By generating structurally hierarchical predictions, the online learning unit 111 can generate prediction nodes based on prediction nodes deemed to be more semantically significant. Thus, by selecting prediction nodes based at least in part on the hierarchical level of those prediction nodes, various embodiments of the present invention improve reliability of online ML in hierarchical prediction domains, such as in hierarchical prediction domains having a large number of hierarchical structures and/or having a large number of prediction nodes.

Returning to FIG. 13, if the online learning unit 111 determines at step/operation 1305 that K prediction labels have been selected from all hierarchical layers in the hierarchical structure, the online learning unit 111 generates the prediction labels based on the selected K prediction labels. In some embodiments, the online learning unit 111 provides the prediction labels and/or a prediction output determined based on the prediction labels to an external computing entity 102, such as an external computing entity 102 associated with a healthcare delivery organization, an external computing entity 102 associated with a health insurance provider organization, an external computing entity 102 associated with an auditing organization, an external computing entity 102 associated with a regulatory organization, and/or the like. In some embodiments, the online learning unit 111 stores the prediction labels and/or a prediction output determined based on the prediction labels on a local and/or remote database, such as from the storage subsystem 108 of the classification system 101.

However, if the online learning unit 111 determines at step/operation 1305 that K prediction labels have not been selected from all hierarchical layers in the hierarchical structure, the online learning unit proceeds to a higher layer and performs the step/operation 1304 with respect to that layer. Thus, if for example K=5, the online learning unit 111 may select the following prediction nodes from the hierarchical structure associated with the prediction score data object 1400 of FIG. 14: prediction node 1401 (i.e., the prediction node having the highest prediction score in the most-dependent hierarchical level, whose selection increments a node selection count value I to generate I=1); prediction node 1403 (i.e., the prediction node having the highest prediction score in the second hierarchical level, whose selection increments I to generate I=2); prediction node 1404 (i.e., the prediction node having the second-highest prediction score in the second hierarchical level, whose selection increments I to generate I=3); prediction node 1408 (i.e., the prediction node having the highest prediction score in the third hierarchical level, whose selection increments I=4); and prediction node 1407 (i.e., the prediction node having the second-highest prediction score in the third hierarchical level, whose selection increments I=5, which equals K and thus terminates the graph traversal).

C. Co-Occurrence Analysis in Hierarchical Prediction Domains

While online ML provides important insights about relationships among prediction inputs with hierarchical structures in a hierarchical prediction domains and has the flexibility of sequential updatability over time, other important insights can be inferred from analyzing statistical relations of particular features and particular prediction labels among training data. However, given large amounts of training data, such statistical analyses may suffer from reliability drawbacks if they do not properly accommodate for factors that complicate conceptual predictive inferences from numeric patterns. For example, trivially frequent correlations can complicate accurate and reliable conceptual inferences from statistical correlations. As another example, markedly infrequent occurrences can also complicate statistical analysis of predictive data in order to infer conceptual notions that can facilitate effective classification. As a further example, conceptually obvious correlations may distort cross-data analyses of correlations between features and prediction labels without contributing sufficient conceptual value to the predictive inference process.

Because of such complexities associated with translation of numeric patterns to conceptual predictive frameworks, many existing statistical ML problems face substantial challenges when it comes to efficiently and reliably performing predictive inferences based on co-occurrence data. To address reliability concerns stemming from complexities associated with translation of numeric patterns to conceptual predictive frameworks, many conventional statistical ML problems resort to expensive training operations that undermine efficiency of ML solutions without sufficiently contributing to the reliability and accuracy of the predictions performed by those ML solutions. Thus, there is a continuing technical need for efficient and reliable solutions for statistical ML in various classification domains, such as in hierarchical prediction domains.

Various embodiments of the present invention address the efficiency and reliability challenges related to complexities associated with translation of numeric patterns to conceptual predictive frameworks. For example, various embodiments of the present invention provide innovative solutions for both normalizing feature-label co-occurrence data and significance-based filtering of such co-occurrence data. Through the noted techniques, various embodiments of the present invention provide computationally efficient solutions that address complexities associated with translation of numeric patterns to conceptual predictive frameworks, such as complexities associated with trivially frequent co-occurrences, complexities associated with mistakenly under-recorded co-occurrences, and complexities associated with conceptually obvious co-occurrences. Accordingly, by both normalizing feature-label co-occurrence data and significance-based filtering of such co-occurrence data, various embodiments of the present invention address technical challenges related to efficiency and reliability of statistical ML solutions and improve efficiency and reliability of various existing conventional statistical ML solutions. The resulting improvements address efficiency and reliability of all statistical ML solutions, including statistical ML solutions utilized in hierarchical prediction domains. Thus, while aspects of the co-occurrence analysis ML models are described herein with respect to statistical ML solutions utilized in hierarchical prediction domains, one of ordinary skill in the art will recognize that the co-occurrence analysis ML models can be utilized to improve efficiency and reliability of all statistical ML solutions, including statistical ML solutions utilized in non-hierarchical prediction domains.

In addition to improving efficiency and reliability of all statistical ML solutions, some aspects of the co-occurrence analysis ML models described herein include important contributions to efficiency and reliability of ML in hierarchical prediction domains. In hierarchical prediction domains, the presence of hierarchical relationships between prediction nodes in the output space complicates the task of inferring a prediction output based on prediction scores for various prediction nodes. On the one hand, the hierarchical relationships between prediction nodes in the output space provide important domain information that can facilitate efficient and reliable predictive inferences. On the other hand, important predictive conclusions may be inferred from ignoring the hierarchical relationships, especially in instances where the available hierarchical models do not capture all of the relevant information about conceptual relationships between prediction nodes and/or include potentially erroneous information about conceptual relationships between prediction nodes. Thus, there is a continuing technical challenge associated with performing predictive analyses in a manner that takes into account both hierarchical composition of the output space and cross-hierarchical composition of the output space.

Various embodiments of the present invention address the mentioned technical challenges associated with considering both hierarchical composition of the output space and cross-hierarchical composition of the output space when performing classification in hierarchical prediction domains. For example, various embodiments of the present invention relate to co-occurrence analysis ML models that generate structurally non-hierarchical predictions. A structurally non-hierarchical prediction may be a prediction determined without regard to a position of the corresponding prediction node in a structural hierarchy characterizing the hierarchical prediction domain that includes the corresponding prediction node. For example, in some embodiments, a co-occurrence analysis ML model may be configured to generate the one or more co-occurrence analysis predictions based on prediction values for prediction nodes regardless of whether the prediction nodes are deemed to be dependent prediction nodes in a structurally hierarchy characterizing the prediction domain associated with the co-occurrence analysis ML model. In at least some of those embodiments, the co-occurrence analysis ML model may generate predictions that correspond to both most-dependent nodes and non-most-dependent nodes in the structural hierarchically characterizing the prediction domain associated with the online ML model.

By generating structurally non-hierarchical predictions, various embodiments of the present invention provide predictions that are agnostic to the hierarchical composition of the prediction output space. When used in combination and/or in fusion with structurally hierarchical predictions (e.g., online learning predictions generated by an online ML model), such predictions can provide important cross-hierarchical conceptual inferences that can in turn facilitate efficient and effective classification in conceptually hierarchical domains. Thus, by generating structurally non-hierarchical predictions that can in turn be used in combination and/or in fusion with structurally hierarchical predictions, various embodiments of the present invention address technical challenges related to accounting for both hierarchical composition of the output space and cross-hierarchical composition of the output space when performing classification in hierarchical prediction domains. In doing so, various embodiments of the present invention make important technical contributions to efficiency and reliability of classification in hierarchical prediction domains, such as in classification in an HPO prediction domain.

FIG. 15 is a flowchart diagram of an example process 1500 for training a co-occurrence analysis ML model. Via the various steps/operations of process 1500, the model generation unit 115 of the classification computing entity 106 can train a co-occurrence analysis ML model configured to generate/predict accurate and reliable structurally non-hierarchical predictions based on prediction inputs associated with a hierarchical prediction space.

The process 1500 begins at step/operation 1501 when the model generation unit 115 prepares input training data. In some embodiments, to prepare the input training data, the model generation unit 115 retrieves raw training data 124 from the storage subsystem 108. The raw training data 124 may include, for each training entity (e.g., patient), one or more training features (e.g., medical codes) and one or more training prediction labels (e.g., one or more HPO labels), where at least one of the training prediction labels may be associated with a hierarchical predictive relationship.

At step/operation 1502, the model generation unit 115 constructs a co-occurrence matrix based on the input training data obtained in step/operation 1501. In some embodiments, each value in the co-occurrence matrix is determined based on a count of co-occurrence of a respective training feature and a respective prediction label in the input training data. For example, given the input data objects {B1, B2, B3→Y1}, {B1, B4, B5→Y1}, {B1, B3, B4→Y2}, {B1, B2, B5→Y2}, and {B1, B2, B4→Y2} (where {α, β, ç→ε} denotes that training features α, β, ç are associated with the training prediction label ε), the model generation unit 115 may generate the following co-occurrence matrix values (where M(α, ε) denotes a co-occurrence matrix value associated with the training feature a and the training prediction label M(B1, Y1)=2; M(B2, Y1)=1; M(B3, Y1)=1; M(B4, Y1)=1; M(B5, Y1)=1; M(B1, Y2)=3; M(B2, Y1)=2; M(B3, Y2)=1; M(B4, Y2)=2; and M(B5, Y2)=1.

FIG. 16 provides an operational example of a co-occurrence matrix 1600. In the example co-occurrence matrix 1600 of FIG. 16, each co-occurrence matrix value represents a magnitude (e.g., count) of co-occurrence of a particular training feature (i.e., an ICD value, represented by the columns 1601 of the co-occurrence matrix 1600) and a particular training prediction label (i.e., an HPO label, represented by the rows 1602 of the co-occurrence matrix). For example, based on the co-occurrence matrix 1600, the model generation unit 115 can infer that the magnitude of co-occurrence of training feature ICD-2 and HPO label HPO-20 is 82. As another example, based on the co-occurrence matrix 1600, the model generation unit 115 can infer that the magnitude of co-occurrence of training feature ICD-7 and HPO label HPO-20 is 92. As yet another example, based on the co-occurrence matrix 1600, the model generation unit 115 can infer that the magnitude of co-occurrence of training feature ICD-12 and HPO label HPO-20 is 59. As a further example, based on the co-occurrence matrix 1600, the model generation unit 115 can infer that the magnitude of co-occurrence of training feature ICD-15 and HPO label HPO-20 is b 28.

Returning to FIG. 15, at step/operation 1503, the model generation unit 115 performs one or more normalizations of the co-occurrence matrix generated in step/operation 1502 in order to generate a normalized co-occurrence matrix. In some embodiments, the model generation unit 115 performs at least one of row-wide normalizations and column-wide normalizations to perform the one or more normalizations of the co-occurrence matrix generated in step/operation 1502 in order to generate the mentioned normalized co-occurrence matrix. In some embodiments, the model generation unit 115 may perform normalizations across each group of consecutive n rows and/or each group of consecutive m columns, where at least one of n and m may be more than one. In some embodiments, at least one of n and m may be a preconfigured parameter and/or hyper-parameter of the co-occurrence analysis ML model, a preconfigured parameter and/or hyper-parameter of the particular training algorithm utilized by the model generation unit 115 to train the co-occurrence analysis ML model, a parameter and/or hyper-parameter of the co-occurrence analysis ML model determined by using a ML algorithm, a parameter and/or hyper-parameter of the particular training algorithm utilized by the model generation unit 115 to train the co-occurrence analysis ML model which is determined by using a ML algorithm, and/or the like.

In some embodiments, step/operation 1503 may be performed in accordance with the various steps/operations of the FIG. 17, which is a flowchart diagram of an example process for generating a normalized co-occurrence matrix. The example process depicted in FIG. 17 begins at step/operation 1701 when the model generation unit 115 obtains a co-occurrence matrix, e.g., the co-occurrence matrix 1600 of FIG. 16. At step/operation 1702, the model generation unit 1702 performs one or more row-wide normalizations of the co-occurrence matrix to generate a row-normalized co-occurrence matrix. In some embodiments, to perform a row-wide normalization of a particular row of the co-occurrence matrix, the model generation unit 115 applies a normalization parameter to each co-occurrence matrix value in the particular row, where the normalization parameter is determined based on a measure of statistical distribution (e.g., median, mean, mode, maximum value, minimum value, and/or the like.) of at least some co-occurrence matrix values in the particular row. In some embodiments, to perform a row-wide normalization of a particular row of the co-occurrence matrix, the model generation unit 115 divides each co-occurrence matrix value in the particular row by a measure of statistical distribution (e.g., median, mean, mode, maximum value, minimum value, and/or the like.) of the co-occurrence matrix values in the particular row. For example, to perform a row-wide normalization of a particular row of the co-occurrence matrix, the model generation unit 115 may divide each co-occurrence matrix value in the particular row by a maximum co-occurrence matrix value in the particular row. In some embodiments, to perform a row-wide normalization of a particular row of the co-occurrence matrix, the model generation unit 115 performs a softmax normalization of the co-occurrence matrix values in the particular row of the particular co-occurrence matrix.

At step/operation 1703, the training performs one or more column-wide normalizations of the row-normalized co-occurrence matrix generated in step/operation 1702 to generate a normalized co-occurrence matrix. In some embodiments, to perform a column-wide normalization of a particular column of the row-normalized co-occurrence matrix, the model generation unit 115 applies a normalization parameter to each row-normalized co-occurrence matrix value in the particular row, where the normalization parameter is determined based on a measure of statistical distribution (e.g., median, mean, mode, maximum value, minimum value, and/or the like.) of at least some row-normalized co-occurrence matrix values in the particular column. In some embodiments, to perform a column-wide normalization of a particular column of the co-occurrence matrix, the model generation unit 115 divides each row-normalized co-occurrence matrix value in the particular column by a measure of statistical distribution (e.g., median, mean, mode, maximum value, minimum value, and/or the like.) of the row-normalized co-occurrence matrix values in the particular column. For example, to perform a column-wide normalization of a particular column of the row-normalized co-occurrence matrix, the model generation unit 115 may divide each co-occurrence matrix value in the particular column by a maximum row-normalized co-occurrence matrix value in the particular column. In some embodiments, to perform a column-wide normalization of a particular column of the row-normalized co-occurrence matrix, the model generation unit 115 performs a softmax normalization of the row-normalized co-occurrence matrix values in the particular column of the row-normalized co-occurrence matrix.

Returning to FIG. 15, at step/operation 1504, the model generation unit 115 performs one or more significance-based filters of the normalized co-occurrence matrix generated in step/operation 1503 in order to generate a filtered co-occurrence matrix. In some embodiments, the to perform a significance-based filter of the normalized co-occurrence matrix, the model generation unit 115 may compute a non-parametric adjustment value for each normalized co-occurrence matrix value that describes at least one aspect of the significance of the normalized co-occurrence matrix value in its respective category (e.g., in its respective row and/or column of the normalized co-occurrence matrix) relative to the significance of other normalized co-occurrence matrix values in other respective categories. An example of a significance-based filter is a filter performed based on a chi-squared test analysis. While the example process 1500 depicts the significance-based filters of the co-occurrence matrix as being performed after co-occurrence matrix normalizations, one of ordinary skill in the art will recognize that some significance-based filters can be performed before co-occurrence matrix normalizations while other significance-based filters can be performed after co-occurrence matrix normalizations, and/or the like. In general, the model generation unit 115 may perform each of various co-occurrence matrix normalizations and various co-occurrence matrix significance-based filters in any order to generate a co-occurrence matrix as part of training a co-occurrence analysis ML model associated with the co-occurrence analysis unit 112. In some embodiments, the model generation unit 115 may utilize a training algorithm (e.g., a gradient method algorithm that utilizes an error function generated based on prediction scores determined with respect to ground-truth prediction data) to generate weights for each of various entries in a co-occurrence matrix and adjust the noted co-occurrence matrix entries according to their corresponding weight values.

Once trained by the model generation unit 115, the co-occurrence analysis ML model can be transmitted to an end user, e.g., an end-user associated with an external computing entity, such as an external computing entity 102 associated with a healthcare delivery organization, an external computing entity 102 associated with a health insurance provider organization, an external computing entity 102 associated with an auditing organization, an external computing entity 102 associated with a regulatory organization, and/or the like. Moreover, once trained by the model generation unit 115, the co-occurrence analysis ML model can be stored in a local and/or remote database, e.g., as part of the model definition data 123 for the co-occurrence analysis ML model in the storage subsystem 108.

The trained co-occurrence analysis ML model can be used by the co-occurrence analysis unit 112 of the classification computing entity 106 to generate predictions, such as predictions related to a hierarchical prediction domain. The normalization and filtering operations performed on the co-occurrence data by the model generation unit 115 are examples of computationally inexpensive operations configured to address complexities associated with translation of numeric patterns to conceptual predictive frameworks. Moreover, the co-occurrence model utilized by the co-occurrence analysis unit 112 may be configured to generate structurally non-hierarchical predictions that provide important cross-hierarchical insights that facilitate effective and efficient classification in hierarchical prediction domains.

FIG. 18 is a flowchart diagram of an example process 1800 for generating predictions using a trained co-occurrence analysis ML model. Via the various steps/operations of the process 1800, the co-occurrence analysis unit 112 of the classification computing entity 106 can generate structurally non-hierarchical predictions that facilitate effective and efficient classification in hierarchical prediction domains.

Process 1800 begins at step/operation 1801 when the co-occurrence analysis unit 112 obtains a trained co-occurrence analysis ML model. In some embodiments, to obtain the trained co-occurrence analysis ML model, the co-occurrence analysis unit 112 retrieves parameters and/or hyper-parameters associated with the co-occurrence analysis ML model from the model definition data 123 associated with the co-occurrence analysis ML model in the storage subsystem 108. In some embodiments, the co-occurrence analysis ML model is generated based on the co-occurrences of training features and training prediction labels among particular training data, e.g., particular raw training data 124 stored in the storage subsystem 108. In some embodiments, the co-occurrence analysis ML model is generated using a training process that involves one or more matrix normalizations and/or one or more matrix significance-based filters, e.g., the example process 1500 of FIG. 15.

At step/operation 1802, the co-occurrence analysis unit 112 obtains particular one or more prediction input features. In some embodiments, the particular prediction input features are associated with a particular predictive entity, which may be a real-world entity with respect to which a prediction is being performed. Examples of particular prediction input features for a particular predictive entity may be medical codes associated with a particular patient. In some embodiments, at least a portion of the particular prediction input features is obtained from an external computing entity 102, such as an external computing entity 102 associated with a healthcare delivery organization, an external computing entity 102 associated with a health insurance provider organization, an external computing entity 102 associated with an auditing organization, an external computing entity 102 associated with a regulatory organization, and/or the like. In some embodiments, at least a portion of the particular prediction input features is retrieved from a local and/or remote database, such as from the storage subsystem 108 of the classification system 101. In some embodiments, at least a portion of the particular prediction input features is stored in a prediction input data object. In some embodiments, the prediction input data object is a prediction input vector, e.g., an atomic m*/l vector stored as a one-dimensional array of size m and a vector in a prediction input in an m*n matrix including n vectors stored as a two-dimensional array of size m*n.

At step/operation 1803, the co-occurrence analysis unit 112 determines top M prediction labels for the prediction input features obtained in step/operation 1802. In some embodiments, to determine the top M prediction labels for the prediction input features obtained in step/operation 1802, the co-occurrence analysis unit 112 uses the trained co-occurrence matrix. For example, the co-occurrence analysis unit 112 may determine the top M prediction labels having the highest co-occurrence matrix values associated with a particular prediction input feature in the trained co-occurrence matrix obtained in step/operation 1801 as the top M prediction labels for the particular prediction input feature. In some embodiment, if the prediction input features obtained in step/operation 1802 include more than one features, the co-occurrence analysis unit 112 may determine the top M prediction labels having the highest co-occurrence matrix values associated with the at least one of the two or more particular prediction input features in the trained co-occurrence matrix obtained in step/operation 1801 as the top M prediction labels for the particular prediction input feature.

In some embodiments, M is an output diversity parameter for the co-occurrence analysis ML model. In some embodiments, the output diversity parameter for the co-occurrence analysis ML model may be a preconfigured parameter and/or hyper-parameter of the co-occurrence analysis ML model, a preconfigured parameter and/or hyper-parameter of the particular training algorithm utilized by the model generation unit 115 to train the co-occurrence analysis ML model, a parameter and/or hyper-parameter of the co-occurrence analysis ML model determined by using a ML algorithm, a parameter and/or hyper-parameter of the particular training algorithm utilized by the model generation unit 115 to train the co-occurrence analysis ML model which is determined by using a ML algorithm, and/or the like.

FIG. 19 provides an operational example of a co-occurrence values set 1900 for a training feature ICD-7. The co-occurrence values set 1900 include twenty co-occurrence values that each denote a magnitude of co-occurrence of the training feature ICD-7 with each of twenty training prediction labels, e.g., a normalized and/or significance-based filtered magnitude of co-occurrence of the training feature ICD-7 with each of twenty training prediction labels. The twenty co-occurrence values in the co-occurrence values set 1900 include a co-occurrence value 1901 (i.e., denoting a magnitude of co-occurrence of 96 between the training feature ICD-7 and a corresponding prediction label), a co-occurrence value 1902 (i.e., denoting a magnitude of co-occurrence of 92 between the training feature ICD-7 and a corresponding prediction label), a co-occurrence value 1903 (i.e., denoting a magnitude of co-occurrence of 84 between the training feature ICD-7 and a corresponding prediction label), and a co-occurrence value 1904 (i.e., denoting a magnitude of co-occurrence of 94 between the training feature ICD-7 and a corresponding prediction label).

In some embodiments, step/operation 1803 may be described with reference to the exemplary co-occurrence values set 1900 of FIG. 19. If the co-occurrence analysis unit 112 obtains a singular prediction input feature corresponding to ICD-17 in step/operation 1802, the co-occurrence analysis unit 112 may determine the top M prediction labels having the highest co-occurrence values as the prediction labels for the particular singular prediction input feature corresponding to ICD-17. For example, given M=1, the co-occurrence analysis unit 112 may determine the prediction label corresponding to the co-occurrence value 1901 as the selected prediction label for the particular singular prediction input feature, given that the co-occurrence value 1901 is the highest co-occurrence value in the co-occurrence values set 1900. As another example, given M=2, the co-occurrence analysis unit 112 may determine the prediction label corresponding to the co-occurrence values 1901 and 1902 as the selected prediction labels for the particular singular prediction input feature, given that the co-occurrence values 1901 and 1902 are the two highest co-occurrence values in the co-occurrence values set 1900. As yet another example, given M=3, the co-occurrence analysis unit 112 may determine the prediction label corresponding to the co-occurrence values 1901, 1902 and 1903 as the selected prediction labels for the particular singular prediction input feature, given that the co-occurrence values 1901, 1902 and 1903 are the three highest co-occurrence values in the co-occurrence values set 1900. As a further example, given M=4, the co-occurrence analysis unit 112 may determine the prediction label corresponding to the co-occurrence values 1901, 1902, 1903, and 1904 as the selected prediction labels for the particular singular prediction input feature, given that the co-occurrence values 1901, 1902, 1903, and 1904 are the four highest co-occurrence values in the co-occurrence values set 1900.

Importantly, selecting the prediction labels based on the co-occurrence values in the trained co-occurrence matrix requires a computationally inexpensive matrix traversal. Moreover, the generated prediction labels are structurally non-hierarchical predictions, given that they may be from any hierarchical level in a hierarchical prediction domains. Using these and other techniques, the co-occurrence analysis concepts discussed herein provide efficient and reliable solutions for classification using statistical ML solutions and/or classification in hierarchical prediction domains.

D. Fusion of Structurally Hierarchical Predictions and Structurally Non-Hierarchical Predictions As discussed above with reference to co-occurrence analysis ML models, in hierarchical prediction domains, the presence of hierarchical relationships between prediction nodes in the output space complicates the task of inferring a prediction output based on prediction scores for various prediction nodes. On the one hand, the hierarchical relationships between prediction nodes in the output space provide important domain information that can facilitate efficient and reliable predictive inferences. On the other hand, important predictive conclusions may be inferred from ignoring the hierarchical relationships, especially in instances where the available hierarchical models do not capture all of the relevant information about conceptual relationships between prediction nodes and/or include potentially erroneous information about conceptual relationships between prediction nodes. Thus, there is a continuing technical challenge associated with performing predictive analyses in a manner that takes into account both hierarchical composition of the output space and cross-hierarchical composition of the output space.

Various embodiments of the present invention address the mentioned technical challenges associated with considering both hierarchical composition of the output space and cross-hierarchical composition of the output space when performing classification in hierarchical prediction domains. For example, various embodiments of the present invention relate to co-occurrence analysis ML models that generate structurally non-hierarchical predictions. A structurally non-hierarchical prediction may be a prediction determined without regard to a position of the corresponding prediction node in a structural hierarchy characterizing the hierarchical prediction domain that includes the corresponding prediction node. For example, in some embodiments, a co-occurrence analysis ML model may be configured to generate the one or more co-occurrence analysis predictions based on prediction values for prediction nodes regardless of whether the prediction nodes are deemed to be dependent prediction nodes in a structurally hierarchy characterizing the prediction domain associated with the co-occurrence analysis ML model. In at least some of those embodiments, the co-occurrence analysis ML model may generate predictions that correspond to both most-dependent nodes and non-most-dependent nodes in the structural hierarchically characterizing the prediction domain associated with the online ML model.

By generating structurally non-hierarchical predictions, various embodiments of the present invention provide predictions that are agnostic to the hierarchical composition of the prediction output space. Such structurally non-hierarchical predictions can in turn be used in combination and/or in fusion with structurally hierarchical predictions, such as structurally hierarchical predictions generated by an online learning unit 111. When structurally non-hierarchical predictions are used in combination and/or in fusion with structurally hierarchical predictions are used to generate structure-based predictions, such structured-fused predictions can provide important cross-hierarchical conceptual inferences that can in turn facilitate efficient and effective classification in conceptually hierarchical domains. Various embodiments of the present invention provide efficient and reliable techniques for fusing structurally hierarchical predictions and structurally non-hierarchical predictions. Such solutions make important technical contributions to classification models in hierarchical prediction domains, as they enable such models to utilize both predictive insights provided by hierarchical relationships of the output space and predictive insights provided without taking hierarchical relationships among training data into account. In doing so, various embodiments of the present invention address key challenges related to efficiency and reliability of hierarchical predictive relationships.

FIG. 20 is a flowchart diagram of an example process 2000 for generating predictions based on structurally hierarchical predictions and structurally non-hierarchically predictions. Via the various steps/operations of process 2000, the structured fusion unit 113 of the classification computing entity 106 can fuse structurally hierarchical predictions and structurally non-hierarchical predictions in order to utilize both predictive insights provided by hierarchical relationships of the output space and predictive insights provided without taking hierarchical relationships among training data into account in making predictive inferences.

The process 2000 begins at step/operation 2001 when the structured fusion unit 113 obtains K structurally hierarchical predictions and M structurally non-hierarchical predictions, where each of K and M may be one or more. In some embodiments, at least some of the K structurally hierarchical predictions are generated by an online ML model. In some embodiments, at least some of the M structurally non-hierarchical predictions are generated by a con-occurrence analysis ML model. In some embodiments, at least some of the M structurally non-hierarchical predictions are generated by a ML model that utilizes at least one natural language processing algorithm. In some embodiments, K is determined based on at least one of a preconfigured parameter and/or hyper-parameter of an online ML model, a preconfigured parameter and/or hyper-parameter of a particular training algorithm utilized by the model generation unit 115 to train an online ML model, a parameter and/or hyper-parameter of an online ML model determined by using a ML algorithm, a parameter and/or hyper-parameter of a particular training algorithm utilized by the model generation unit 115 to train an online ML model which is determined by using a ML algorithm, and/or the like. In some embodiments, M is determined based on at least one of the following: a preconfigured parameter and/or hyper-parameter of a co-occurrence analysis ML model, a preconfigured parameter and/or hyper-parameter of a natural-language-processing-based model, a preconfigured parameter and/or hyper-parameter of a particular training algorithm utilized by the model generation unit 115 to train a co-occurrence analysis ML model, a preconfigured parameter and/or hyper-parameter of a particular training algorithm utilized by the model generation unit 115 to train a natural-language-processing-based model, a parameter and/or hyper-parameter of a co-occurrence analysis ML model determined by using a ML algorithm, a parameter and/or hyper-parameter of a natural-language-processing-based model determined by using a ML algorithm, a parameter and/or hyper-parameter of a particular training algorithm utilized by the model generation unit 115 to train a co-occurrence analysis ML model which is determined by using a ML algorithm, a parameter and/or hyper-parameter of a particular training algorithm utilized by the model generation unit 115 to train a natural-language-processing-based model which is determined by using a ML algorithm, and/or the like.

FIG. 21 provides an operational example of a structurally hierarchical prediction set 2100. The example structurally hierarchical prediction set 2100 includes five structurally hierarchical predictions generated by an FTRL ML model, each of which belongs to a relatively most-dependent prediction node in a hierarchical prediction domain associated with the structurally hierarchical prediction set 2100. The five structurally hierarchical predictions in the structurally hierarchical prediction set 2100 include: structurally hierarchical prediction 2101 corresponding to the prediction label HPO_0008; structurally hierarchical prediction 2102 corresponding to the prediction label HPO_0006; structurally hierarchical prediction 2103 corresponding to the prediction label HPO_0001; structurally hierarchical prediction 2104 corresponding to the prediction label HPO_0002; and structurally hierarchical prediction 2105 corresponding to the prediction label HPO_0004.

In some embodiments, the order of the structurally hierarchical predictions in the structurally hierarchical prediction set 2100 indicates an order of magnitudes of the respective structurally hierarchical predictions in the structurally hierarchical prediction set 2100. In some embodiments, the order of the structurally hierarchical predictions in the structurally hierarchical prediction set 2100 indicates an order of the hierarchical level the structurally hierarchical predictions in the structurally hierarchical prediction set 2100 starting from the most-dependent hierarchical level. In some embodiments, the order of the structurally hierarchical predictions in the structurally hierarchical prediction set 2100 indicates both an order of magnitudes of the respective structurally hierarchical predictions in the structurally hierarchical prediction set 2100 and an order of the hierarchical level the structurally hierarchical predictions in the structurally hierarchical prediction set 2100 starting from the most-dependent hierarchical level, such that the structurally hierarchical predictions are first ranked by the hierarchical level and then structurally hierarchical predictions belonging to the same hierarchical level are ranked by the magnitude of prediction scores for the respective structurally hierarchical predictions belonging to the same hierarchical level.

FIG. 22 provides an operational example of a structurally non-hierarchical prediction set 2200. The example structurally non-hierarchical prediction set 2200 includes five structurally hierarchical predictions generated by a co-occurrence analysis ML model, each of which may belong to any hierarchical level in a hierarchical prediction domain associated with the structurally non-hierarchical prediction set 2200. The five structurally hierarchical predictions in the structurally non-hierarchical prediction set 2200 include: structurally non-hierarchical prediction 2201 corresponding to the prediction label HPO_0002; structurally non-hierarchical prediction 2202 corresponding to the prediction label HPO_0021; structurally non-hierarchical prediction 2203 corresponding to the prediction label HPO_0211; structurally non-hierarchical prediction 2204 corresponding to the prediction label HPO_0003; and structurally non-hierarchical prediction 2205 corresponding to the prediction label HPO_0005. In some embodiments, the order of the structurally non-hierarchical predictions in the structurally non-hierarchical prediction set 2200 indicates an order of magnitudes of the respective structurally non-hierarchical predictions in the structurally non-hierarchical prediction set 2200.

Returning to FIG. 20, at step/operation 2002, the structured fusion unit 113 determines an up-weighting score for each structurally hierarchical prediction among the K structurally hierarchical predictions obtained in step/operation 2001. In some embodiments, to determine an up-weighting score for a particular structurally hierarchical prediction obtained in step/operation 2001, the structured fusion unit 113 determines a smallest degree of hierarchical separation between the particular structurally hierarchical prediction and a structurally non-hierarchical prediction among the M structurally non-hierarchical predictions obtained in step/operation 2002. The structured fusion unit 113 then determines the up-weighting score for the particular structurally hierarchical-prediction based on the determined smallest degree of hierarchical separation between the particular structurally hierarchical prediction and a structurally non-hierarchical prediction among the M structurally non-hierarchical predictions obtained in step/operation 2002.

For example, to determine an up-weighting score for a particular structurally hierarchical prediction obtained in step/operation 2001, the structured fusion unit 113 may first determine whether the particular structurally hierarchical prediction is among the M structurally non-hierarchical predictions obtained in step/operation 2002. If the structured fusion unit 113 determines that the particular structurally hierarchical prediction is among the M structurally non-hierarchical predictions obtained in step/operation 2002, the structured fusion unit 113 determines a highest possible up-weighting score J for the particular structurally hierarchical prediction. In some embodiments, if the structured fusion unit 113 determines that the particular structurally hierarchical prediction is not among the M structurally non-hierarchical predictions obtained in step/operation 2002, the structured fusion unit 113 determines if a parent of the particular structurally hierarchical prediction up to the Jth parent of the particular structurally hierarchical prediction is among the M structurally non-hierarchical predictions obtained in step/operation 2002. If the structured fusion unit 113 determines that a Dth parent of the particular structurally hierarchical prediction is among the M structurally non-hierarchical predictions obtained in step/operation 2002, where D<=J, the structured fusion unit 113 determines an up-weighting score of J−D for the particular structurally hierarchical prediction. However, if the structured fusion unit 113 determines that a Dth parent of the particular structurally hierarchical prediction is not among the M structurally non-hierarchical predictions obtained in step/operation 2002, where D<=J, the structured fusion unit 113 determines a smallest possible up-weighting score (e.g., an up-weighting score of zero) for the particular structurally hierarchical prediction. In some embodiments, if the structured fusion unit 113 determines that a Dth parent of the particular structurally hierarchical prediction is among the M structurally non-hierarchical predictions obtained in step/operation 2002, regardless of whether D<=J, the structured fusion unit 113 determines an up-weighting score of J−D for the particular structurally hierarchical prediction, a technique that may generate down weighing scores (i.e., negative up-weighting scores) for some structurally hierarchical predictions.

In some embodiments, step/operation 2002 may be described in reference to FIG. 23, which is an operational example of an up-weighting score generation data structure 2300. The example up-weighting score generation data structure 2300 determines a ranked list of structurally hierarchical predictions, whose ranking has been determined based on the ranking of the structurally hierarchical prediction set 2100 of FIG. 21. For each entry in the up-weighting score generation data structure 2300 corresponding to a particular structurally hierarchical prediction, an up-weighting score is calculated in the fourth column based on whether the particular structurally hierarchical prediction appears in the structurally non-hierarchical prediction set 2200 of FIG. 22, whether a parent prediction label of the particular structurally hierarchical prediction appears in the structurally non-hierarchical prediction set 2200 of FIG. 22, whether a grandparent prediction label of the particular structurally hierarchical prediction appears in the structurally non-hierarchical prediction set 2200 of FIG. 22, whether a great-grandparent prediction label of the particular structurally hierarchical prediction appears in the structurally non-hierarchical prediction set 2200 of FIG. 22, or whether a great-great-grandparent prediction label of the particular structurally hierarchical prediction appears in the structurally non-hierarchical prediction set 2200 of FIG. 22.

For example, in the up-weighting score generation data structure 2300 of FIG. 23, because the structurally non-hierarchical prediction 2203 is a grandparent of the structurally hierarchical prediction HPO_0006, and because the grandparent has a degree of separation of two from the structurally hierarchical prediction HPO_0006, the up-weighting score 2301 of 4−2=2 is calculated for the structurally hierarchical prediction HPO_0006. As another example, because prediction label 2104 is corresponds to the structurally hierarchical prediction HPO_0002, and because the structurally hierarchical prediction HPO_0002 has a degree of separation of zero from itself, the up-weighting score 2302 of 4−0=4 is calculated for the structurally hierarchical prediction HPO_0002. As a further example, because prediction label 2202 is a parent of the structurally hierarchical prediction HPO_0004, and because the parent has a degree of separation of one from the structurally hierarchical prediction HPO_0004, the up-weighting score 2303 of 4−1=2 is calculated for the structurally hierarchical prediction HPO_0004.

Returning to FIG. 20, at step/operation 2003, the structured fusion unit 113 applies the up-weighting factors determined in step/operation 2002 to the structurally hierarchical predictions obtained in step/operation 2001 to generate an up-weighted prediction score for each structurally hierarchical prediction. In some embodiments, to generate the up-weighed prediction scores for the structurally hierarchical predictions obtained in step/operation 2001, the structured fusion unit 113 increases a predictive score of each structurally hierarchical prediction (e.g., a predictive score determined using an online ML model) based on the up-weighting score for the respective structurally hierarchical prediction. In some embodiments, to generate the up-weighed prediction scores for the structurally hierarchical predictions obtained in step/operation 2001, the structured fusion unit 113 selects the structurally hierarchical predictions based on a selection order and, for each selected structurally hierarchical prediction, increases the rank of the structurally hierarchical prediction in a ranked list of structurally hierarchical predictions by the up-weighting score for the respective structurally hierarchical prediction to generate an updated ranked list of the structurally hierarchical predictions. In some embodiments, the selection order may be a randomized order of the structurally hierarchical predictions and/or an order determined based on one or more properties of the structurally hierarchical predictions. In some embodiments, after increasing the rank of the last structurally hierarchical prediction in the selection order of the structurally hierarchical prediction, the structured fusion unit 2001 generated the up-weighted prediction score for each structurally hierarchical prediction based on a ranked position of the respective structurally hierarchical prediction in the final updated ranking of the structurally hierarchical prediction resulting from adjusting the rank of the last structurally hierarchical prediction in the selection order for the structurally hierarchical predictions.

In some embodiments, step/operation 2003 can be described with reference to FIG. 24, which is an operational example of an up-weighting adjustment data structure 2400. The example up-weighting adjustment data structure 2400 includes the structurally hierarchical predictions from the structurally hierarchical prediction set 2100 of FIG. 21. However, the order of the structurally hierarchical predictions has been modified in accordance with the up-weighting scores for the structurally hierarchical predictions determined using the up-weighting score generation data structure 2300 of FIG. 23. For example, prediction label HPO_0002 which had a fourth-place ranking in the structurally hierarchical prediction set 2100 of FIG. 21 has been moved up four ranking positions to the first position in the up-weighting adjustment data structure 2400 based on the up-weighting score of 4 for the prediction label determined using the up-weighting score generation data structure 2300. As another example, prediction label HPO_0004 which had a fifth-place ranking in the structurally hierarchical prediction set 2100 of FIG. 21 has been moved up one ranking position to the fourth position in the up-weighting adjustment data structure 2400 based on the up-weighting score of 3 for the prediction label determined using the up-weighting score generation data structure 2300.

E. Fusion of Structure-Based Predictions and Non-Structure-Based Predictions

Various embodiments of the present invention are directed to classification in a hierarchical prediction domain by using at least one of structured input data and unstructured data. Structured data may refer to data that can be divided into semantically-defined data objects based on a predefined format of the data. Examples of structured data include data defined using a Structured Query Language (SQL), data defined using a file format language (such as the JavaScript Object Notation (JSON) language, a Comma-Separated Value (CSV) language, or an Extensible Markup Language (XML) language), and/or the like. In the healthcare context, structured data may include medical claims data, which may include information associated with each medical claim (e.g., information about time of a medical operation associated with a medical claim, one or more operation codes associated with a medical claim, cost of a medical operation associated with a medical, and/or the like.) in a structured format. Unstructured data may refer to data that cannot be divided into semantically-defined data objects based on a predefined format of the data. Examples of unstructured data include various types of natural language data, such as medical notes data which includes medical notes provided by a medical provider. Although various solutions exist for inferring semantically-defined data objects from unstructured data (such as various natural language processing solutions), such an inference is distinct from a straightforward division of structured data into semantically-defined data objects based on a predefined format of the structured data.

Both structured data and unstructured data provide valuable predictive insights for predictive analysis tasks, e.g., for predictive analysis tasks related to hierarchical prediction domains. For example, structured data can provide important insights about statistical distribution of features and prediction labels as well as sequential change of correlations between features and prediction labels over time. In some cases, structured data can provide insights that are out of the reach of semantically-unsophisticated and/or primarily-lexical natural language processing algorithms for processing structured data. On the other hand, when properly analyzed (e.g., when analyzed using semantically-sophisticated synonym-based natural language processing algorithms), unstructured data can provide a strong source of predictive insights about a predictive task associated with a hierarchical prediction domain.

Despite the complimentary utility of structured data and unstructured data in providing predictive insights relevant to classification in hierarchical prediction domains, the problem of efficiently and effectively integrating predictions derived from structured data (i.e., structure-based predictions) and predictions derived from unstructured data (i.e., non-structure-based predictions) is a non-trivial problem from a technical standpoint. Indeed, many conventional classification solutions fail to efficiently and reliably integrate structure-based predictions and non-structure-based predictions to generate predictive outputs. For example, a naive combination of particular structure-based predictions and non-structure-based predictions fails to properly appreciate the reciprocal implications of structure-based predictions and non-structure-based predictions for improving models utilized to generate each other. Indeed, one innovative aspect of the present invention relates to techniques for efficiently and reliably integrating structure-based predictions and non-structure-based predictions in a manner that causes at least one of the noted sets of predictions to provide feedback to a model utilized to generate the other.

Accordingly, various embodiments of the present invention address technical challenges related to efficient and reliable fusion of structure-based predictions and non-structure-based predictions by utilizing at least one of the noted sets of predictions to provide feedback to a model utilized to generate the other. For example, in some embodiments, non-structure-based predictions are used as ground-truth data to retrain one or more ML models utilized to generate structure-based predictions, e.g., one or more of an online ML model, a co-occurrence analysis ML model, and a structured fusion ML model. Through this and similar techniques, various embodiments of the present invention enable feedback-loop mechanism relationships between structure-based predictions and non-structure-based predictions which serve to render the models utilized to generate at least one of the structure-based predictions and the non-structure-based predictions more efficient (both in terms of training efficiency and in terms of inference efficiency) as well as more reliable. Thus, by utilizing at least one of the noted sets of predictions to provide feedback to a model utilized to generate the other, various embodiments of the present invention address technical challenges related to efficient and reliable fusion of structure-based predictions and non-structure-based predictions and make substantial technical improvements to conventional solutions for classification, such as conventional solutions for classification in hierarchical prediction domains.

FIG. 25 provides a flowchart diagram of an example process 2500 for performing an unstructured fusion of structure-based predictions generated using structured data and non-structure-based predictions generated using unstructured data. Via the various steps/operations of the process 2500, the unstructured fusion unit 114 of the classification computing entity 106 can perform unstructured fusions in a manner that enables feedback-loop mechanism relationships between structure-based predictions and non-structure-based predictions, which in turn serves to render the ML models utilized to generate at least one of the structure-based predictions and the non-structure-based predictions more efficient.

The process 2500 begins at step/operation 2501 when the unstructured fusion unit 114 obtains non-structure-based predictions for a predictive entity. In some embodiments, the unstructured fusion unit 114 receives at least some of the non-structure-based predictions from an external computing entity 102, such as an external computing entity 102 associated with a healthcare delivery organization, an external computing entity 102 associated with a health insurance provider organization, an external computing entity 102 associated with an auditing organization, an external computing entity 102 associated with a regulatory organization, and/or the like. In some embodiments, the unstructured fusion unit 114 retrieves at least some of the non-structure-based predictions from the storage subsystem 108, e.g., from the unstructured input data 122 stored on the storage subsystem 108.

In some embodiments, the unstructured fusion unit 114 generates at least some of the non-structure-based predictions, e.g., by applying one or more natural language processing algorithms to one or more unstructured prediction inputs such as one or more synonym-based natural language processing algorithms. In some embodiments, to generate at least some of the non-structure-based predictions as part of the step/operation 2501, the structured fusion unit 113 performs the various steps/operations of FIG. 26, which is a flowchart diagram of an example process for generating structurally non-hierarchical predictions based on unstructured prediction inputs.

The example process depicted in FIG. 26 begins at step/operation 2601 when the unstructured fusion unit 114 processes unstructured input data entries to extract noun chunks from the unstructured input data entries. In some embodiments, the unstructured fusion unit 114 identifies all noun chunks in the unstructured input data entries based on presence of one or more separator characters (e.g., whitespace character, the dot character, the comma character, and/or the like.) in the unstructured input data entries. In some embodiments, the unstructured fusion unit 114 performs a search of the unstructured input data entries to determine instances of occurrences of particular preconfigured terms among the unstructured input data entries. The particular preconfigured terms may be received from an external computing entity 102 and/or from the model definition data 123 for the unstructured fusion ML model utilized by the unstructured fusion unit 114. In some embodiments, the unstructured fusion unit 114 identifies all noun chunks in the unstructured input data entries and subsequently determines which of the noun chunks correspond to preconfigured terms.

In some embodiments, step/operation 2601 may be described with reference to aspects of FIG. 27, which provides an operational example of an unstructured input data object 2700. The example an unstructured input data object 2700 depicted in FIG. 27 includes a bullet list entry 2701. In the bullet list entry 2701, the unstructured fusion unit 114 has identified the following preconfigured terms: the preconfigured term 2711 ("renal dysplasia"), the preconfigured term 2712 ("rapid progression"), and the preconfigured term 2713 ("hearing loss"). In some embodiments, terms such as renal dysplasia, rapid progression, and hearing loss may be deemed to have semantic significance based on model definition data 123 associated with the unstructured fusion ML model utilized by the unstructured fusion unit 114.

Returning to FIG. 26, at step/operation 2602, the unstructured fusion unit 114 maps each extracted noun chunk generated in step/operation 2601 to a vector space. In some embodiments, the unstructured fusion unit 114 identifies a vector space having l dimensions, where each of the l dimensions is associated with one or more features. The unstructured fusion unit 114 generates, for each particular dimension of the l dimensions and each particular extracted noun, one or more particular feature values for the particular extracted noun chunks which correspond to the one or more feature values for the particular dimension. Then, the unstructured fusion unit 114 determines a value for the dimension and for particular extracted noun based on the one or more particular feature values for the particular extracted noun chunks which correspond to the one or more feature values for the particular dimension. In some embodiments, at least some of the l dimensions of the vector space discussed above and/or at least some of the dimension values for particular noun chunks are determined using one or more feature embedding algorithms. In some embodiments, at least some of the l dimensions of the vector space discussed above are determined based on two or more dimensionally-reduced features and/or by utilizing at least one dimensionality reduction process.

In some embodiments, aspects of the step/operation 2602 may be performed in accordance with aspects of the unstructured input data object 2700 which includes, in addition to the bullet list entry 2701, an unstructured prediction entry 2721-2723 for each extracted noun-chunk 2711-2713. Each unstructured prediction entry 2721-2723 corresponding to an extracted noun-chunk 2711-713 includes a feature vector for the extracted noun-chunk 2711-2713 which includes the dimension values for the extracted noun-chunk 2711-2713 in a vector space associated with the extracted noun-chunks 2711-2713. For example, as indicated in the unstructured prediction entry 2721, the extracted noun chunk 2711 (associated with the term "renal dysplasia") is associated with the feature vector [27::42]. As another example, as indicated in the unstructured prediction entry 2722, the extracted noun chunk 2712 (associated with the term "rapid progression") is associated with the feature vector [150::167]. As a further example, as indicated in the unstructured prediction entry 2723, the extracted noun chunk 2713 (associated with the term "hearing loss") is associated with the feature vector [171::183].

The feature vectors generated for each extracted noun chunk generated in step/operation 2601 are then used to determine a position of each extracted noun chunk in a vector space. FIG. 28 provides an operational example of a non-structure-based prediction vector space 2800 having three dimensions 2801, 2802, and 2803 as well as two points 2811 and 2812. In the non-structure-based prediction vector space 2800 of FIG. 28, the point 2811 indicates position of the term "rental dysplasia" in relation to each of the three dimensions 2801, 2802, and 2803. Furthermore, the point 2811 indicates position of the term "branchio-ato-rental dysplasia" in relation to each of the three dimensions 2801, 2802, and 2803.

Returning to FIG. 26, at step/operation 2603, the unstructured fusion unit 114 generates non-structure-based predictions based on the vector space generated in step/operation 2602. In some embodiments, the unstructured fusion unit 114 applies one or more natural language processing algorithms to vector space values associated with the extracted noun-chunks to determine non-structure-based predictions based on the vector space. For example, the unstructured fusion unit 114 may determine HPO prediction label as non-structure-based predictions based on the vector space. Examples of HPO prediction labels generated as non-structure-based predictions are depicted in the unstructured prediction entries 2721-2723 of the unstructured input data object 2700 of FIG. 27. As depicted in the unstructured input data object 2700 of FIG. 27, the unstructured prediction entry 2721 includes the HPO prediction label HPO_0000110 for the preconfigured term 2711 (associated with the term "rental dysplasia"); the unstructured prediction entry 2722 includes the HPO prediction label HPO_0003678 for the preconfigured term 2712 (associated with the term "rapid progression"); and the unstructured prediction entry 2723 includes the HPO prediction label HPO_0000365 for the preconfigured term 2713 (associated with the term "hearing loss").

Returning to FIG. 25, at step/operation 2502, the unstructured fusion unit 114 uses the non-structure-based predictions obtained in step/operation 2501 as ground-truth prediction labels to retrain at least one structure-based ML model used to generate structure-based predictions and generate new structure-based predictions. In some embodiments, the unstructured fusion unit 114 retrains some or all of the structure-based ML models used to generate structure-based predictions. Then, the unstructured fusion unit 114 uses the retrained structure-based models to generate new structure-based predictions. Aspects of the step/operation 1502 provide a feedback-loop mechanism where non-structure-based predictions are used to optimize and improve structure-based ML models. As discussed above and further discussed below, this addresses a major technical challenge associated with unstructured fusion of structure-based predictions and non-structure-based predictions.

Despite the complimentary utility of structured data and unstructured data in providing predictive insights relevant to classification in hierarchical prediction domains, the problem of efficiently and effectively integrating predictions derived from structured data (i.e., structure-based predictions) and predictions derived from unstructured data (i.e., non-structure-based predictions) is a non-trivial problem from a technical standpoint. Indeed, many conventional classification solutions fail to efficiently and reliably integrate structure-based predictions and non-structure-based predictions to generate predictive outputs. For example, a naive combination of particular structure-based predictions and non-structure-based predictions fails to properly appreciate the reciprocal implications of structure-based predictions and non-structure-based predictions for improving models utilized to generate each other. Indeed, one innovative aspect of the present invention relates to techniques for efficiently and reliably integrating structure-based predictions and non-structure-based predictions in a manner that causes at least one of the noted sets of predictions to provide feedback to a model utilized to generate the other.

Accordingly, various embodiments of the present invention address technical challenges related to efficient and reliable fusion of structure-based predictions and non-structure-based predictions by utilizing at least one of the noted sets of predictions to provide feedback to a model utilized to generate the other. For example, in some embodiments, non-structure-based predictions are used as ground-truth data to retrain one or more ML models utilized to generate structure-based predictions, e.g., one or more of an online ML model, a co-occurrence analysis ML model, and a structured fusion ML model. Through this and similar techniques, various embodiments of the present invention enable feedback-loop mechanism relationships between structure-based predictions and non-structure-based predictions which serve to render the models utilized to generate at least one of the structure-based predictions and the non-structure-based predictions more efficient (both in terms of training efficiency and in terms of inference efficiency) as well as more reliable. Thus, by utilizing at least one of the noted sets of predictions to provide feedback to a model utilized to generate the other, various embodiments of the present invention address technical challenges related to efficient and reliable fusion of structure-based predictions and non-structure-based predictions and make substantial technical improvements to conventional solutions for classification, such as conventional solutions for classification in hierarchical prediction domains.

At step/operation 2503, the unstructured fusion unit 114 generates unstructured-fused predictions based on the non-structure-based predictions obtained in step/operation 2501 and the structure-based predictions generated in step/operation 2502. In some embodiments, the unstructured fusion unit 114 combines at least a portion of the non-structure-based predictions obtained in step/operation 2501 and at least a portion of the structure-based predictions generated in step/operation 2502 to generate unstructured-fused predictions. In some embodiments, step/operation 2503 can be performed in accordance with FIG. 29, which is a flowchart diagram of an example process for generating unstructured-fused predictions. The example process depicted in FIG. 29 begins at step/operation 2901 when the unstructured fusion unit 114 obtains structure-based predictions. At step/operation 2902, the unstructured fusion unit 114 obtains structure-based predictions. At step/operation 2902, the unstructured fusion unit 114 obtains non-structure-based predictions. At step/operation 2903, the unstructured fusion unit 114 selects all of the non-structure-based predictions and top V structure-based predictions having the highest prediction score and/or prediction rank as the unstructured fused predictions. In some embodiments, the selection of all of the nonstructure-based predictions as unstructured fused predictions may be based on an assumption of reliability of natural language processing algorithms utilized to generate the mentioned non-structure-based predictions, e.g., reliability of synonym-based natural language processing algorithms utilized to generate the mentioned non-structure-based predictions.

In some embodiments, V is a structure-based selection capacity parameter for the unstructured fusion ML model. In some embodiments, the structure-based selection capacity parameter is determined based on a preconfigured parameter and/or hyper-parameter of the unstructured fusion ML model, a preconfigured parameter and/or hyper-parameter of a particular training algorithm utilized by the model generation unit 115 to train the unstructured fusion ML model, a parameter and/or hyper-parameter of the unstructured fusion ML model determined by using a ML algorithm, a parameter and/or hyper-parameter of a particular training algorithm utilized by the model generation unit 115 to train the unstructured fusion ML model which is determined by using a ML algorithm, and/or the like. In some embodiments, the unstructured-fused predictions may retrieve the structure-based selection capacity parameter for the unstructured fusion ML model as part of the model definition data 123 for the unstructured fusion ML model.

F. HPO Label Prediction

HPO label prediction is an example of a prediction task related to a hierarchical prediction domain. As discussed above and further described below, the hierarchical prediction domains such as the HPO label domain present significant problems for various classification approaches. Examples of these challenges include challenges associated with structural complexity of the output space of such hierarchical prediction domains as well as challenges associated with complexity of input space of hierarchical prediction domains. Accordingly, to perform HPO label prediction using structured medical data and unstructured medical data, there is a need for predictive analysis solutions that address the complexities associated with the HPO label space as well as the complexities associated with processing both structured medical data and unstructured medical data.

To perform predictions in a hierarchical prediction domains using structured input data and/or unstructured input data, various embodiments of the present invention propose various arrangements of one or more of the following ML models: an online ML model for processing structured input data to generate structure-based predictions, a co-occurrence analysis ML model for processing structured input data to generate structure-based predictions, a structured fusion ML model for combining structure-based predictions, and an unstructured fusion ML model for combining structure-based predictions and non-structure-based predictions. In some embodiments, at least two of the mentioned ML models are organized in an ensemble architecture to generate a final prediction based on predictions of the at least two ML models. In some embodiments, all of the mentioned ML models are organized in an ensemble architecture to generate a final prediction based on predictions of the at least two ML models. Such ensemble architectures provide efficient and reliable solutions for classification in hierarchical prediction domain, such as for HPO label prediction in relation to the HPO label domain.

In addition, hierarchical prediction domains like the HPO domain present unique challenges for online learning algorithms. When utilized to generate predictions related to hierarchical prediction domains, online learning algorithms should accommodate hierarchical predictive relationships between various prediction nodes in determining how to interpret incoming training data. Without applying appropriate operational adjustments that address hierarchical nature of a relevant prediction domain, online learning algorithms will require higher amounts of training data, will take longer to train, and will once trained be less accurate and reliable. Because of those challenges, various existing online learning algorithms are ill-suited for efficiently and reliably performing classification in relation to hierarchical prediction domains.

Various embodiments of the present invention address efficiency and reliability challenges related to utilizing online learning algorithms to generate predictions related to hierarchical prediction domains. According to one aspect that relates to improving efficiency and reliability of online learning in hierarchical prediction domains, various embodiments of the present invention eliminate a bias term used to penalize lack of selection of a prediction node, as hierarchical predictive relationships complicate implications of such a lack of selection for adjusting model parameters. For example, selection of a prediction node may have different implications for prediction nodes that are dependent on the particular prediction node, prediction nodes from which the particular prediction node depends, and other prediction nodes without hierarchical relationships with the particular prediction node. To address such complications, various embodiments of the present invention will not penalize lack of selection of a particular node when adjusting parameters of a relevant ML model. In doing so, various embodiments of the present invention address efficiency and reliability challenges related to utilizing online learning algorithms to generate predictions related to hierarchical prediction domains, such generating HPO label predictions related to the HPO label domain.

Next, some aspects of the co-occurrence analysis ML models described herein include important contributions to efficiency and reliability of ML in hierarchical prediction domains, such as the HPO prediction domain. In hierarchical prediction domains, the presence of hierarchical relationships between prediction nodes in the output space complicates the task of inferring a prediction output based on prediction scores for various prediction nodes. On the one hand, the hierarchical relationships between prediction nodes in the output space provide important domain information that can facilitate efficient and reliable predictive inferences. On the other hand, important predictive conclusions may be inferred from ignoring the hierarchical relationships, especially in instances where the available hierarchical models do not capture all of the relevant information about conceptual relationships between prediction nodes and/or include potentially erroneous information about conceptual relationships between prediction nodes. Thus, there is a continuing technical challenge associated with performing predictive analyses in a manner that takes into account both hierarchical composition of the output space and cross-hierarchical composition of the output space.

Various embodiments of the present invention address the mentioned technical challenges associated with considering both hierarchical composition of the output space and cross-hierarchical composition of the output space when performing classification in hierarchical prediction domains. For example, various embodiments of the present invention relate to co-occurrence analysis ML models that generate structurally non-hierarchical predictions. A structurally non-hierarchical prediction may be a prediction determined without regard to a position of the corresponding prediction node in a structural hierarchy characterizing the hierarchical prediction domain that includes the corresponding prediction node. By generating structurally non-hierarchical predictions, various embodiments of the present invention provide predictions that are agnostic to the hierarchical composition of the prediction output space. When used in combination and/or in fusion with structurally hierarchical predictions (e.g., online learning predictions generated by an online ML model), such predictions can provide important cross-hierarchical conceptual inferences that can in turn facilitate efficient and effective classification in conceptually hierarchical domains. Thus, by generating structurally non-hierarchical predictions that can in turn be used in combination and/or in fusion with structurally hierarchical predictions, various embodiments of the present invention address technical challenges related to accounting for both hierarchical composition of the output space and cross-hierarchical composition of the output space when performing classification in hierarchical prediction domains. In doing so, various embodiments of the present invention make important technical contributions to efficiency and reliability of classification in hierarchical prediction domains, such as in classification in an HPO prediction domain and with respect to the HPO label prediction predictive task.

Furthermore, hierarchical prediction domains like the HPO prediction domain present challenges related to fusion of structurally hierarchical predictions and non-structurally hierarchical predictions. By generating structurally non-hierarchical predictions, various embodiments of the present invention provide predictions that are agnostic to the hierarchical composition of the prediction output space. Such structurally non-hierarchical predictions can in turn be used in combination and/or in fusion with structurally hierarchical predictions, such as structurally hierarchical predictions generated by an online learning unit 111. When structurally non-hierarchical predictions are used in combination and/or in fusion with structurally hierarchical predictions are used to generate structure-based predictions, such structured-fused predictions can provide important cross-hierarchical conceptual inferences that can in turn facilitate efficient and effective classification in conceptually hierarchical domains. Various embodiments of the present invention provide efficient and reliable techniques for fusing structurally hierarchical predictions and structurally non-hierarchical predictions. Such solutions make important technical contributions to classification models in hierarchical prediction domains, as they enable such models to utilize both predictive insights provided by hierarchical relationships of the output space and predictive insights provided without taking hierarchical relationships among training data into account. In doing so, various embodiments of the present invention address key challenges related to efficiency and reliability of classification in hierarchical prediction domains, such as the efficiency and reliability of HPO label prediction.

Moreover, hierarchical prediction domains like the HPO domain present challenges related to fusion of structure-based predictions and non-structure-based predictions. Both structured data and unstructured data provide valuable predictive insights for predictive analysis tasks, e.g., for predictive analysis tasks related to hierarchical prediction domains. However, despite the complimentary utility of structured data and unstructured data in providing predictive insights relevant to classification in hierarchical prediction domains, the problem of efficiently and effectively integrating predictions derived from structured data (i.e., structure-based predictions) and predictions derived from unstructured data (i.e., non-structure-based predictions) is a non-trivial problem from a technical standpoint. Indeed, many conventional classification solutions fail to efficiently and reliably integrate structure-based predictions and non-structure-based predictions to generate predictive outputs. For example, a naive combination of particular structure-based predictions and non-structure-based predictions fails to properly appreciate the reciprocal implications of structure-based predictions and non-structure-based predictions for improving models utilized to generate each other. Indeed, one innovative aspect of the present invention relates to techniques for efficiently and reliably integrating structure-based predictions and non-structure-based predictions in a manner that causes at least one of the noted sets of predictions to provide feedback to a model utilized to generate the other.

Accordingly, various embodiments of the present invention address technical challenges related to efficient and reliable fusion of structure-based predictions and non-structure-based predictions by utilizing at least one of the noted sets of predictions to provide feedback to a model utilized to generate the other. For example, in some embodiments, non-structure-based predictions are used as ground-truth data to retrain one or more ML models utilized to generate structure-based predictions, e.g., one or more of an online ML model, a co-occurrence analysis ML model, and a structured fusion ML model. Through this and similar techniques, various embodiments of the present invention enable feedback-loop mechanism relationships between structure-based predictions and non-structure-based predictions which serve to render the models utilized to generate at least one of the structure-based predictions and the non-structure-based predictions more efficient (both in terms of training efficiency and in terms of inference efficiency) as well as more reliable. Thus, by utilizing at least one of the noted sets of predictions to provide feedback to a model utilized to generate the other, various embodiments of the present invention address technical challenges related to efficient and reliable fusion of structure-based predictions and non-structure-based predictions and make substantial technical improvements to conventional solutions for classification, such as conventional solutions for classification in hierarchical prediction domains.

FIG. 30 is a flowchart diagram of an example process 3000 for performing HPO-based predictions. Via the various steps/operations of process 3000, the system interaction unit 116 of the classification computing entity 106 can perform efficient and reliable classification to generate HPO predictions and can effectively utilize the HPO predictions to generate precision medicine analytics.

The process 3000 starts at step/operation 3001 when the system interaction unit 116 obtains HPO label predictions for a number of patients. In some embodiments, the system interaction unit 116 generates at least some of the HPO label prediction labels using one or more of the ML models discussed above, e.g., using the ensemble architecture 410 depicted in FIG. 4A and/or the ensemble architecture 450 depicted in FIG. 4B. In some embodiments, at least some of the HPO label prediction labels is obtained from an external computing entity 102, such as an external computing entity 102 associated with a healthcare delivery organization, an external computing entity 102 associated with a health insurance provider organization, an external computing entity 102 associated with an auditing organization, an external computing entity 102 associated with a regulatory organization, and/or the like. In some embodiments, at least some of the HPO label prediction labels is retrieved from a local and/or remote database, such as from the storage subsystem 108 of the classification system 101.

At step/operation 3002, the system interaction unit 116 processes the HPO label predictions to generate a standardized genetic testing framework. In some embodiments, the system interaction unit 116 applies a standardization model to the HPO label predictions to generate a standardized genetic testing framework, where the standardization model may be obtained from an external computing entity, may be retrieved from the model definition data 123 stored on the storage subsystem, may be retrieved from a local and/or remote database, and/or the like. In some embodiments, the system interaction unit 116 provides the standardized genetic testing framework to at least one external computing entity 102 and/or stores the standardized genetic testing framework on the storage subsystem 108.

At step/operation 3003, the system interaction unit 116 processes the HPO label predictions to generate an integrated genomic record repository. Examples of data in the integrated genomic data repository include the patient-specific medical code record 3100 of FIG. 31, the patient-specific phenotypical record 3200 of FIG. 32, and the cross-patient holistic record 3300 of FIG. 33. In some embodiments, the system interaction unit 116 provides the integrated genomic record repository to at least one external computing entity 102 and/or stores the integrated genomic record repository on the storage subsystem 108. At step/operation 3004, the system interaction unit 116 processes the HPO label predictions to generate precision medicine analytics. In some embodiments, the precision medicine analytics include one or more cross-patient conclusions about health patterns and/or health-related correlations among a group of patients. In some embodiments, the system interaction unit 116 provides the precision medicine analytics to at least one external computing entity 102 and/or stores the precision medicine analytics on the storage subsystem 108. As depicted, each cross-patient holistic record entry of the cross-patient holistic record 3300 of FIG. 33 includes a binary (i.e., 0 or 1) field that denotes whether a particular predictive entity (e.g., a particular patient) is predicted to have a particular prediction label (e.g., a particular HPO). In some embodiments, each cross-patient holistic record entry is colored according to whether the corresponding binary field for the particular cross-patient holistic record denotes a positive or a negative prediction (e.g., using a green color for a positive prediction and a red color for a negative prediction).

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Although example processing systems have been described in the figures herein, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer-readable storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer-readable storage medium can be, or be included in, a computer-readable storage device, a computer-readable storage substrate, a random or serial access memory array or device, or a combination of one or more of them. Moreover, while a computer-readable storage medium is not a propagated signal, a computer-readable storage medium can be a source or destination of computer program instructions encoded in an artificially-generated propagated signal. The computer-readable storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

A computing entity is an example of a data processing apparatus. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (Field Programmable Gate Array) or an ASIC (Application Specific Integrated Circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory, a random access memory, or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (Cathode Ray Tube) or LCD (Liquid Crystal Display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client device having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., a Hypertext Markup Language (HTML) page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any inventions or of what may be claimed, but rather as description of features specific to particular embodiments of particular inventions. Certain features that are described herein in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results, unless described otherwise. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results, unless described otherwise. In certain implementations, multitasking and parallel processing may be advantageous.

The invention claimed is:

1. A computer-implemented method comprising:
receiving, by one or more processors and based at least in part on one or more prediction inputs, a plurality of structurally hierarchical predictions based at least in part on hierarchical predictive positions of a plurality of prediction nodes, wherein the plurality of structurally hierarchical predictions is generated by a first machine learning model by:
generating, using a second machine learning model and based at least in part on unstructured input data of the one or more prediction inputs, one or more non-structure-based predictions; and
generating, using the first machine learning model, the plurality of structurally hierarchical predictions based on the one or more non-structure-based predictions;

identifying, by the one or more processors and based at least in part on the plurality of structurally hierarchical predictions, a structurally hierarchical prediction set comprising one or more of the plurality of structurally hierarchical predictions that are ranked based at least in part on the hierarchical predictive positions;

receiving, by the one or more processors and based at least in part on one or more of the one or more prediction inputs, a structurally non-hierarchical prediction set that comprises one or more structurally non-hierarchical predictions ranked based at least in part on a predictive magnitude corresponding to each of the one or more structurally non-hierarchical predictions without regard to the hierarchical predictive positions;

generating, by the one or more processors and based at least in part on the structurally non-hierarchical prediction set, one or more up-weighting scores for the plurality of structurally hierarchical predictions based at least in part on a correspondence between the plurality of structurally hierarchical predictions and the one or more structurally non-hierarchical predictions, wherein an up-weighting score for a structurally hierarchical prediction is based at least in part on a degree of separation between the structurally hierarchical prediction and a corresponding structurally non-hierarchical prediction of the one or more structurally non-hierarchical predictions; and generating, by the one or more processors, a reranked structurally hierarchical prediction set by reranking the plurality of structurally hierarchical predictions of the structurally hierarchical prediction set based at least in part on the one or more up-weighting scores.

2. The computer-implemented method of claim 1, wherein the first machine learning model comprises a follow-the-regularized leader machine learning model.

3. The computer-implemented method of claim 1, wherein the one or more prediction inputs comprise one or more unstructured prediction inputs and one or more structured prediction inputs; and the computer-implemented method further comprises:
    generating a predictive output based at least in part on the reranked structurally hierarchical prediction set by:
        generating one or more structure-based predictions based at least in part on the one or more structured prediction inputs;
        generating one or more non-structure-based predictions based at least in part on the one or more unstructured prediction inputs; and
        generating, using an unstructured fusion machine learning model, the predictive output based at least in part on the one or more non-structure-based predictions in addition to the one or more structure-based predictions.

4. The computer-implemented method of claim 3, wherein:
    the one or more prediction inputs comprise one or more medical feature inputs for a patient profile, and
    the predictive output comprises at least one human phenotype ontology label prediction for the patient profile.

5. A system comprising at least one memory and one or more processors communicably coupled with the at least one memory, the one or more processors configured to:
    receive, based at least in part on one or more prediction inputs, a plurality of structurally hierarchical predictions based at least in part on hierarchical predictive positions of a plurality of prediction nodes, wherein the plurality of structurally hierarchical predictions is generated by a first machine learning model by:
        generating, using a second machine learning model and based at least in part on unstructured input data of the one or more prediction inputs, one or more non-structure-based predictions; and
        generating, using the first machine learning model, the plurality of structurally hierarchical predictions based on the one or more non-structure-based predictions;
    identify, based at least in part on the plurality of structurally hierarchical predictions, a structurally hierarchical prediction set comprising one or more of the plurality of structurally hierarchical predictions that are ranked based at least in part on the hierarchical predictive positions;
    receive, based at least in part on one or more of the one or more prediction inputs, a structurally non-hierarchical prediction set that comprises one or more structurally non-hierarchical predictions ranked based at least in part on a predictive magnitude corresponding to each of the one or more structurally non-hierarchical predictions without regard to the hierarchical predictive positions;
    generate, based at least in part on the structurally non-hierarchical prediction set, one or more up-weighting scores for the plurality of structurally hierarchical predictions based at least in part on a correspondence between the plurality of structurally hierarchical predictions and the one or more structurally non-hierarchical predictions, wherein an up-weighting score for a structurally hierarchical prediction is based at least in part on a degree of separation between the structurally hierarchical prediction and a corresponding structurally non-hierarchical prediction of the plurality of structurally non-hierarchical predictions; and
    generate a reranked structurally hierarchical prediction set by reranking the one or more structurally hierarchical predictions of the structurally hierarchical prediction set based at least in part on the one or more up-weighting scores.

6. The system of claim 5, wherein the first machine learning model comprises a follow-the-regularized leader machine learning model.

7. The system of claim 5, wherein the one or more prediction inputs comprise one or more unstructured prediction inputs and one or more structured prediction inputs; and the one or more processors are further configured to:
    generate a predictive output based at least in part on the reranked structurally hierarchical prediction set by:
        generating one or more structure-based predictions based at least in part on the one or more structured prediction inputs;
        generating one or more non-structure-based predictions based at least in part on the one or more unstructured prediction inputs; and
        generating, using an unstructured fusion machine learning model, the predictive output based at least in part on the one or more non-structure-based predictions in addition to the one or more structure-based predictions.

8. The system of claim 7, wherein:
    the one or more prediction inputs comprise one or more medical feature inputs for a patient profile, and
    the predictive output comprises at least one human phenotype ontology label prediction for the patient profile.

9. One or more non-transitory computer storage media including instructions that, when executed by one or more processors, cause the one or more processors to:
  receive, based at least in part on one or more prediction inputs, a plurality of structurally hierarchical predictions based at least in part on hierarchical predictive positions of a plurality of prediction nodes, wherein the plurality of structurally hierarchical predictions is generated by a first machine learning model by:
    generating, using a second machine learning model and based at least in part on unstructured input data of the one or more prediction inputs, one or more non-structure-based predictions; and
    generating, using the first machine learning model, the plurality of structurally hierarchical predictions based on the one or more non-structure-based predictions;
  identify, based at least in part on the plurality of structurally hierarchical predictions, a structurally hierarchical prediction set comprising one or more of the plurality of structurally hierarchical predictions that are ranked based at least in part on the hierarchical predictive positions;
  receive, based at least in part on one or more of the one or more prediction inputs, a structurally non-hierarchical prediction set that comprises one or more structurally non-hierarchical predictions ranked based at least in part on a predictive magnitude corresponding to each of the one or more structurally non-hierarchical predictions without regard to the hierarchical predictive positions;
  generate, based at least in part on the structurally non-hierarchical prediction set, one or more up-weighting scores for the plurality of structurally hierarchical predictions based at least in part on a correspondence between the plurality of structurally hierarchical predictions and the one or more structurally non-hierarchical predictions, wherein an up-weighting score for a structurally hierarchical prediction is based at least in part on a degree of separation between the structurally hierarchical prediction and a corresponding structurally non-hierarchical prediction of the one or more structurally non-hierarchical predictions; and
  generate a reranked structurally hierarchical prediction set by reranking the plurality of structurally hierarchical predictions of the structurally hierarchical prediction set based at least in part on the one or more up-weighting scores.

10. The one or more non-transitory computer storage media of claim 9, wherein the one or more prediction inputs comprise one or more unstructured prediction inputs and one or more structured prediction inputs; and the one or more processors are further caused to:
  generate a predictive output based at least in part on the reranked structurally hierarchical prediction set by:
  generating one or more structure-based predictions based at least in part on the one or more structured prediction inputs;
  generating one or more non-structure-based predictions based at least in part on the one or more unstructured prediction inputs; and
  generating, using an unstructured fusion machine learning model, the predictive output based at least in part on the one or more non-structure-based predictions in addition to the one or more structure-based predictions.

11. The one or more non-transitory computer storage media of claim 10, wherein:
  the one or more prediction inputs comprise one or more medical feature inputs for a patient profile, and
  the predictive output comprises at least one human phenotype ontology label prediction for the patient profile.

* * * * *

UNITED STATES PATENT AND TRADEMARK OFFICE
CERTIFICATE OF CORRECTION

| | | |
|---|---|---|
| PATENT NO. | : 12,026,591 B2 | Page 1 of 1 |
| APPLICATION NO. | : 16/523372 | |
| DATED | : July 2, 2024 | |
| INVENTOR(S) | : David S. Monaghan et al. | |

It is certified that error appears in the above-identified patent and that said Letters Patent is hereby corrected as shown below:

In the Claims

In Column 74, Line 40, Claim 5, delete "one or more" and insert -- plurality of --, therefor.

In Column 75, Line 15, Claim 9, delete "ofstructurally" and insert -- of structurally --, therefor.

Signed and Sealed this
Seventh Day of January, 2025

Derrick Brent
*Acting Director of the United States Patent and Trademark Office*